US012642773B2

(12) United States Patent
Wang et al.

(10) Patent No.: US 12,642,773 B2
(45) **Date of Patent: *Jun. 2, 2026**

(54) COATED DRUG COMPOSITIONS AND METHODS OF PREPARING THE SAME

(71) Applicant: Applied Materials, Inc., Santa Clara, CA (US)

(72) Inventors: Fei Wang, Fremont, CA (US); Miaojun Wang, Santa Clara, CA (US); Balaji Ganapathy, Maharashtra (IN); Jonathan Frankel, Los Gatos, CA (US); Shivkumar Chiruvolu, San Jose, CA (US); Pravin K. Narwankar, Sunnyvale, CA (US)

(73) Assignee: Applied Materials, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/737,814

(22) Filed: Jun. 7, 2024

(65) Prior Publication Data

US 2025/0009671 A1 Jan. 9, 2025

Related U.S. Application Data

(63) Continuation of application No. 17/341,213, filed on Jun. 7, 2021, now Pat. No. 12,161,759.

(60) Provisional application No. 63/035,639, filed on Jun. 5, 2020.

(51) Int. Cl.
| | |
|---|---|
| *A61K 9/50* | (2006.01) |
| *A61K 31/397* | (2006.01) |
| *A61K 31/4422* | (2006.01) |
| *A61K 31/517* | (2006.01) |

(52) U.S. Cl.
CPC ............ *A61K 9/501* (2013.01); *A61K 9/5089* (2013.01); *A61K 31/397* (2013.01); *A61K 31/4422* (2013.01); *A61K 31/517* (2013.01)

(58) Field of Classification Search
CPC .............................. A61K 9/5089; A61K 9/501
See application file for complete search history.

(56) References Cited

U.S. PATENT DOCUMENTS

| | | | |
|---|---|---|---|
| 10,034,854 B2 | 7/2018 | Lomuscio et al. | |
| 11,202,778 B2 | 12/2021 | Wertz et al. | |

| | | | |
|---|---|---|---|
| 12,161,759 B2 * | 12/2024 | Wang | A61K 9/5089 |
| 2013/0337056 A1 | 12/2013 | Lehtonen et al. | |
| 2016/0081945 A1 | 3/2016 | Carlsson et al. | |
| 2017/0209372 A1 * | 7/2017 | Temtem | A61K 9/10 |
| 2019/0062914 A1 | 2/2019 | King et al. | |
| 2019/0216742 A1 * | 7/2019 | Neikirk | A61K 31/424 |
| 2021/0378971 A1 | 12/2021 | Wang et al. | |

FOREIGN PATENT DOCUMENTS

WO WO 2019/143744 7/2019

OTHER PUBLICATIONS

Capece et al., "Enhanced Physical Stability of Amorphous Drug Formulations via Dry Polymer Coating," Journal of Pharmaceutical Sciences, Jun. 2015, 104(6):2076-2084.
Dameron et al., "Molecular Layer Deposition of Alucone Polymer Films Using Trimethylaluminum and Ethylene Glycol," Chemistry of Materials, Apr. 29, 2008, 20(10):3315-3326.
Extended European Search Report in European Appln. No. 21818417.4, dated Jun. 5, 2024, 12 pages.
Guns et al., "Comparison between hot-melt extrusion and spray-drying for manufacturing solid dispersions of the graft copolymer of ethylene glycol and vinyl alcohol," Pharmaceutical Research, Nov. 2010, vol. 28, pp. 673-682.
Hellrup et al., "Production and characterization of aluminum oxide nanoshells on spray dried lactose," International Journal of Pharmaceutics, Jun. 20, 2017, 529(1):116-122.
International Search Report and Written Opinion in International Appln. No. PCT/US2021/036183, dated Sep. 27, 2021, 11 pages.
LaFountaine et al., "Thermal Processing of PVP- and HPMC-Based Amorphous Solid Dispersions," AAPS PharmSciTech, Feb. 2016, 17(1):120-132.
Office Action in Taiwanese Appln. No. 110120405, dated Apr. 11, 2022, 6 pages (with English summary).
Perrotta et al., "Strategies for Drug Encapsulation and Controlled Delivery Based on Vapor-Phase Deposited Thin Films," Adv. Eng. Mater., Sep. 19, 2017, 20(3): 21 pages.
Puri et al., "Barrier Coated Drug Layered Particles for Enhanced Performance of Amorphous Solid Dispersion Dosage Form," Journal of Pharmaceutical Sciences, Jan. 2012, 101(1):342-353.

* cited by examiner

*Primary Examiner* — Michael B. Pallay
(74) *Attorney, Agent, or Firm* — Fish & Richardson P.C.

(57) ABSTRACT

A pharmaceutical composition containing a metal oxide coated particle comprising 1) an amorphous solid dispersion (ASD) core containing an active pharmaceutical ingredient (API) and a polymer; and 2) a metal oxide coating, and the method of making said metal oxide coated particle by atomic layer deposition (ALD). The metal oxide coated particle is useful because it prevents the ASD from crystallization and helps maintain the ASD in an amorphous form.

16 Claims, 98 Drawing Sheets

| Sample | Density (g/mL) | | Compressibility Index (%) | Hausner Ratio |
|---|---|---|---|---|
| | Bulk | Tapped | | |
| 50% Uncoated | 0.24 | 0.41 | 42.6 | 1.7 |
| B3-140 | 0.34 | 0.51 | 33.3 | 1.5 |
| B3-141 | 0.44 | 0.62 | 29.5 | 1.4 |
| 70% Uncoated | 0.26 | 0.41 | 36.4 | 1.6 |
| B3-139A | 0.42 | 0.62 | 32.1 | 1.5 |
| B3-138B | 0.48 | 0.63 | 25.0 | 1.3 |
| B3-139B | 0.48 | 0.63 | 24.6 | 1.3 |

FIG. 5A

| Flow Character | Compressibility Index (%) | Hausner Ratio |
|---|---|---|
| Excellent | ≤ 10 | 1.00 - 1.11 |
| Good | 11 - 15 | 1.12 - 1.18 |
| Fair | 16 - 20 | 1.19 - 1.25 |
| Passable | 21 - 25 | 1.26 - 1.34 |
| Poor | 26 - 31 | 1.35 - 1.45 |
| Very poor | 32 - 37 | 1.46 - 1.59 |
| Very, very poor | > 38 | > 1.60 |

Ref. United States Pharmacopoeia, (1174) POWDER FLOW

FIG. 5B

One year: 40C, 75 %RH

| Run ID | Process Temp (C) | Oxide wt% (TGA) | CBD (g/cm3) | CPS @15 kPa (%) | FTC @ 3 kPa |
|---|---|---|---|---|---|
| Un-coated | | | 0.196 | 49.0 | 1.7 ± 0.32 (3) |
| coated | 35 | 5.60 | 0.362 | 24.0 | 4.8 ± 0.40 (2) |

FIG. 23

| Lot # | Coating Thickness (TEM) | Oxide Content % |
|---|---|---|
| B3-284A (thin) | 4.4-5.5 nm | 1.69 |
| B3-284B (thick) | 8.8-9.4 nm | 3.31 |

| Sample ID | Surface layers |
|-----------|----------------|
| B3-284 A  | 4.4-5.5nm      |
| B3-284 B  | 8.8-9.4nm      |

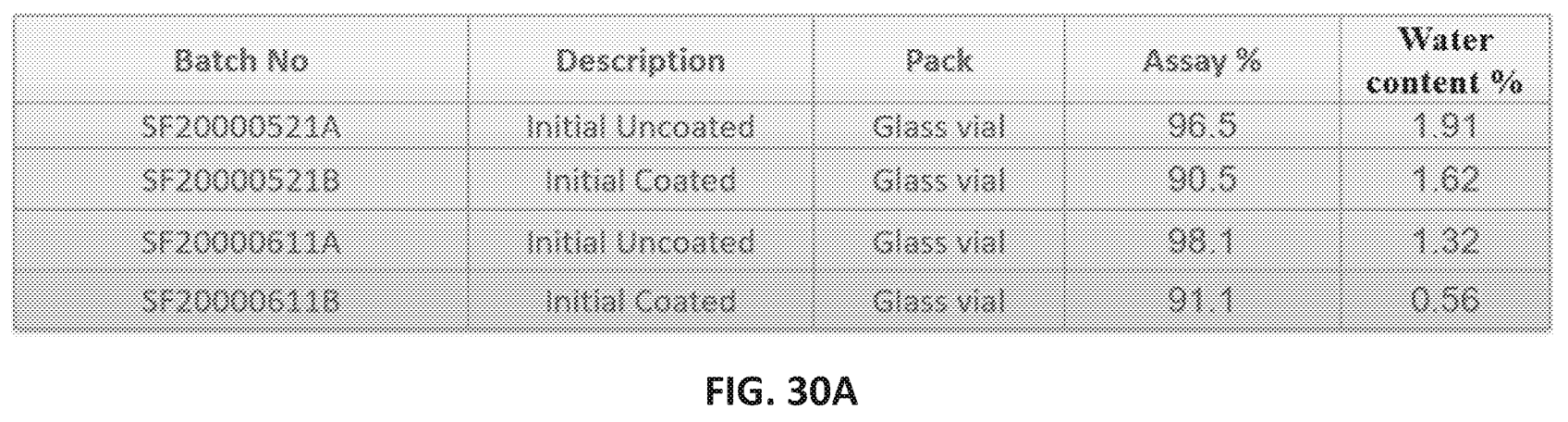

| Batch No | Description | Pack | Assay % | Water content % |
|---|---|---|---|---|
| SF20000521A | Initial Uncoated | Glass vial | 96.5 | 1.91 |
| SF20000521B | Initial Coated | Glass vial | 90.5 | 1.62 |
| SF20000611A | Initial Uncoated | Glass vial | 98.1 | 1.32 |
| SF20000611B | Initial Coated | Glass vial | 91.1 | 0.56 |

FIG. 30A

70% ASD: SF20000611B

50% ASD: SF20000521B

| Name of Product | Nifedipine ASD | | | | | | | | | | | |
|---|---|---|---|---|---|---|---|---|---|---|---|---|
| Batch No. | SF20000521A (50% UNCOATED) | | | | | | | | | | | |
| Study Start Date | Jan 2021 | | | | | | | | | | | |
| Tests | Pack type | | Conditions | | | | | | | | | |
| | | Initial | 25°C / 60%RH (amber vials) | | 40°C / 75%RH (capped HDPE) | | | 40°C / 75%RH (OE, HDPE) | | | | |
| | | | 2M | 3M | 2M | 3M | | 1M | 2M | 3M | | |
| Assay (%) | Amber vials and HDPE bottles | 96.5 | 95.4 | 95.6 | 93.4 | 91.8 | | 90.5 | 89.1 | 87.2 | | |
| Water content (%) | | 1.91 | 2.86 | 2.35 | 4.28 | 4.57 | | 5.13 | 5.99 | 6.58 | | |
| Highest unknown impurity (%) | | 0.201 | 0.190 | 0.194 | 0.828 | 1.27 | | 0.886 | 1.526 | 1.26 | | |
| Total impurities (%) | | 0.447 | 0.704 | 0.781 | 2.281 | 3.668 | | 2.881 | 5.947 | 5.188 | | |

FIG. 33A

| Name of Product | Nifedipine ASD | | | | | | | | | | | | |
| Batch No. | SF20000521B (50% COATED) | | | | | | | | | | | | |
| Study Start Date | Jan 2021 | | | | | | | | | | | | |
| Tests | Pack type | | Conditions | | | | | | | | | | |
| | | | | 25°C / 60%RH (amber vials) | | 40°C / 75%RH (capped HDPE) | | | 40°C / 75%RH (OE, HDPE) | | | |
| | | Initial | | 2M | 3M | 2M | 3M | | 1M | 2M | 3M | |
| Assay (%) | Amber vials and HDPE bottles | 90.5 | | 88.1 | 90.2 | 87.8 | 86.5 | | 86.2 | 86.3 | 86.4 | |
| Water content (%) | | 1.62 | | 3.88 | 1.72 | 3.66 | 5.45 | | 5.20 | 5.55 | 5.89 | |
| Highest unknown impurity (%) | | 0.205 | | 0.199 | 0.209 | 0.288 | 0.377 | | 0.263 | 0.307 | 0.290 | |
| Total impurities (%) | | 0.539 | | 0.660 | 0.636 | 1.085 | 1.701 | | 1.176 | 1.411 | 1.337 | |

FIG. 33B

| Name of Product | Nifedipine ASD | | | | | | | |
| Batch No. | SF2000611A (70% UNCOATED) | | | | | | | |
| Study Start Date | Jan 2021 | | | | | | | |

| Tests | Pack type | Conditions | | | | | | |
| | | Initial | 25°C / 60%RH (amber vials) | | 40°C / 75%RH (HDPE) | 40°C / 75%RH (capped HDPE) | 40°C / 75%RH (OE, HDPE) | | |
| | | | 2M | 3M | 2M | 3M | 1M | 2M | 3M |
| Assay (%) | Amber vials and HDPE bottles | 98.1 | 98.9 | 97.2 | 97.6 | 96.9 | 97.0 | 97.5 | 97.5 |
| Water content (%) | | 1.32 | 2.02 | 3.53 | 2.88 | 2.95 | 2.71 | 3.08 | 3.52 |
| Highest unknown impurity (%) | | 0.214 | 0.224 | 0.223 | 0.216 | 0.212 | 0.201 | 0.219 | 0.205 |
| Total impurities (%) | | 0.313 | 0.356 | 0.352 | 0.388 | 0.514 | 0.363 | 0.442 | 0.466 |

FIG. 33C

| Name of Product | Nifedipine ASD | | | | | | | | |
|---|---|---|---|---|---|---|---|---|---|
| Batch No. | SF20000611B (70% COATED) | | | | | | | | |
| Study Start Date | Jan 2021 | | | | | | | | |
| Tests | Pack type | | Conditions | | | | | | |
| | | Initial | 25°C / 60%RH (amber vials) | | 40°C / 75%RH (capped HDPE) | | 40°C / 75%RH (OE, HDPE) | | |
| | | | 2M | 3M | 2M | 3M | 1M | 2M | 3M |
| Assay (%) | Amber vials and HDPE bottles | 91.1 | 91.0 | 89.3 | 89.5 | 89.2 | 90.0 | 90.0 | 90.0 |
| Water content (%) | | 0.56 | 1.54 | 1.01 | 2.58 | 2.08 | 2.85 | 3.28 | 3.39 |
| Highest unknown impurity (%) | | 0.213 | 0.222 | 0.221 | 0.217 | 0.215 | 0.199 | 0.224 | 0.208 |
| Total impurities (%) | | 0.412 | 0.413 | 0.360 | 0.427 | 0.419 | 0.269 | 0.423 | 0.495 |

FIG. 33D

1month

2month

3month 1 month

2month

3month 1 month

2month

3month 0 month 2 month 3 month 0 month 2 month 3 month

COATED DRUG COMPOSITIONS AND METHODS OF PREPARING THE SAME

CROSS-REFERENCE TO RELATED APPLICATIONS

This application claims priority to U.S. application Ser. No. 17/341,213, filed on Jun. 7, 2021, which claims priority to U.S. Provisional Application Ser. No. 63/035,639, filed on Jun. 5, 2020, the disclosure of which is incorporated by reference.

TECHNICAL FIELD

This disclosure pertains to coated drug compositions and methods of preparing coated drug compositions.

BACKGROUND

It is of great interest to the pharmaceutical industry to develop improved formulations of active pharmaceutical ingredients (APIs). Formulation can influence the stability and bioavailability of the APIs as well as other characteristics. Formulation can also influence various aspects of drug product (DP) manufacture, for example, the ease and safety of the manufacturing process.

Many APIs are poorly soluble. Among approved drugs, about 40% contain an API that is poorly soluble. The percentage of poorly soluble compounds among those in development is far higher. Poor solubility contributes to poor bioavailability. Amorphous forms of APIs are generally more soluble than the crystalline form. Thus, it is often desirable to produce a drug formulation in which the API is amorphous rather than crystalline and remains amorphous during storage. An amorphous solid dispersion (ASD) of an API in, usually, a polymer can stabilize the amorphous form of the API against crystallization. ASDs have advantages in terms of supersaturation solubility, dissolution, and improved bioavailability. ASDs are thermodynamically unstable compared to the crystalline form of the API. However, the polymer matrix inhibits recrystallization, for example by exhibiting higher viscosity below the glass transition temperature (Tg) or through drug-polymer interactions. ASD are most often created by hot-melt extrusion, spray drying or anti-solvent precipitation. Ideally, ASDs would be kinetically stable for the duration of their anticipated shelf-life, but most revert to the crystalline form. Exposure to high humidity or high temperature significantly increases the mobility of the API in the ASD and reduces the ability of polymers to inhibit recrystallization. Crystallization of an API in an ASD can occur both via bulk crystallization and surface crystallization.

SUMMARY

Described herein is a method of preparing a pharmaceutical composition comprising coated particles comprising amorphous solid dispersion of an active pharmaceutical ingredient (ASD particles) enclosed by one or more metal oxide layers, the method comprising the sequential steps of: (a) providing particles of an amorphous solid dispersion comprising an active pharmaceutical ingredient and a polymer; (b) performing atomic layer deposition to apply a metal oxide layer to particles of an amorphous solid dispersion comprising an active pharmaceutical ingredient and a polymer thereby preparing coated particles comprising an active pharmaceutical ingredient enclosed by one or more metal oxide layers; and (c) processing the coated particles to prepare a pharmaceutical composition.

In various embodiments: the particles are at least 50%, 60%, 65%, 70%, wt/wt drug; the particles have a D50 of 0.1 μm to 200 μm (e.g., 0.1 μm to 10 μm or 0.1 μm to 5 μm) on a volume average basis; the particles have a D90 of 200 μm to 2000 μm on a volume average basis; the glass transition temperature of the active pharmaceutical ingredient in the coated particles is higher than the glass transition temperature of the active pharmaceutical ingredient in the provided particles;

the polymer is selected from the group consisting of: hydroxypropyl methylcellulose, hydroxypropyl methyl cellulose acetate succinate (HPMCAS), and polyvinylpyrrolidone (PVP), polyvinylpyrrolidone/vinyl acetate (PVPVA), polyethylene glycol (PEG), polyacrylates and polymethacrylates; step (a) comprises preparing ASD particles by hot melt extrusion; step (a) comprises preparing ASD particles by spray drying;

In various embodiments: the step of performing atomic layer deposition comprises:

(b1) loading the particles comprising the drug into a reactor;

(b2) applying a vaporous or gaseous metal precursor to the particles in the reactor;

(b3) performing one or more pump-purge cycles of the reactor using inert gas;

(b4) applying a vaporous or gaseous oxidant to the particles in the reactor; and (b5) performing one or more pump-purge cycles of the reactor using inert gas.

In various embodiments: steps (b2)-(b5) are performed two or more times to increase the total thickness of the metal oxide layer before step (c) is performed; the reactor contents are agitated prior to and/or during step (a); the reactor pressure is allowed to stabilize following step (b1), step (b2), and/or step (b4); the reactor contents are agitated prior to and/or during step (b1), step (b3), and/or step (b5); a subset of vapor or gaseous content is pumped out prior to step (b3) and/or step (b5); the metal oxide layer has a thickness in range of 0.1 nm to 100 nm (e.g., 0.1 nm to 50 nm); step (c) comprises combining the coated particles with one or more pharmaceutically acceptable excipients; the metal oxide is selected from the group consisting of: zinc oxide, aluminum oxide, silicon oxide and titanium oxide; step (b) takes place at a temperature between 25° C. and 50° C.;

step (b) takes place at a temperature between 25° C. and 100° C.

Also described is a pharmaceutical composition comprising coated particles comprising amorphous solid dispersion of an active pharmaceutical ingredient enclosed by one or more metal oxide layers, prepared by a method comprising the sequential steps of:

(a) providing particles of an amorphous solid dispersion comprising an active pharmaceutical ingredient and a polymer;

(b) performing atomic layer deposition to apply a metal oxide layer to particles of an amorphous solid dispersion comprising an active pharmaceutical ingredient and a polymer thereby preparing coated particles comprising an active pharmaceutical ingredient enclosed by one or more metal oxide layers; and (c) processing the coated particles to prepare a pharmaceutical composition.

In various embodiments of the composition: the step of performing atomic layer deposition comprises:

(b1) loading the particles comprising the drug into a reactor;

(b2) applying a vaporous or gaseous metal precursor to the particles in the reactor;

(b3) performing one or more pump-purge cycles of the reactor using inert gas;

(b4) applying a vaporous or gaseous oxidant to the particles in the reactor; and (b5) performing one or more pump-purge cycles of the reactor using inert gas.

In various embodiments of the composition: the particles are at least 50%, 60%, 65%, 70%, wt/wt drug; the particles have a D50 of 0.1 µm to 200 µm (e.g., 0.1 µm to 10 µm or 0.1 µm to 5 µm) on a volume average basis; the particles have a D90 of 200 µm to 2000 µm on a volume average basis; the glass transition temperature of the active pharmaceutical ingredient in the coated particles is higher than the glass transition temperature of the active pharmaceutical ingredient in the provided particles; the polymer is selected from the group consisting of: hydroxypropyl methylcellulose, hydroxypropyl methyl cellulose acetate succinate, and polyvinylpyrrolidone, polyvinylpyrrolidone/vinyl acetate, polyethylene glycol (PEG), polyacrylates and polymethacrylates; step (a) comprises preparing ASD particles by hot melt extrusion; step (a) comprises preparing ASD particles by spray drying;

In various embodiments: the step of performing atomic layer deposition comprises:

(b1) loading the particles comprising the drug into a reactor;

(b2) applying a vaporous or gaseous metal precursor to the particles in the reactor;

(b3) performing one or more pump-purge cycles of the reactor using inert gas;

(b4) applying a vaporous or gaseous oxidant to the particles in the reactor; and (b5) performing one or more pump-purge cycles of the reactor using inert gas.

In various embodiments: steps (b2)-(b5) are performed two or more times to increase the total thickness of the metal oxide layer before step (c) is performed; the reactor contents are agitated prior to and/or during step (a); the reactor pressure is allowed to stabilize following step (b1), step (b2), and/or step (b4); the reactor contents are agitated prior to and/or during step (b1), step (b3), and/or step (b5); a subset of vapor or gaseous content is pumped out prior to step (b3) and/or step (b5); the metal oxide layer has a thickness in range of 0.1 nm to 100 nm; step (c) comprises combining the coated particles with one or more pharmaceutically acceptable excipients; the metal oxide is selected from the group consisting of: zinc oxide, aluminum oxide, silicon oxide and titanium oxide; step (b) takes place at a temperature between 25° C. and 50° C.; step (b) takes place at a temperature between 25° C. and 50° C.

Prior to coating, particles may have a median particle size, on a volume average basis, between 0.01 µm and 1000 µm.

The pharmaceutical composition may be removed from the reactor and admixed with one or more pharmaceutically acceptable diluent or carrier.

Prior to coating, the particles may consist essentially of an API.

The one or more oxide materials include silicon oxide and various metal oxides including: aluminum oxide, titanium oxide, iron oxide, gallium oxide, magnesium oxide, zinc oxide, niobium oxide, hafnium oxide, tantalum oxide, lanthanum oxide, and/or zirconium dioxide.

The oxidant may be selected from the group of water, ozone, and organic peroxide.

Unless otherwise defined, all technical and scientific terms used herein have the same meaning as commonly understood by one of ordinary skill in the art to which this invention belongs. Methods and materials are described herein for use in the present invention; other suitable methods and materials known in the art can also be used. The materials, methods, and examples are illustrative only and not intended to be limiting.

Other features and advantages of the invention will be apparent from the following detailed description and figures, and from the claims.

BRIEF DESCRIPTION OF THE DRAWINGS

FIGS. 5A-5B depict the results of bulk and tapped density analysis of uncoated and metal oxide coated ASD particles.

17, there was about 25% crystallinity for uncoated ASD with 50% API loading, about 50% crystallinity for uncoated ASD with 70% API loading, and no crystallization for most of the coated samples.

Figure 18:
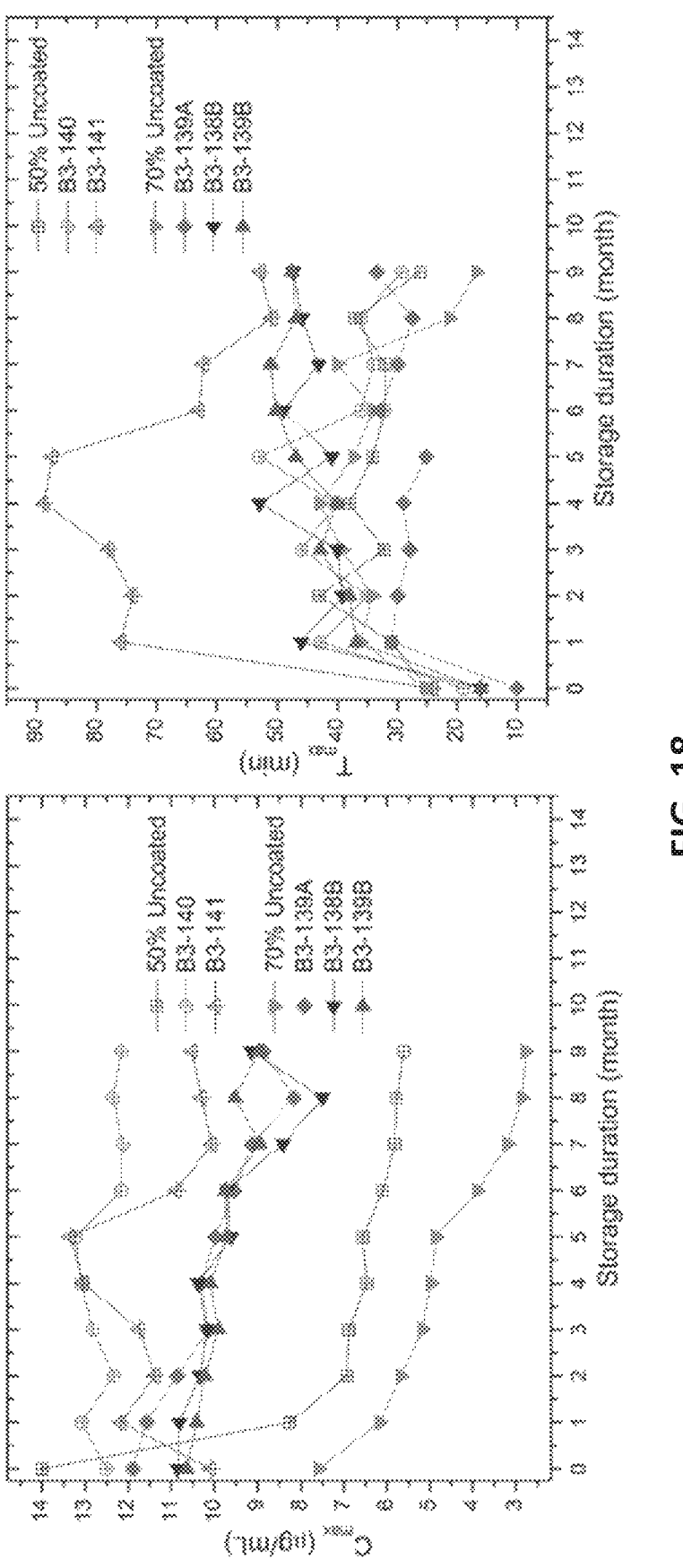

FIG. 18 depicts the results of release study of uncoated and metal oxide coated ASD particles (aluminum oxide/ezetimibe/HPMCAS) after storage at 40° C. and 75% relative humidity for various durations.

Figure 19:
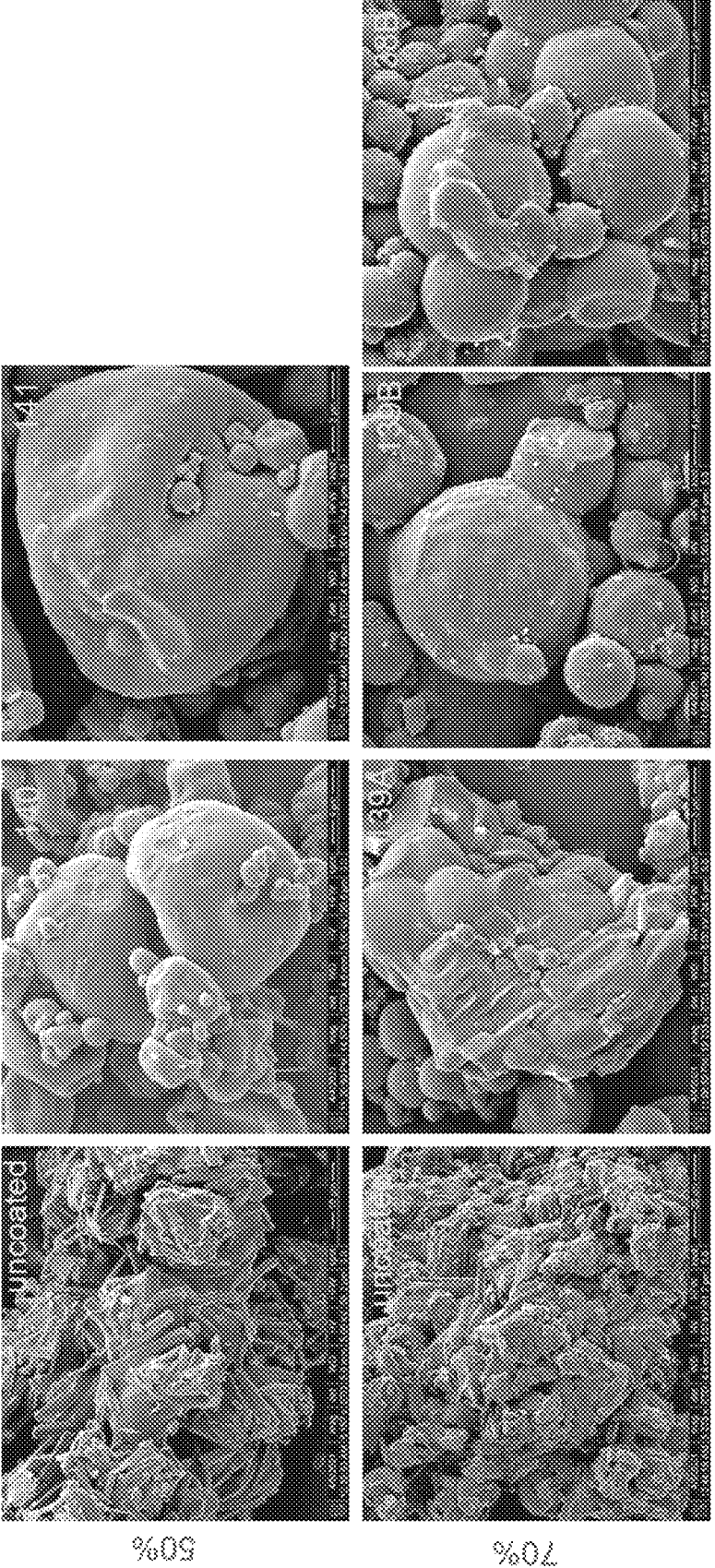

FIG. 19 depicts scanning electron microscopy images of uncoated and metal oxide coated ASD particles (aluminum oxide/ezetimibe/HPMCAS) after one year storage at 40° C. and 75% relative humidity.

Figure 20:
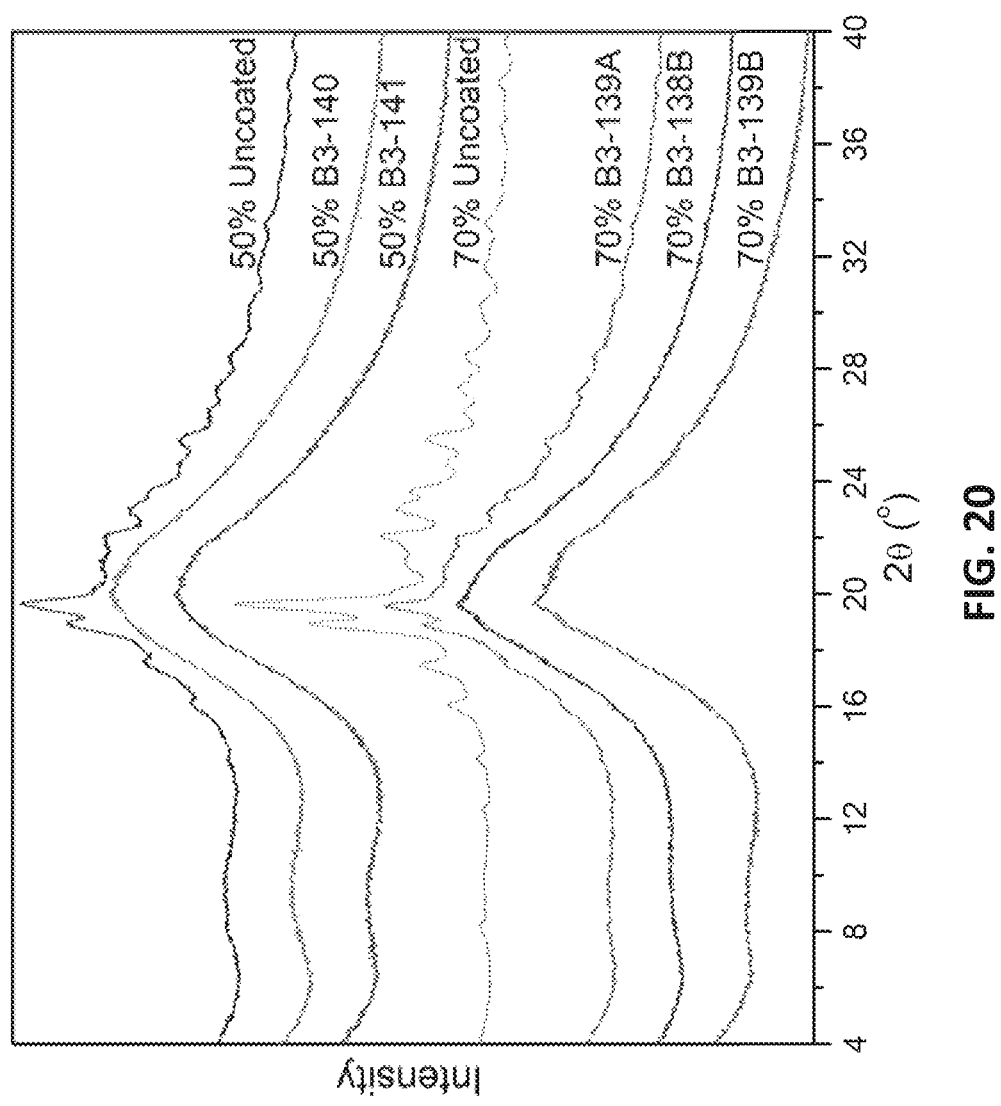

FIG. 20 depicts the results of x-ray diffraction analysis of uncoated and metal oxide coated ASD particles (aluminum oxide/ezetimibe/HPMCAS) after one year storage at 40° C. and 75% relative humidity.

Figure 21A:
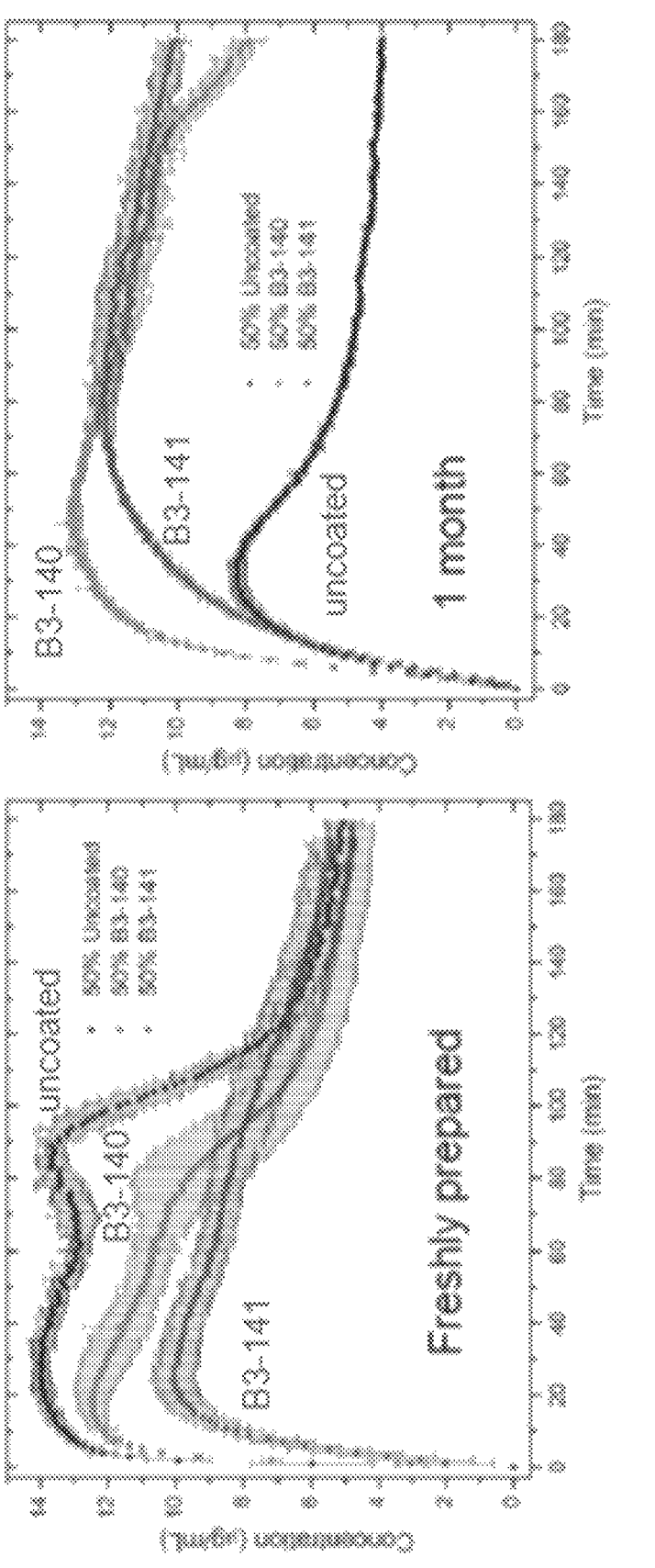
Figure 21B:
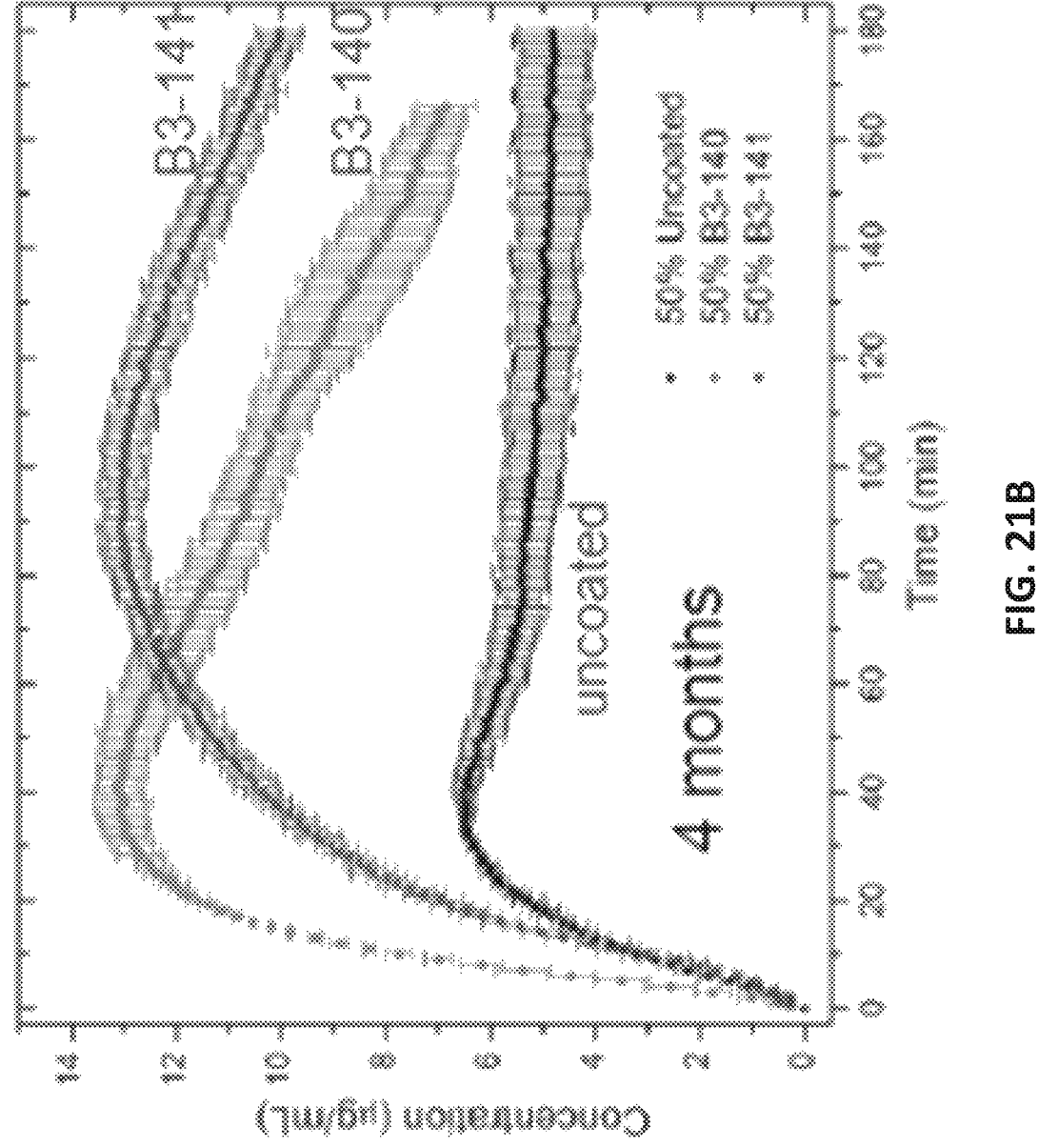
Figure 21C:
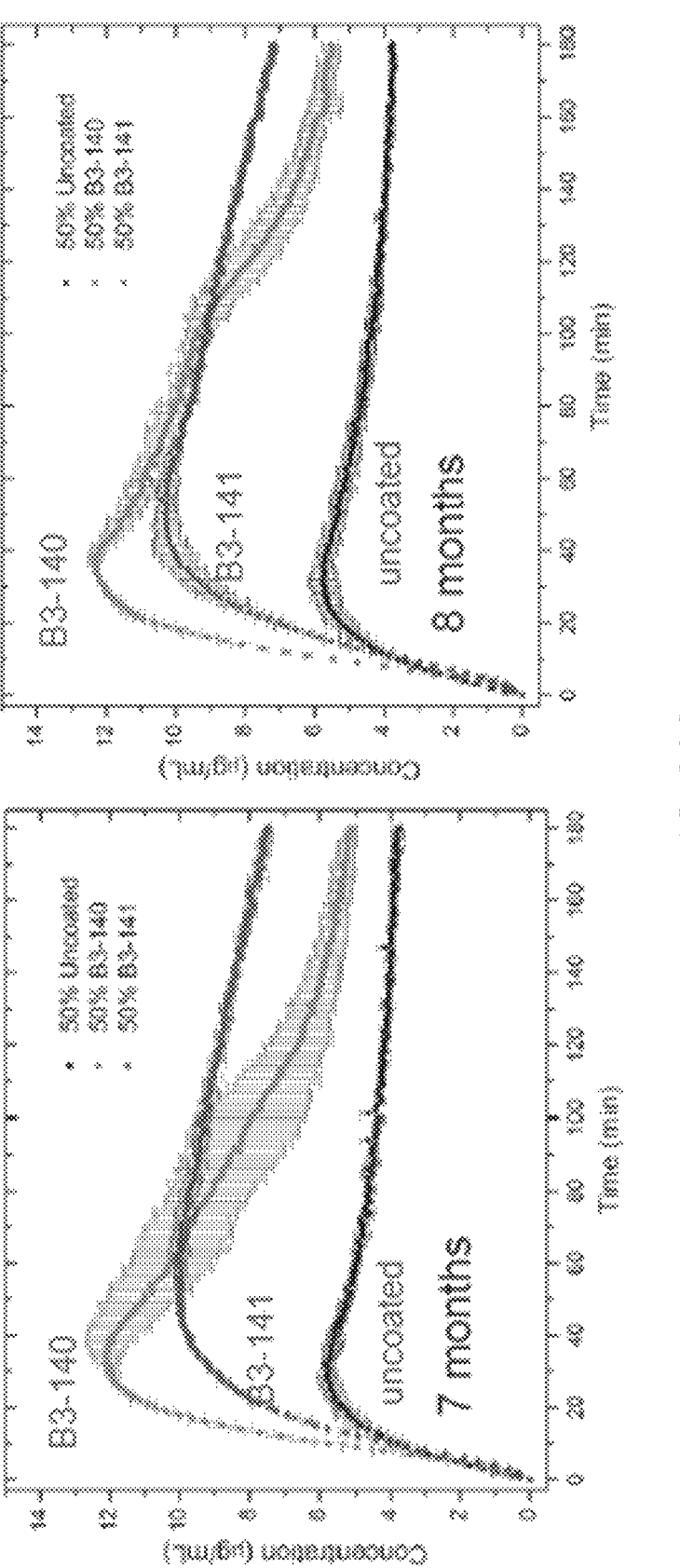
Figure 21D:
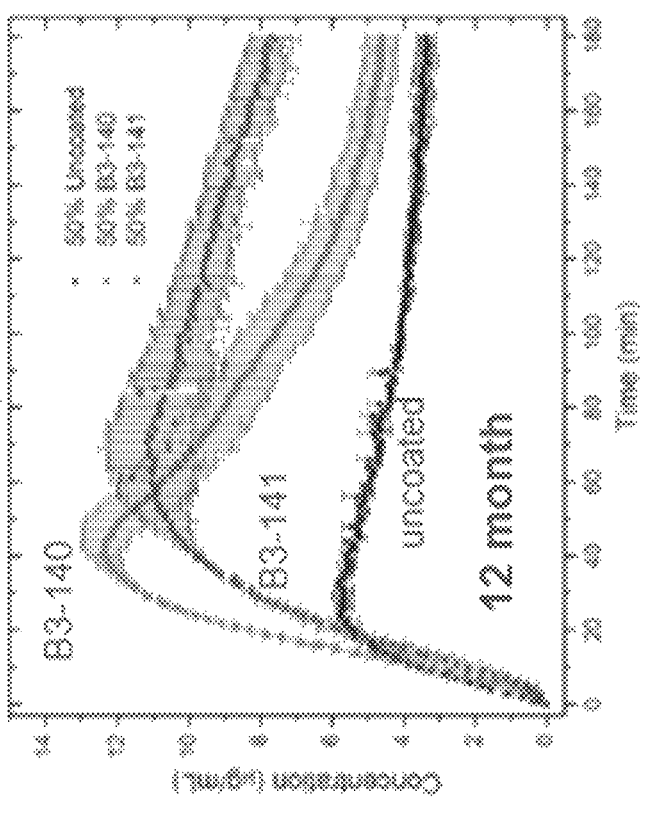
Figure 21D:
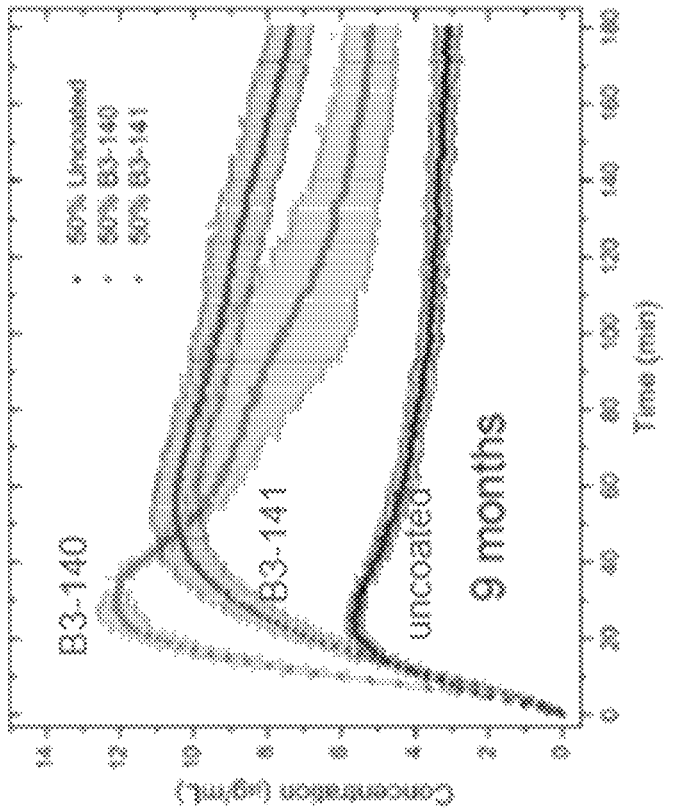
Figure 21E:
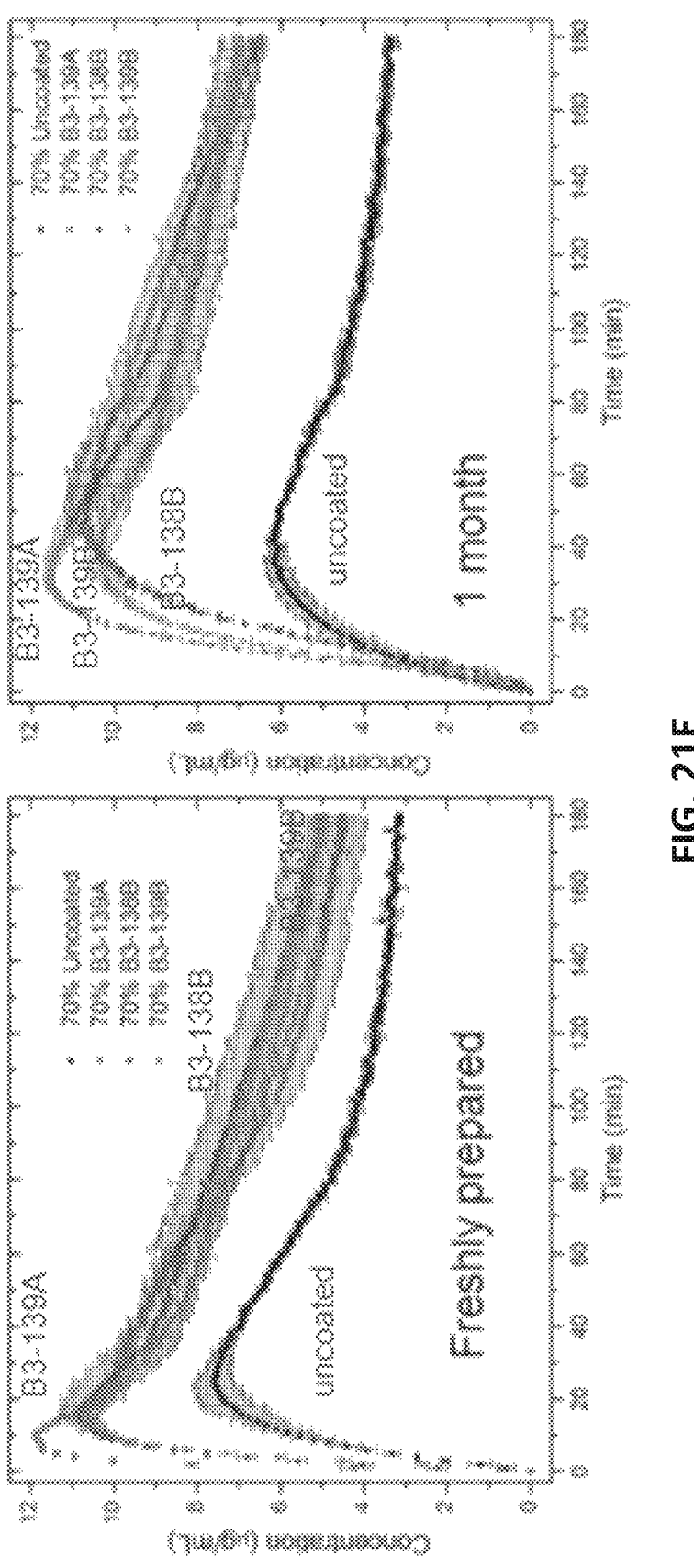
Figure 21F:
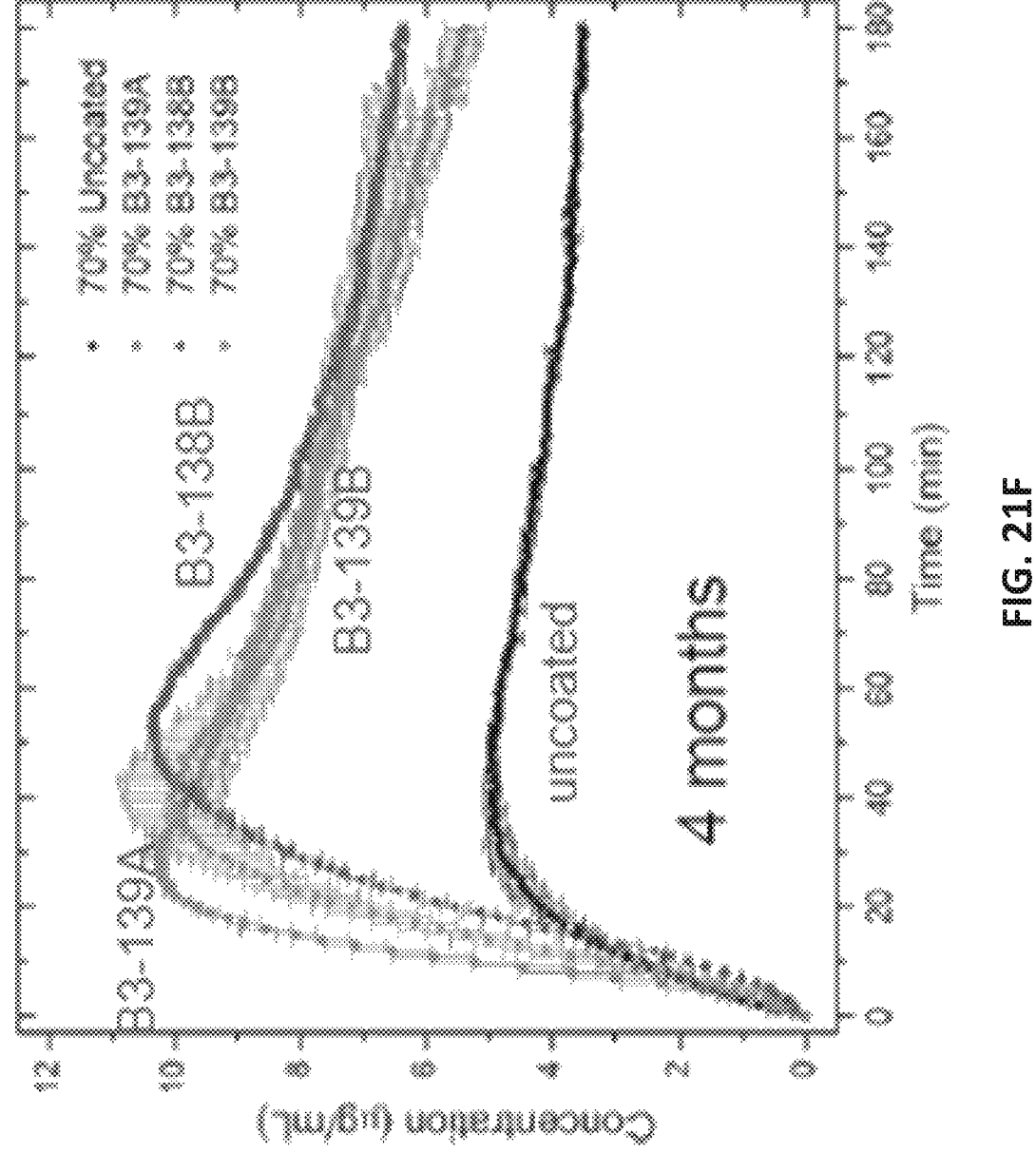
Figure 21G:
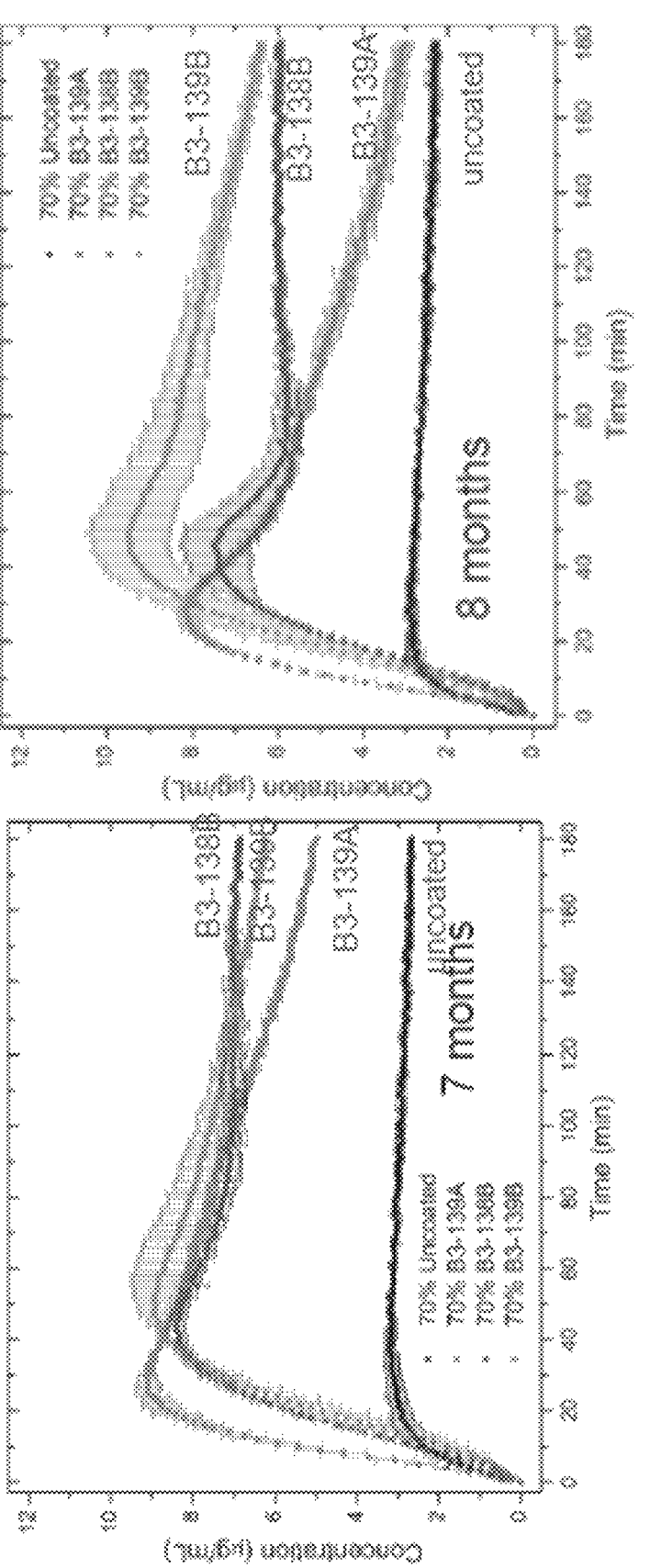
Figure 21H:
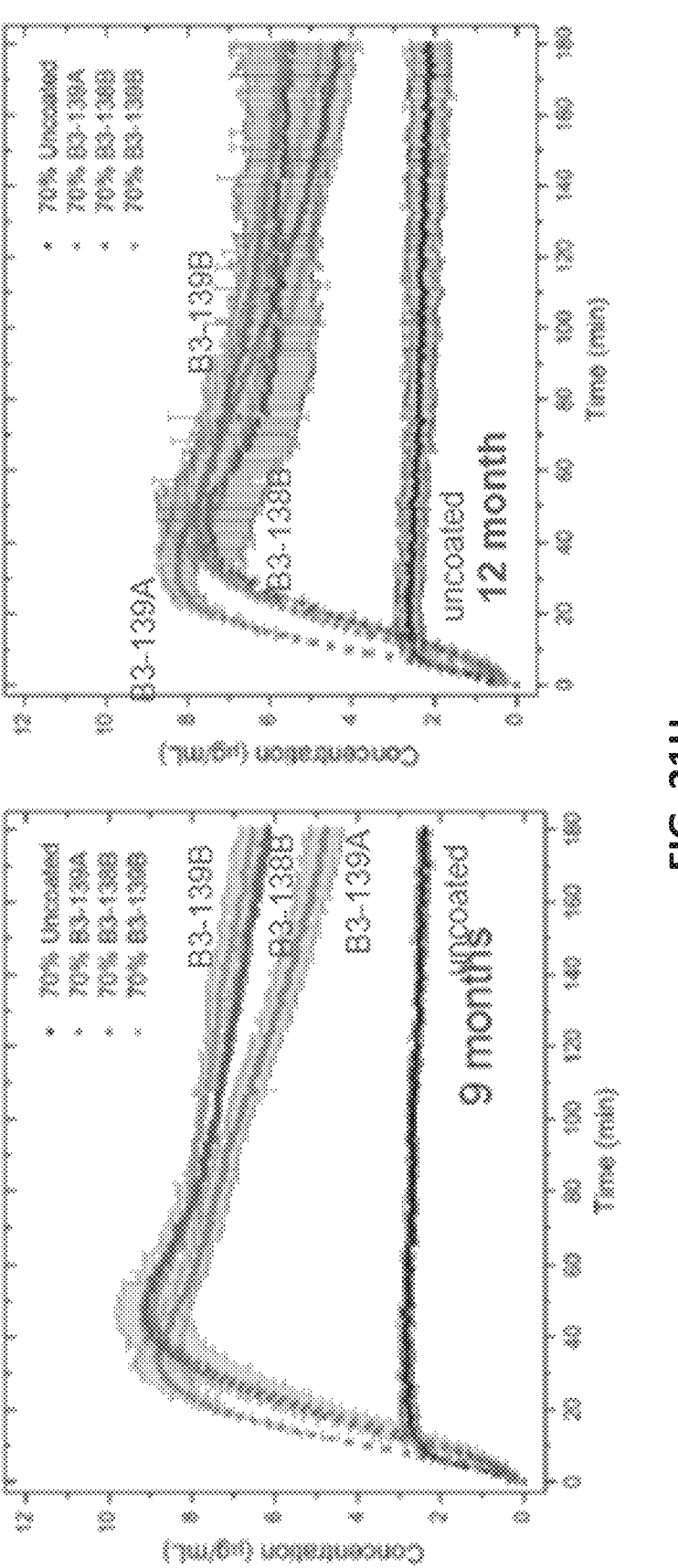
Figure 21I:
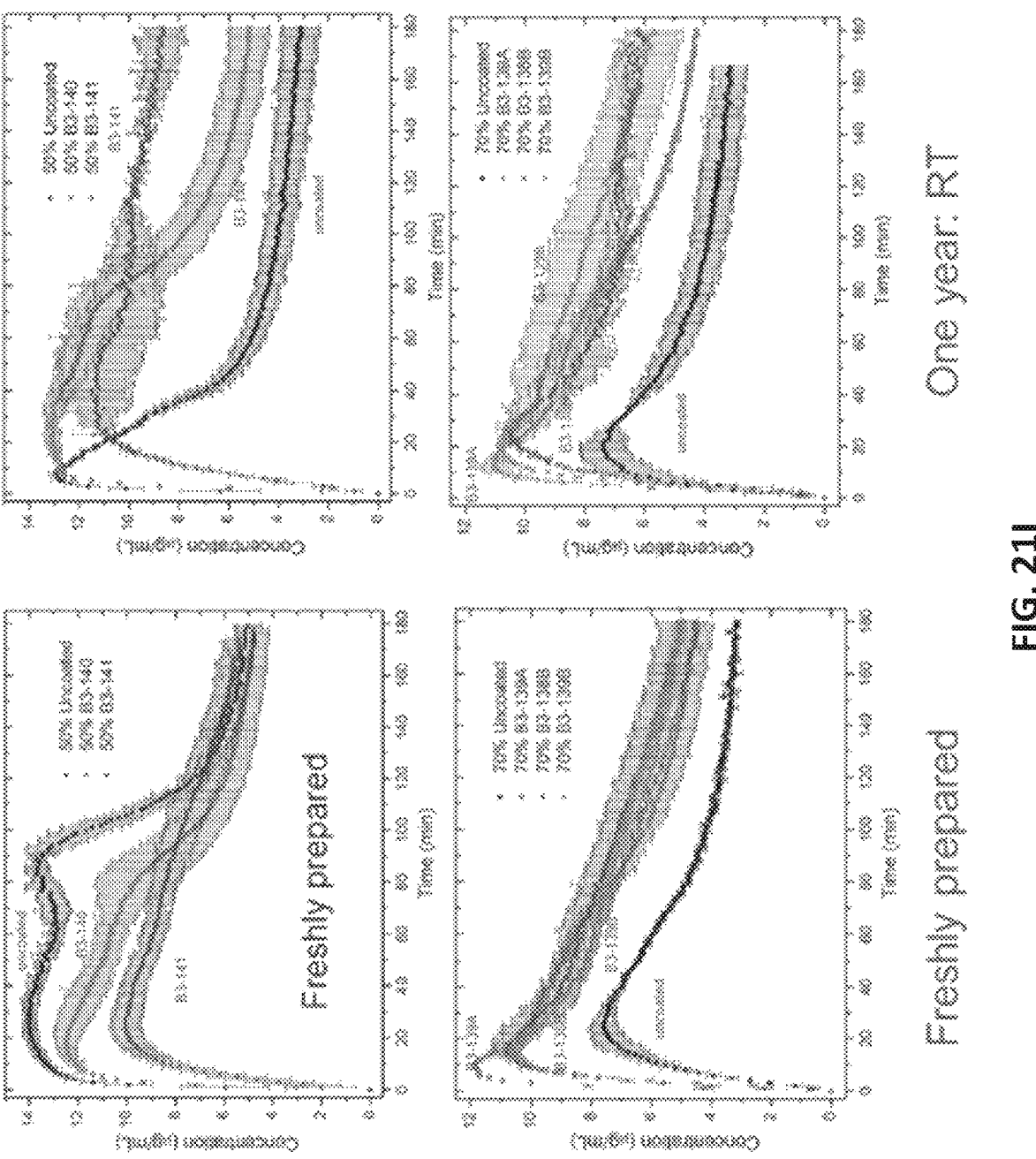
Figure 21J:
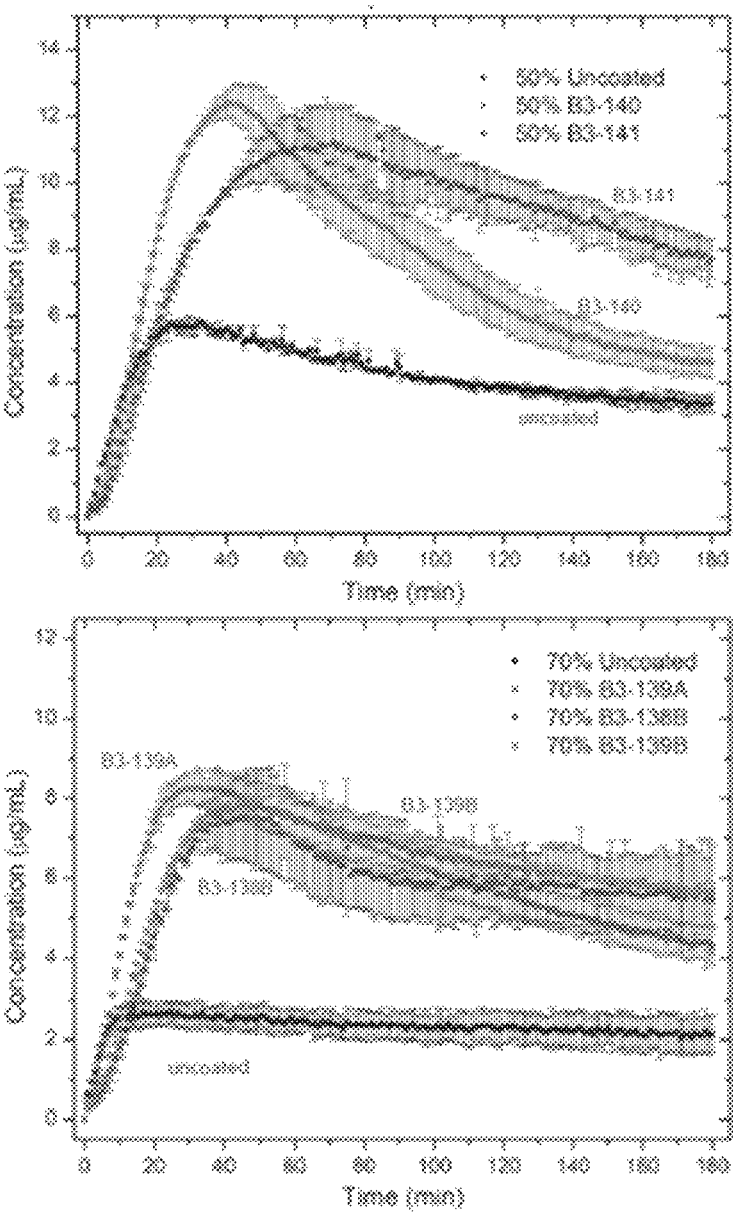

FIGS. 21A-21J depict the results of dissolution analysis of uncoated and metal oxide coated ASD particles (aluminum oxide/ezetimibe/HPMCAS) after storage at 40° C. and 75% relative humidity for various durations. FIGS. 21I-21J depict the results of dissolution analysis of uncoated and metal oxide coated ASD particles (aluminum oxide/ezetimibe/HPMCAS) after one year storage at either room temperature or 40° C. and 75% relative humidity.

Figure 22A:
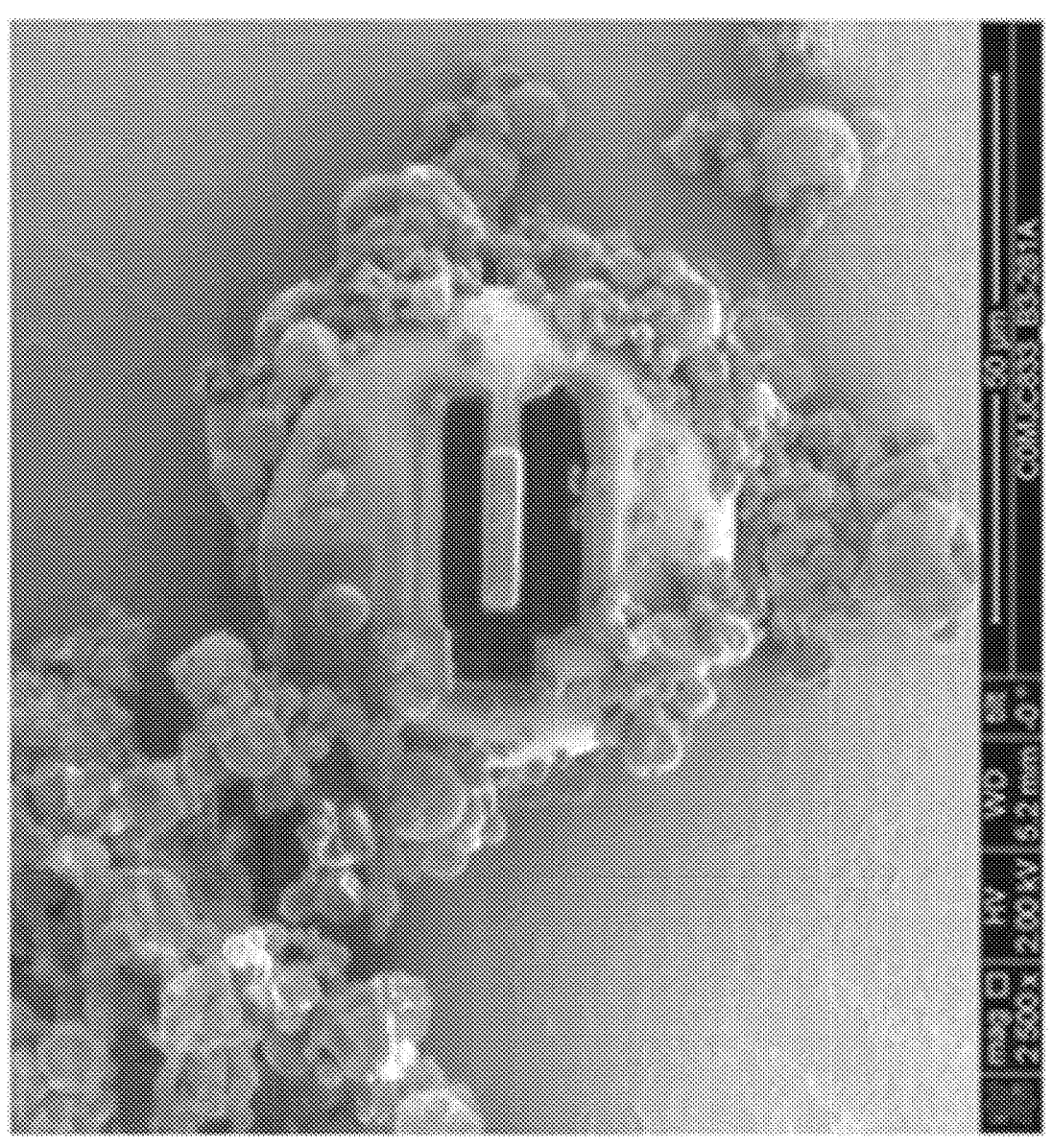
Figure 22B:
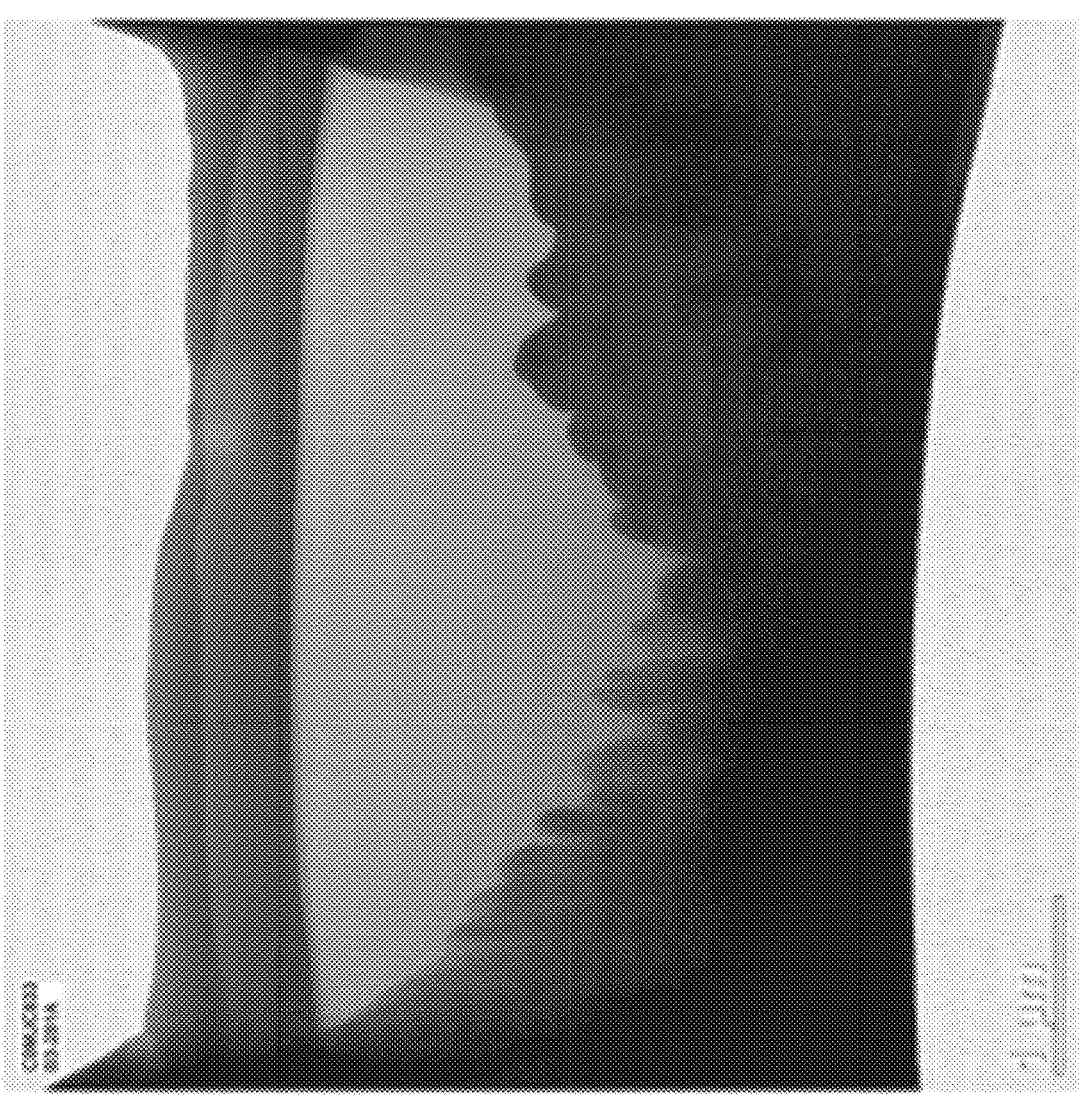
Figure 22C:
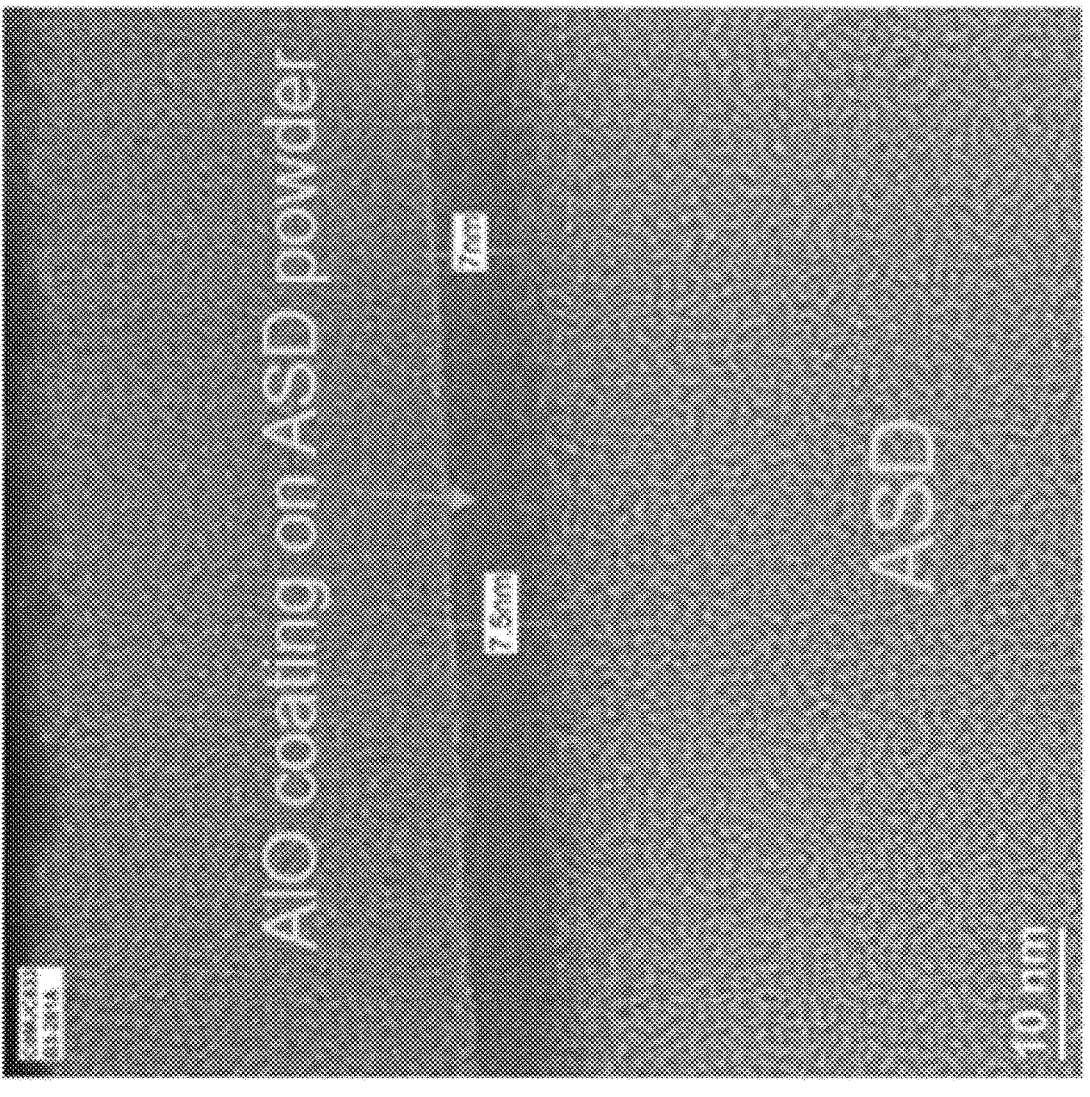

FIGS. 22A-22C depict SEM and TEM/FIB cross section images of metal oxide coated ASD particles (aluminum oxide/erlotinib/HPMCAS) with 60% drug loading.

FIG. 23 depicts powder flowability characterization of uncoated and metal oxide coated ASD particles (aluminum oxide/erlotinib/HPMCAS) with 60% drug loading.

Figure 24:
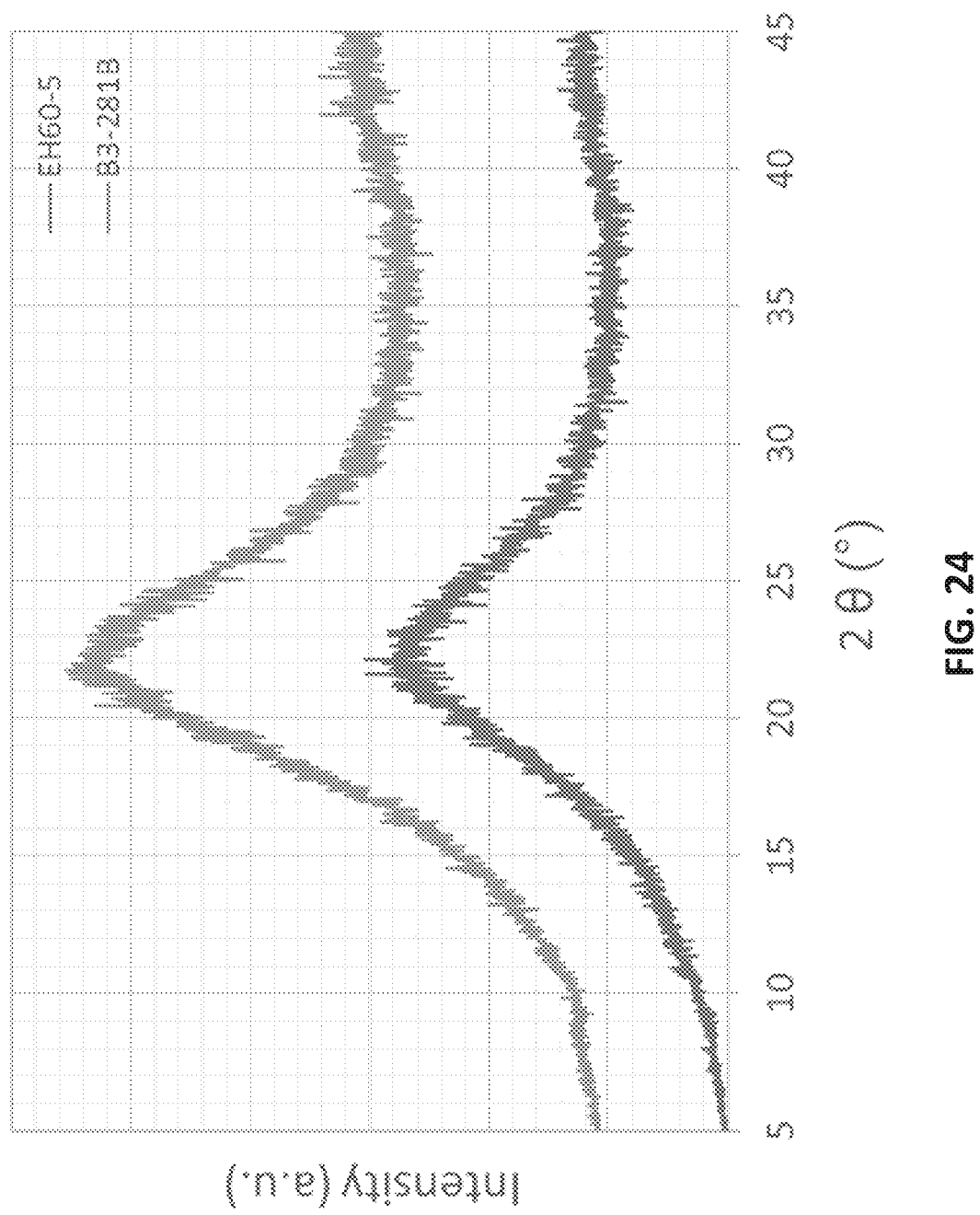

FIG. 24 depicts the results of x-ray diffraction analysis of uncoated and metal oxide coated ASD particles (aluminum oxide/erlotinib/HPMCAS) with 60% drug loading.

Figure 25A:
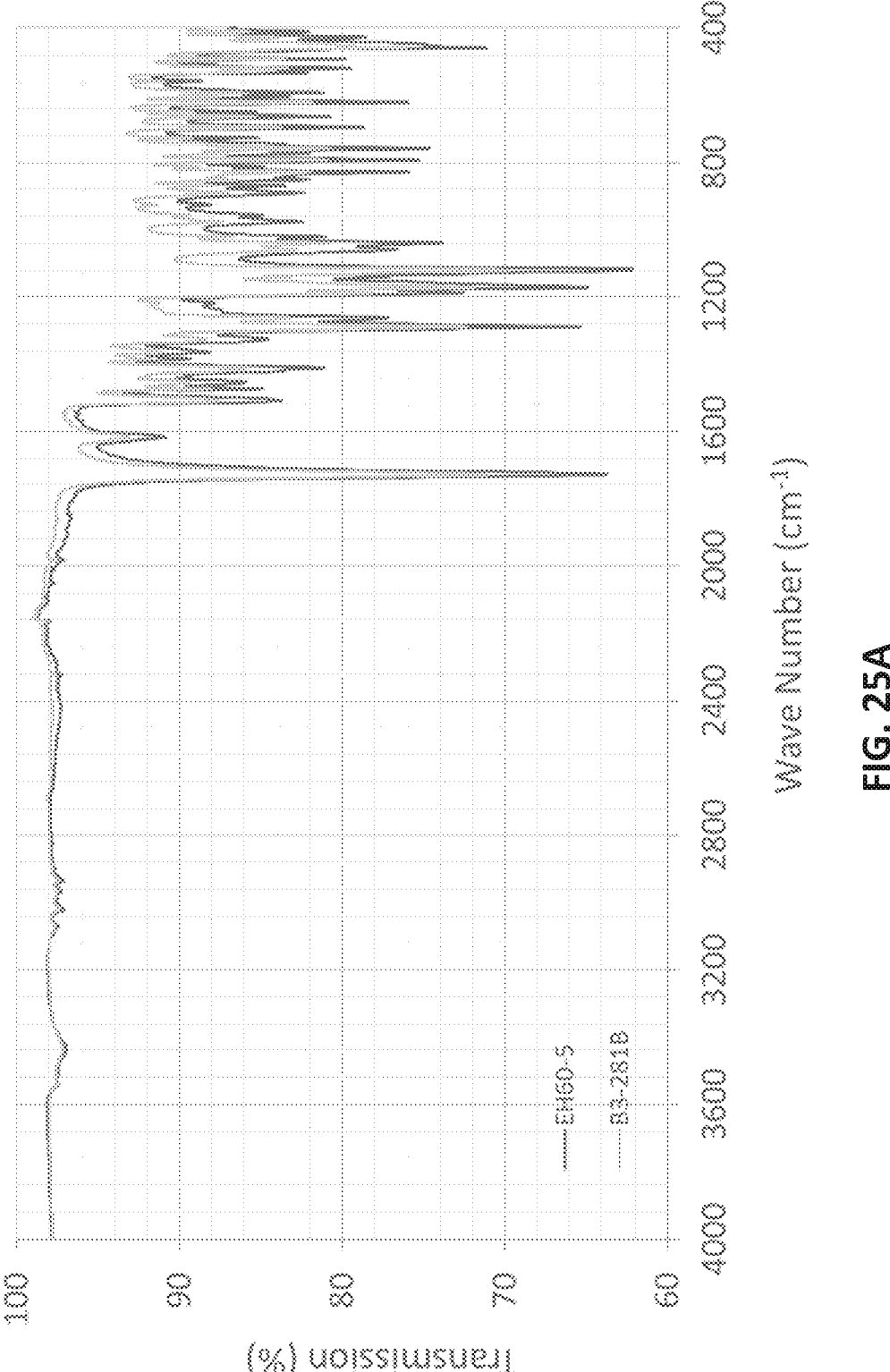
Figure 25B:
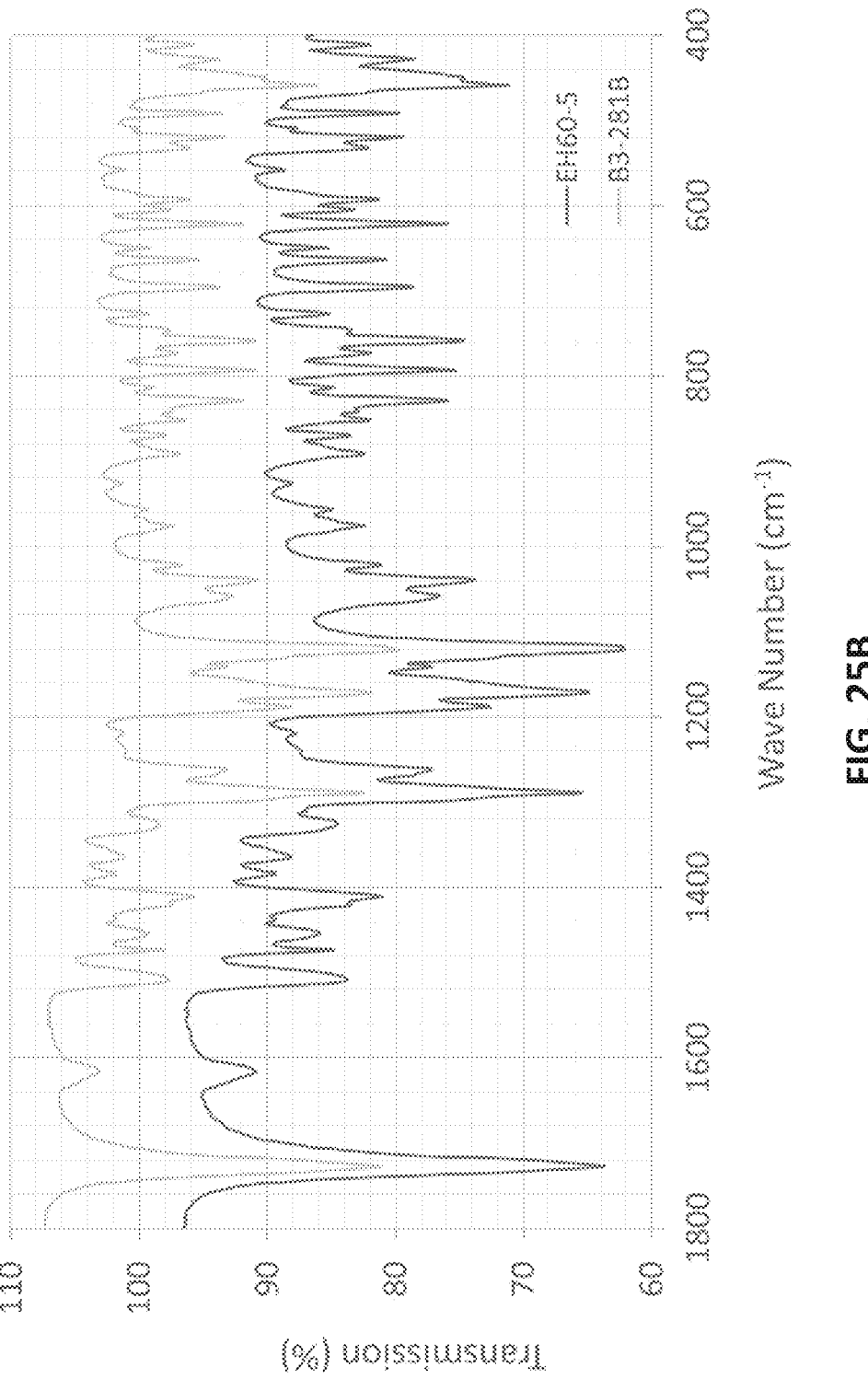

FIGS. 25A and 25B depict the results of FTIR analysis of uncoated and metal oxide coated ASD particles (aluminum oxide/erlotinib/HPMCAS) with 60% drug loading.

Figures 26A, 26B:
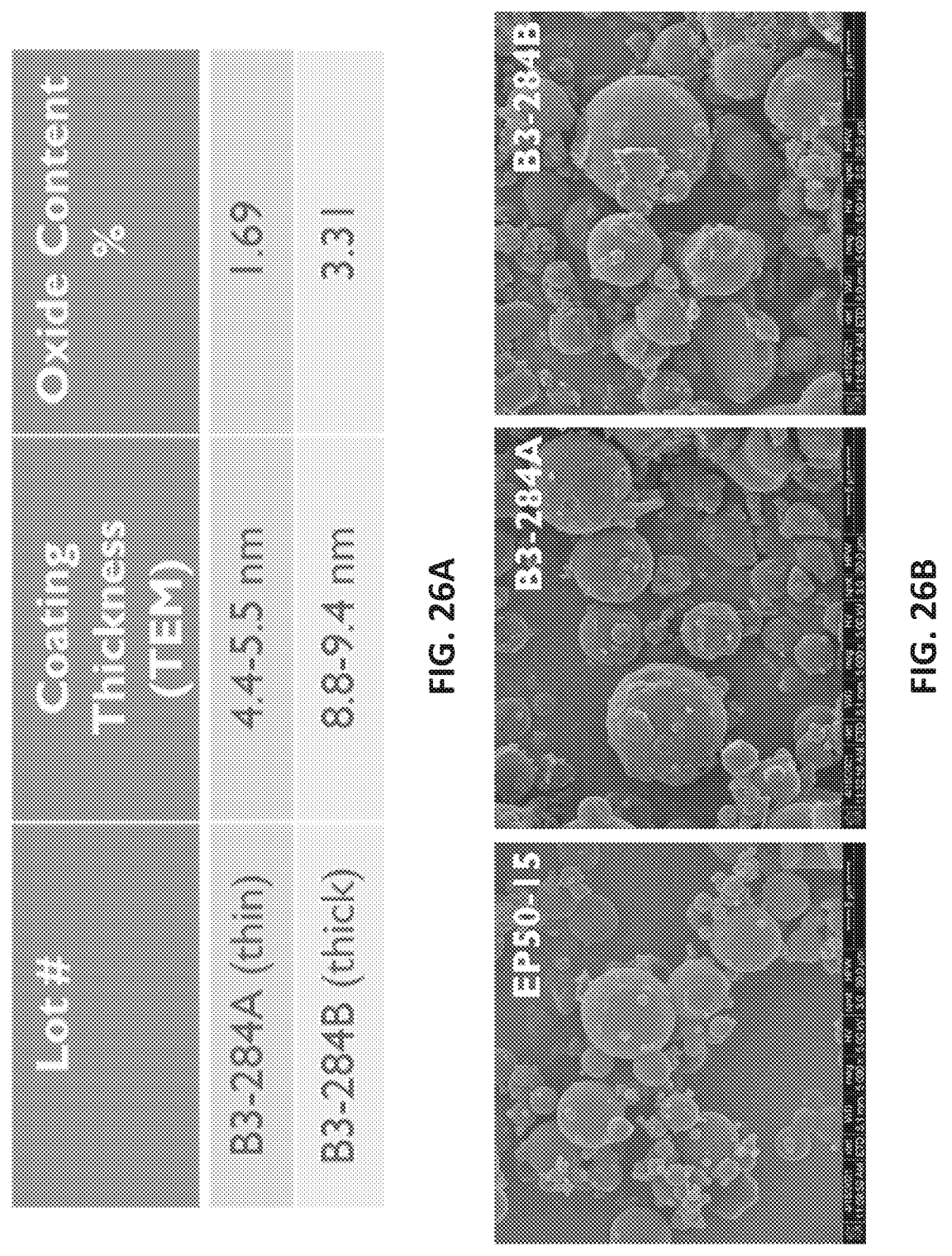
Figure 26C:
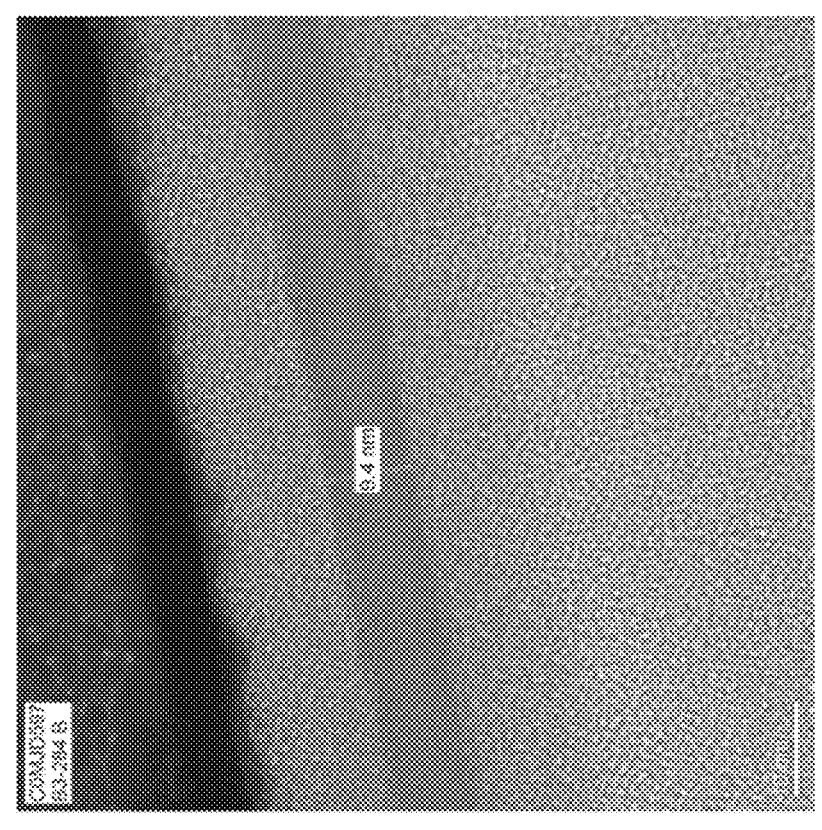
Figure 26C:
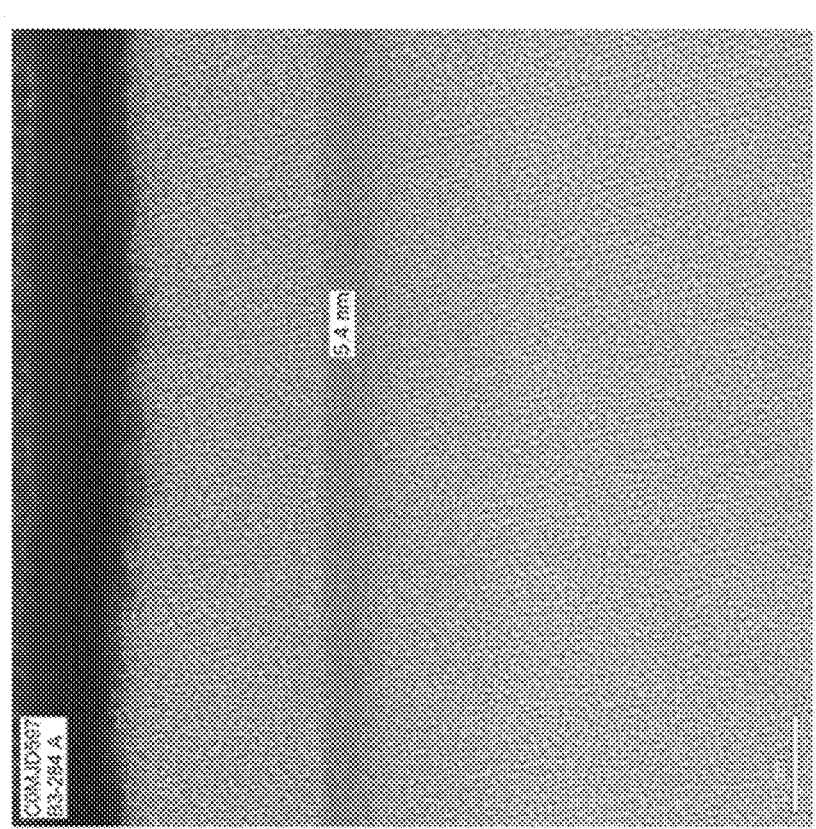

FIGS. 26A-26C depict the coating thickness, oxide content, SEM images, and TEM images of uncoated and metal oxide coated ASD particles (aluminum oxide/erlotinib/PVPVA) with 50% drug loading. FIG. 26B depicts the SEM images of the uncoated ASD (EP50-15), thin coated ASD (B3-284A) and thick coated ASD (B3-284B). FIG. 26C depicts the TEM images of the cross sections of the uncoated ASD (EP50-15).

Figure 27:
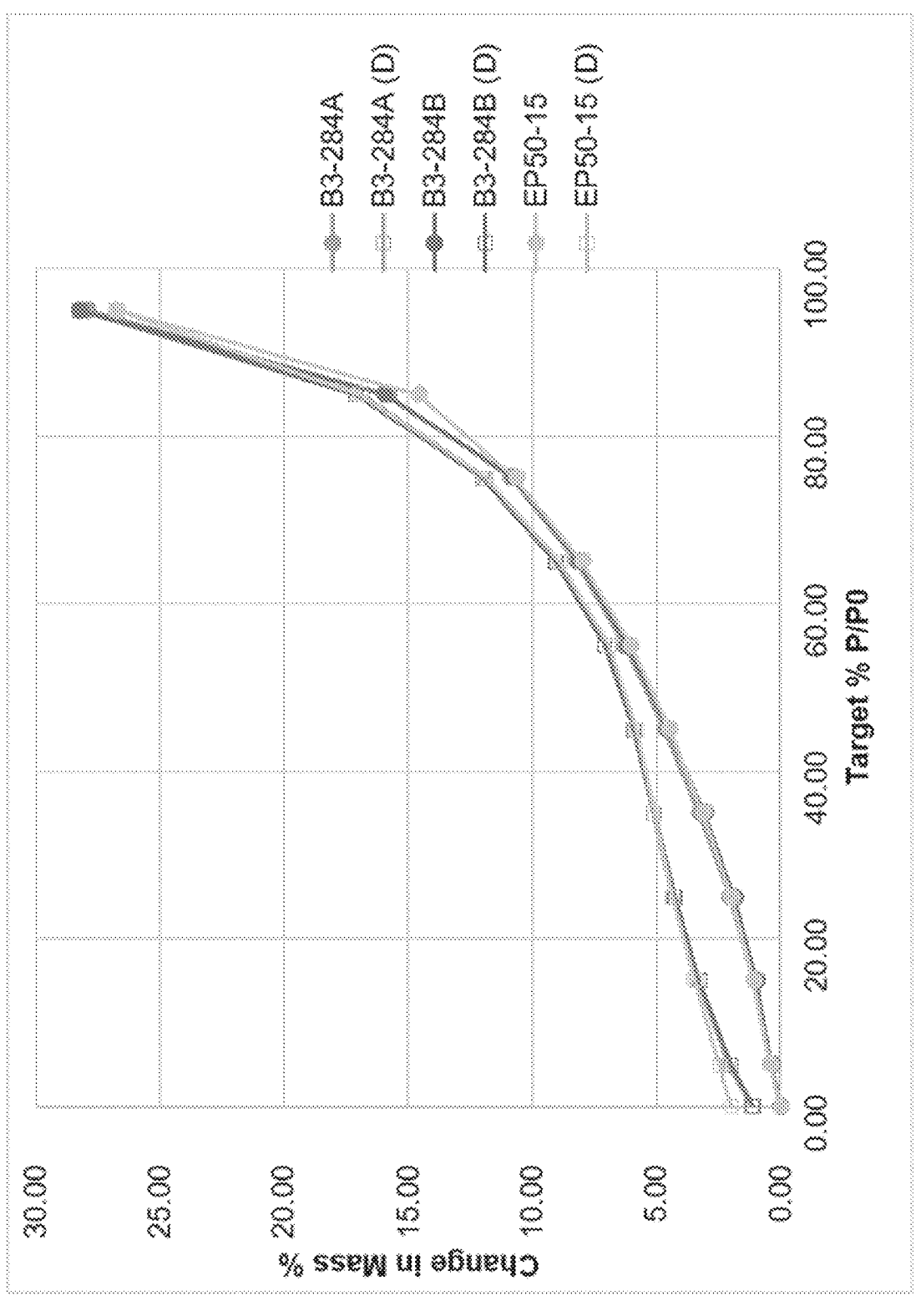

FIG. 27 depicts moisture absorption of the uncoated and metal oxide coated ASD particles (aluminum oxide/erlotinib/PVPVA) with 50% drug loading at 40° C.

Figure 28A:
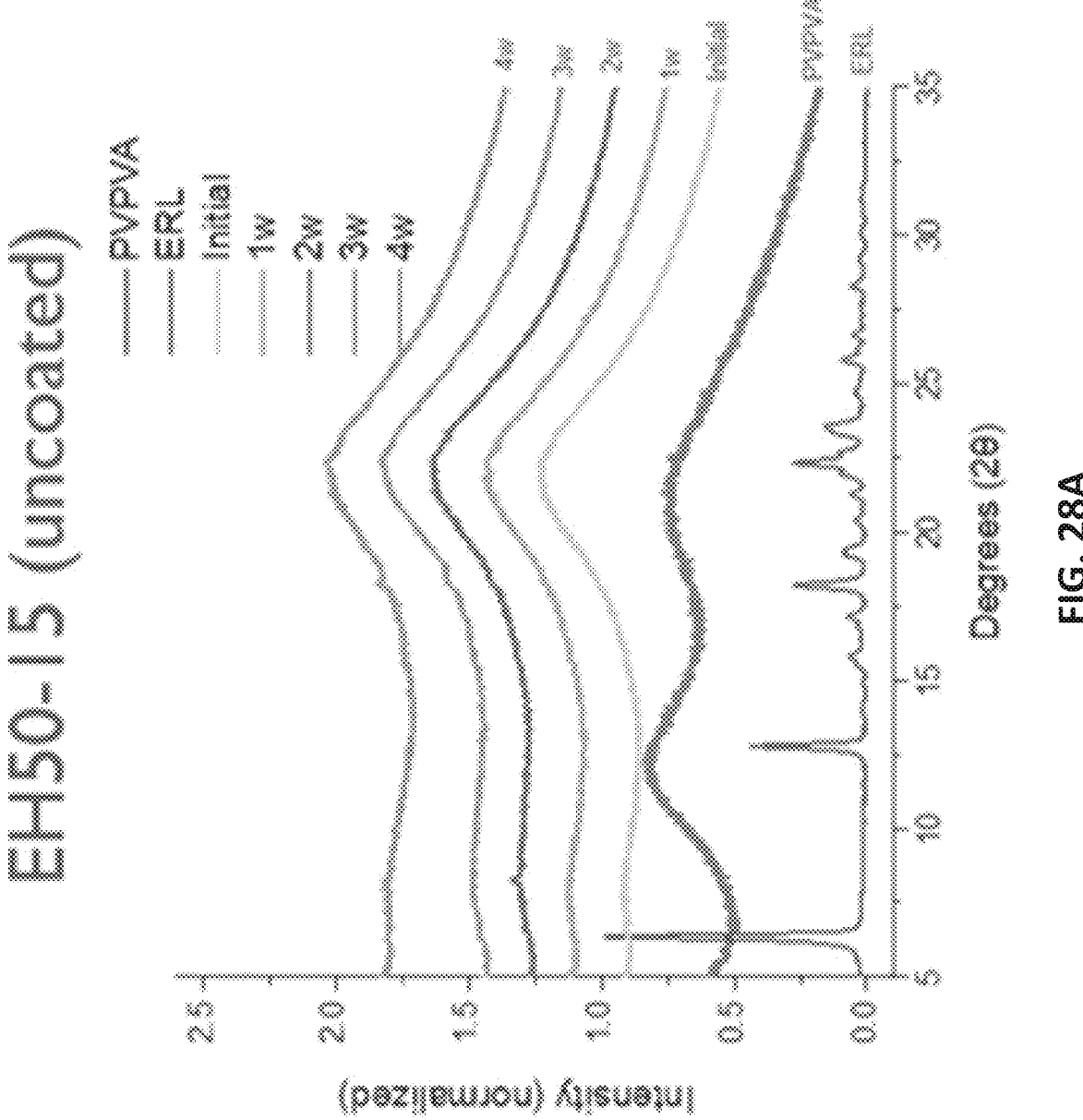
Figure 28B:
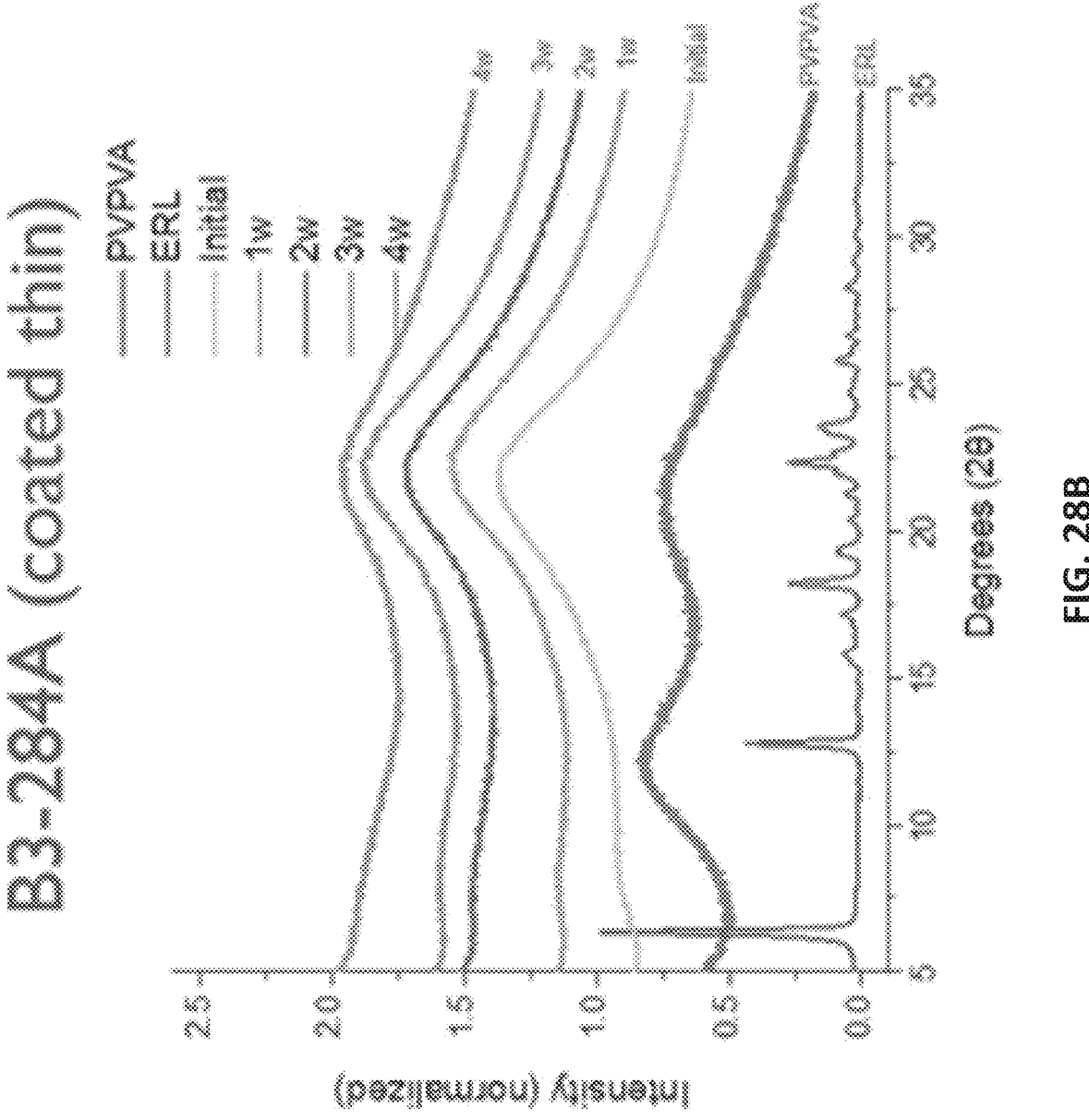
Figure 28C:
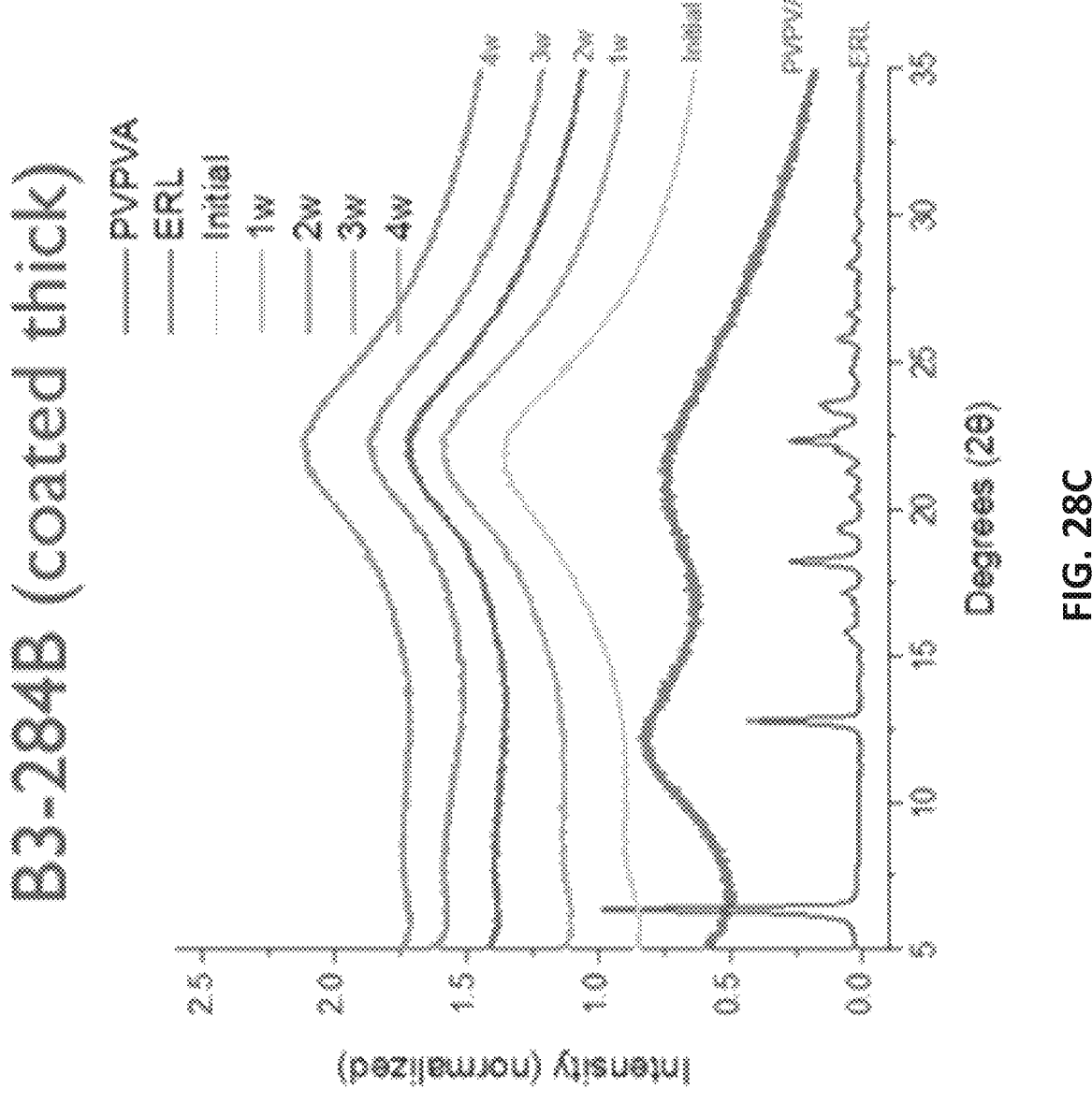

FIGS. 28A-28C depict the results of x-ray diffraction analysis of uncoated and metal oxide coated ASD particles (aluminum oxide/erlotinib/PVPVA) with 50% drug loading that were stored in capped glass bottles for 4 weeks at 40° C. and 43% relative humidity.

Figure 29A:
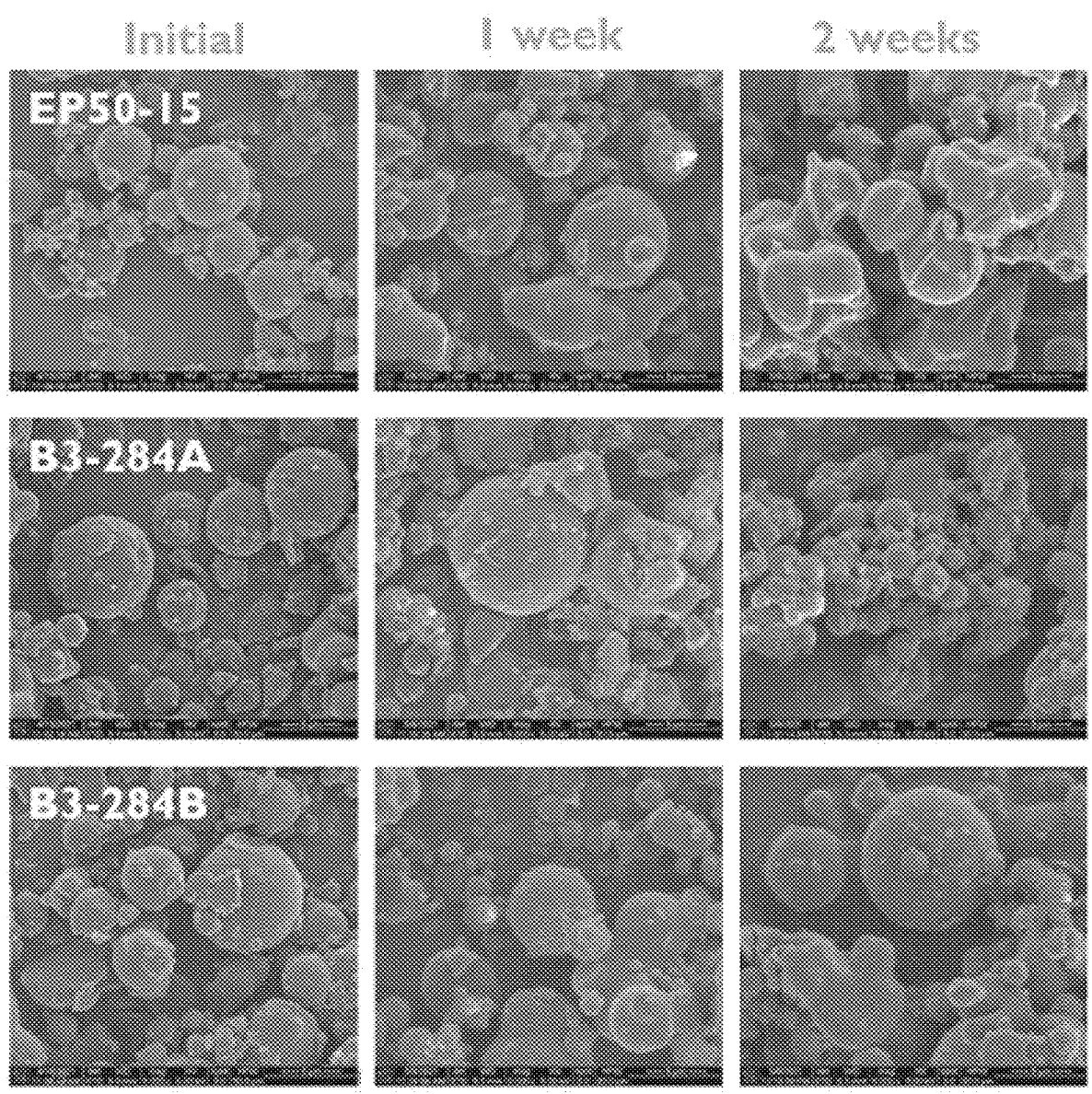
Figure 29B:
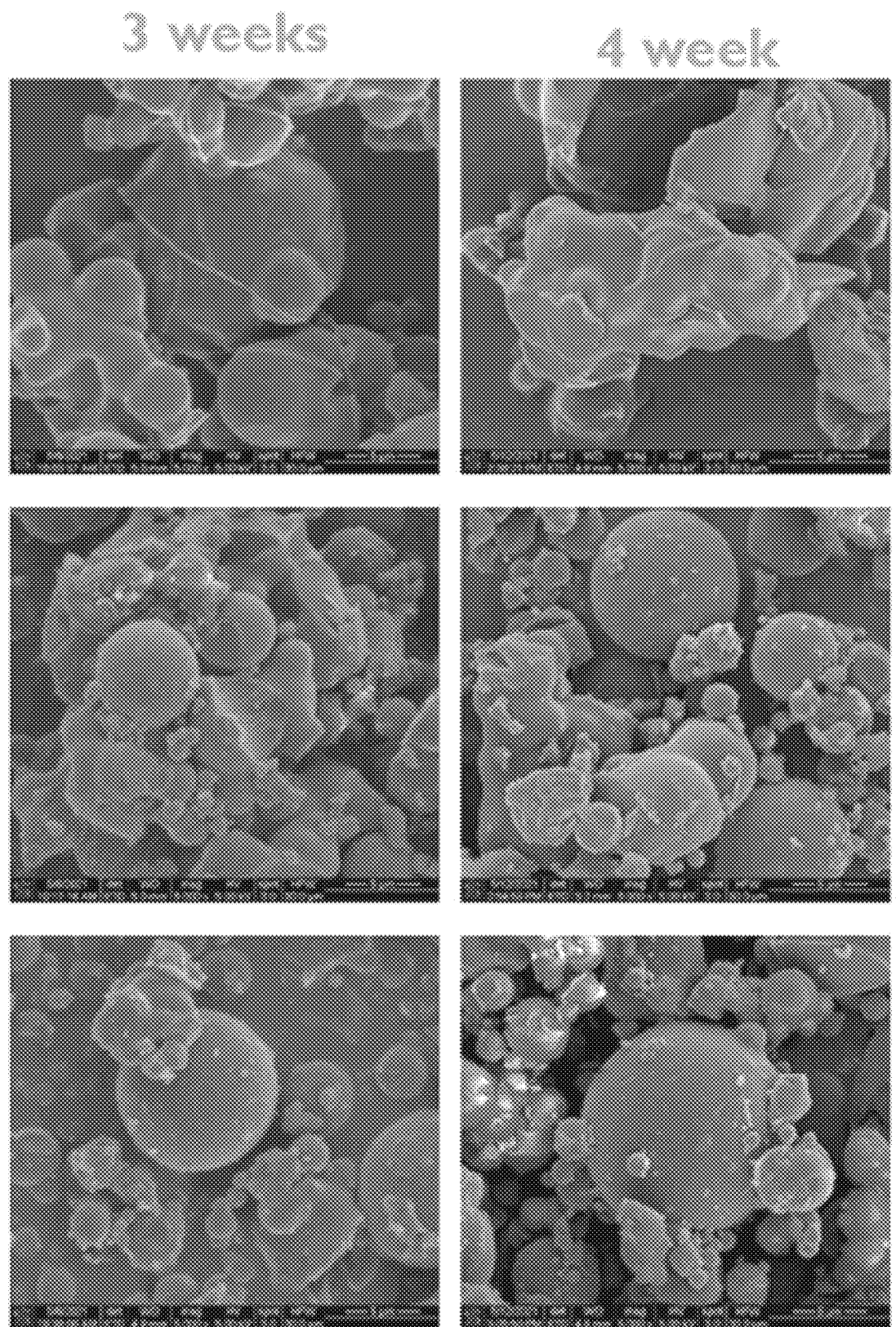

FIGS. 29A-29B depict the scanning electron microscopy images of uncoated and metal oxide coated ASD particles (aluminum oxide/erlotinib/PVPVA) with 50% drug loading that were stored in open bottles for 4 weeks at 40° C. and 43% relative humidity.

Figure 30B:
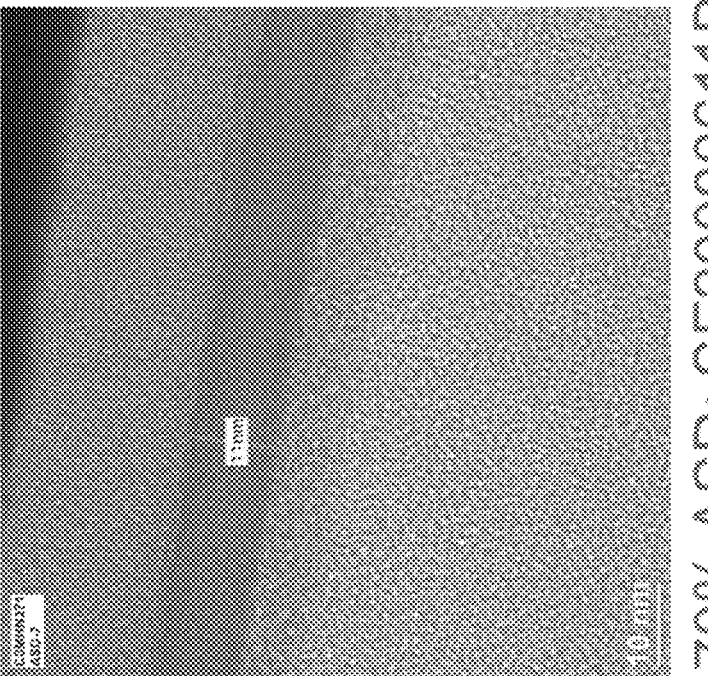
Figure 30B:
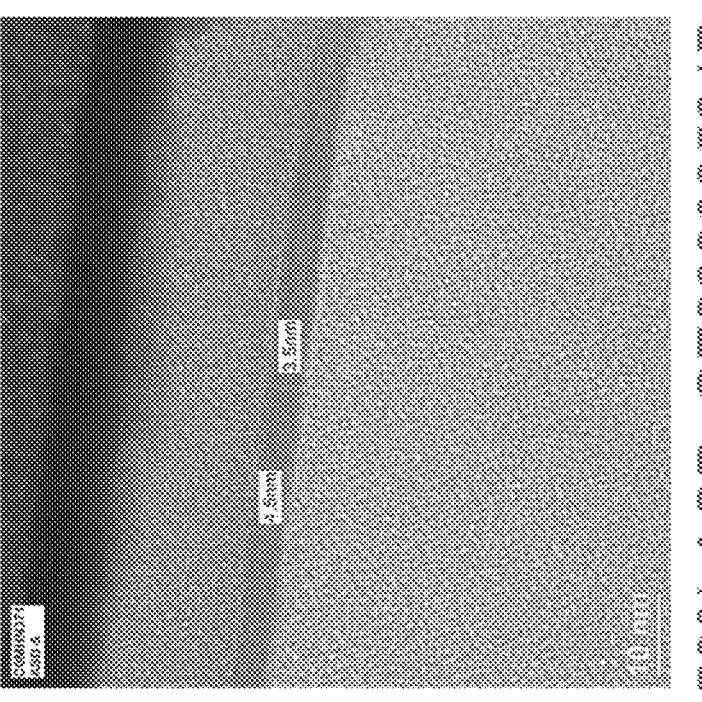

FIGS. 30A-30B depict the assay of nifedipine and water content (FIG. 30A) and TEM images (FIG. 30B) of the various uncoated and metal oxide coated ASD particles (aluminum oxide/Nifedipine/PVP) with 50% (SF20000521) and 70% (SF20000611) drug loading as freshly prepared. FIG. 30B depicts TEM images of cross sections of coated 50% and 70% DL ASD particles.

Figure 31:
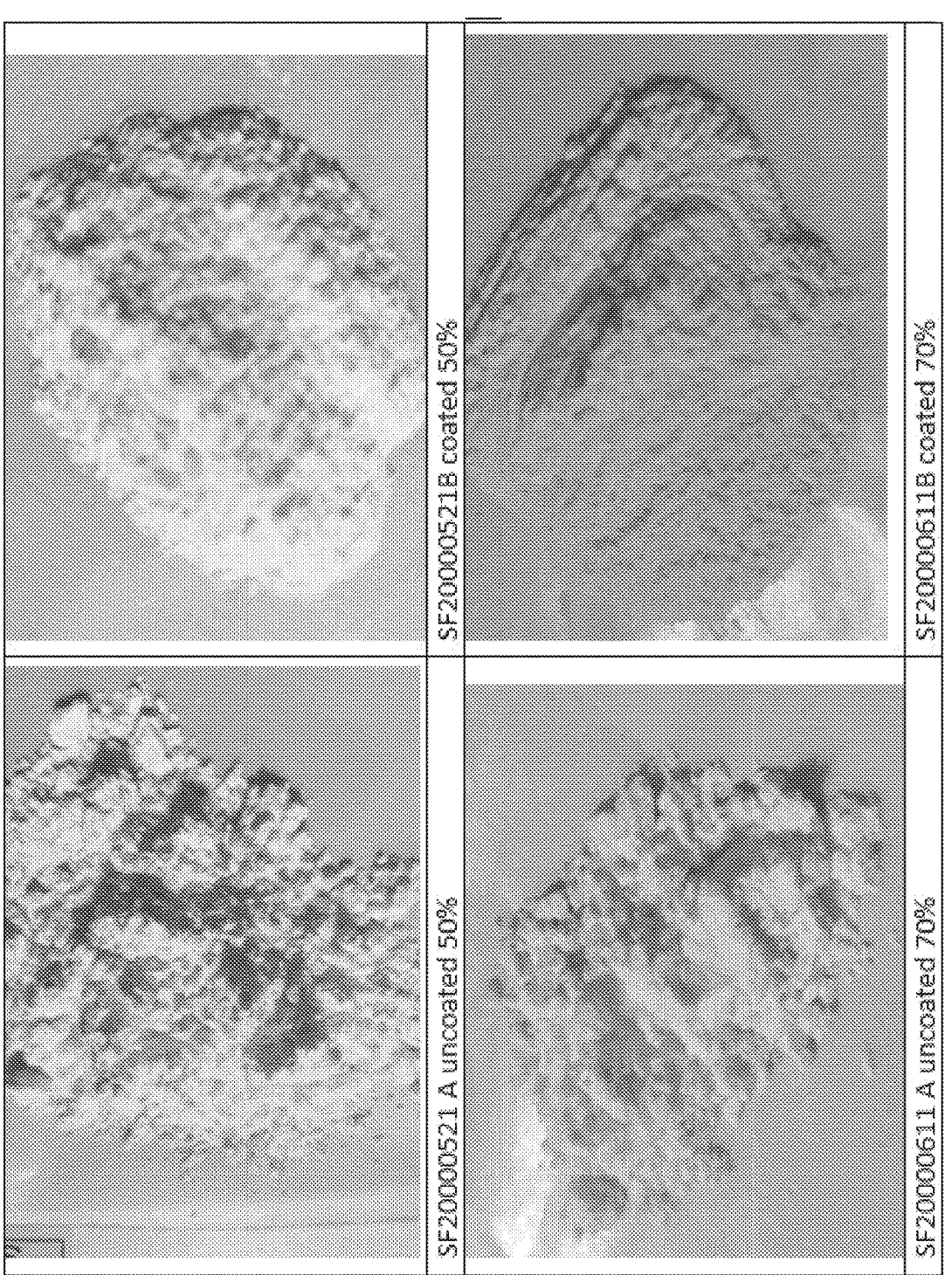
Figure 32A:
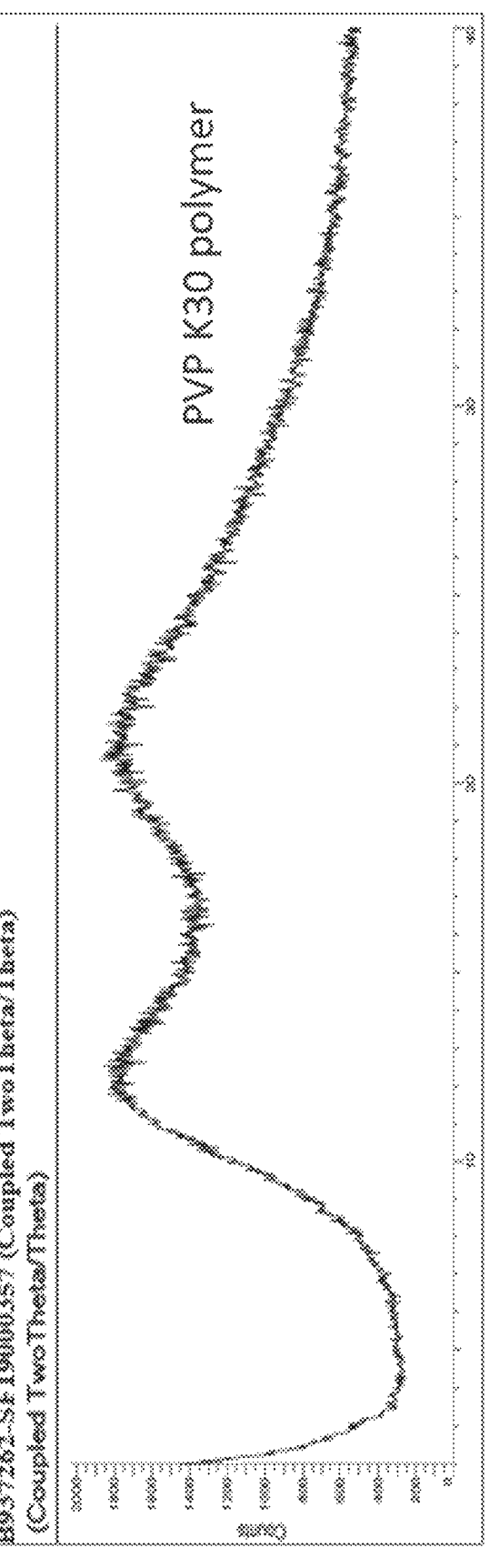
Figure 32B:
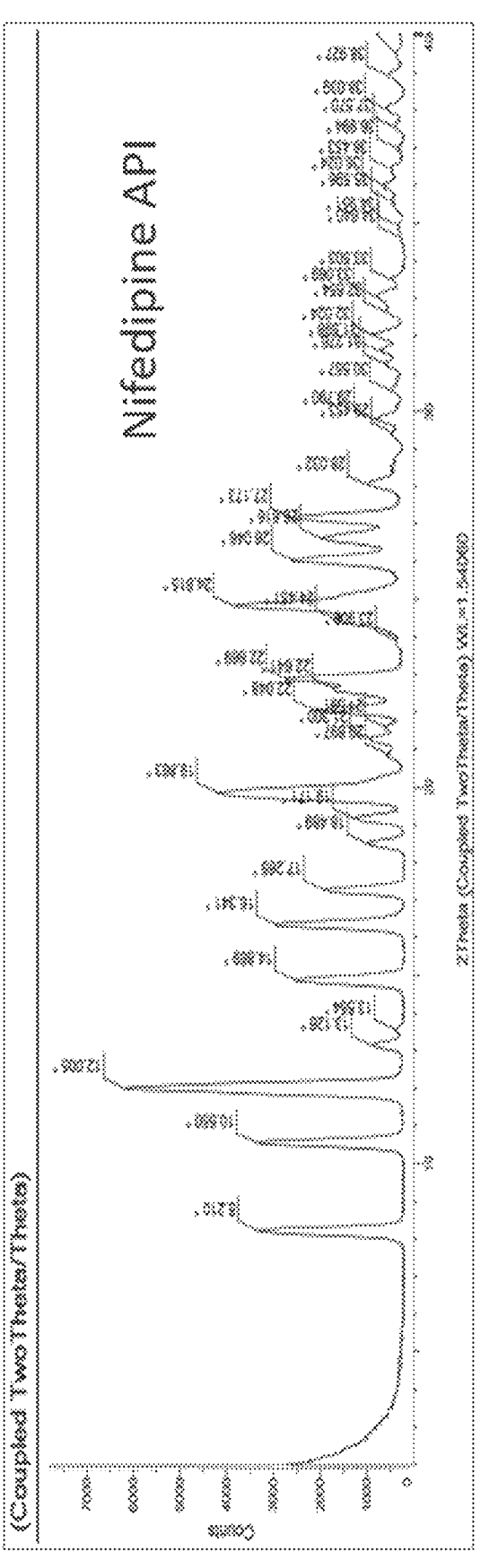
Figure 32C:
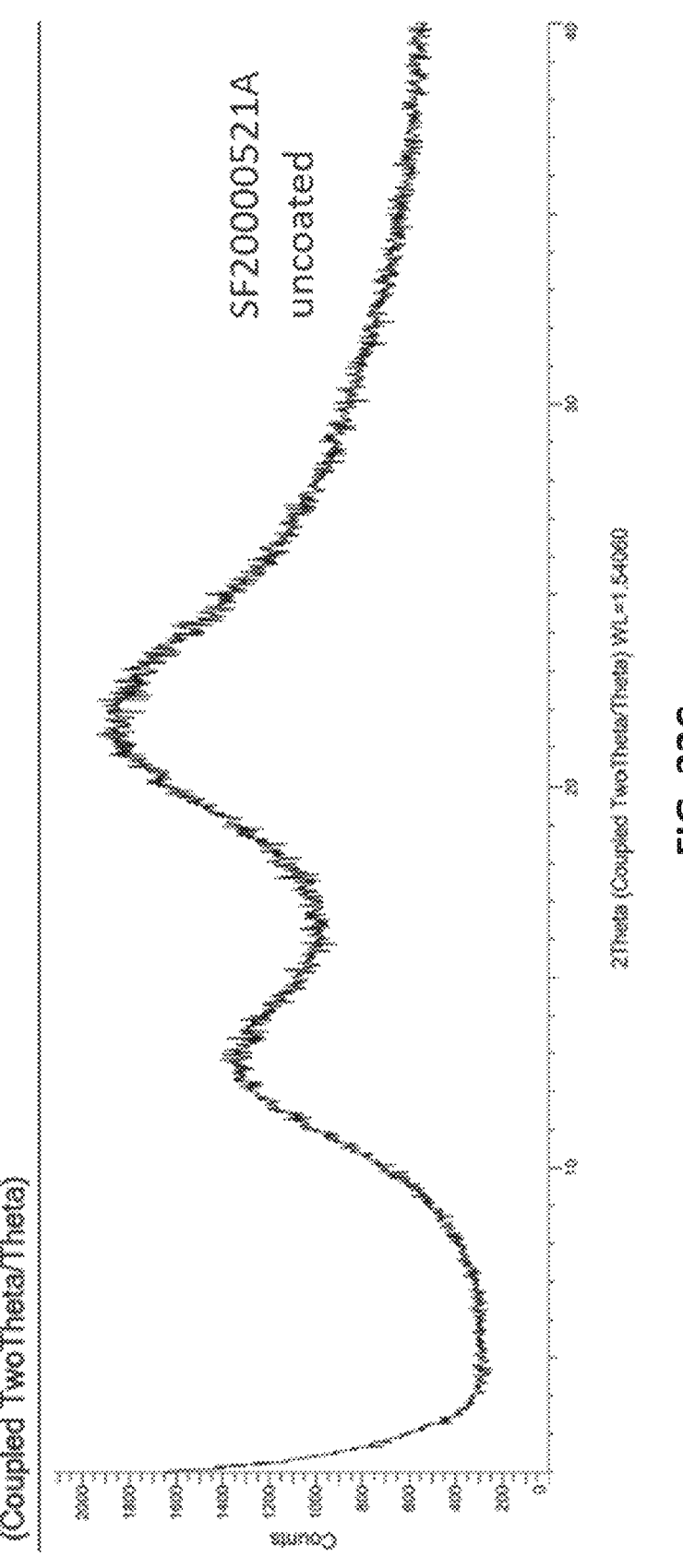
Figure 32D:
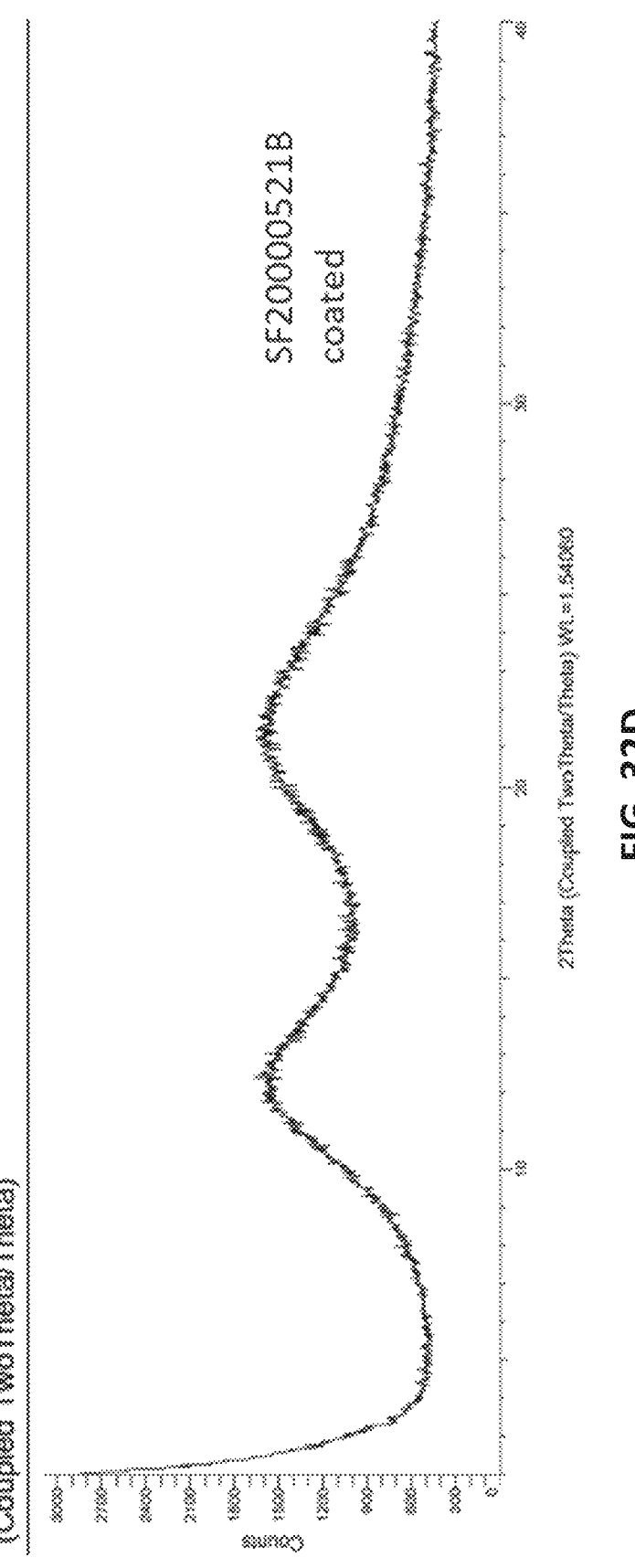
Figure 32E:
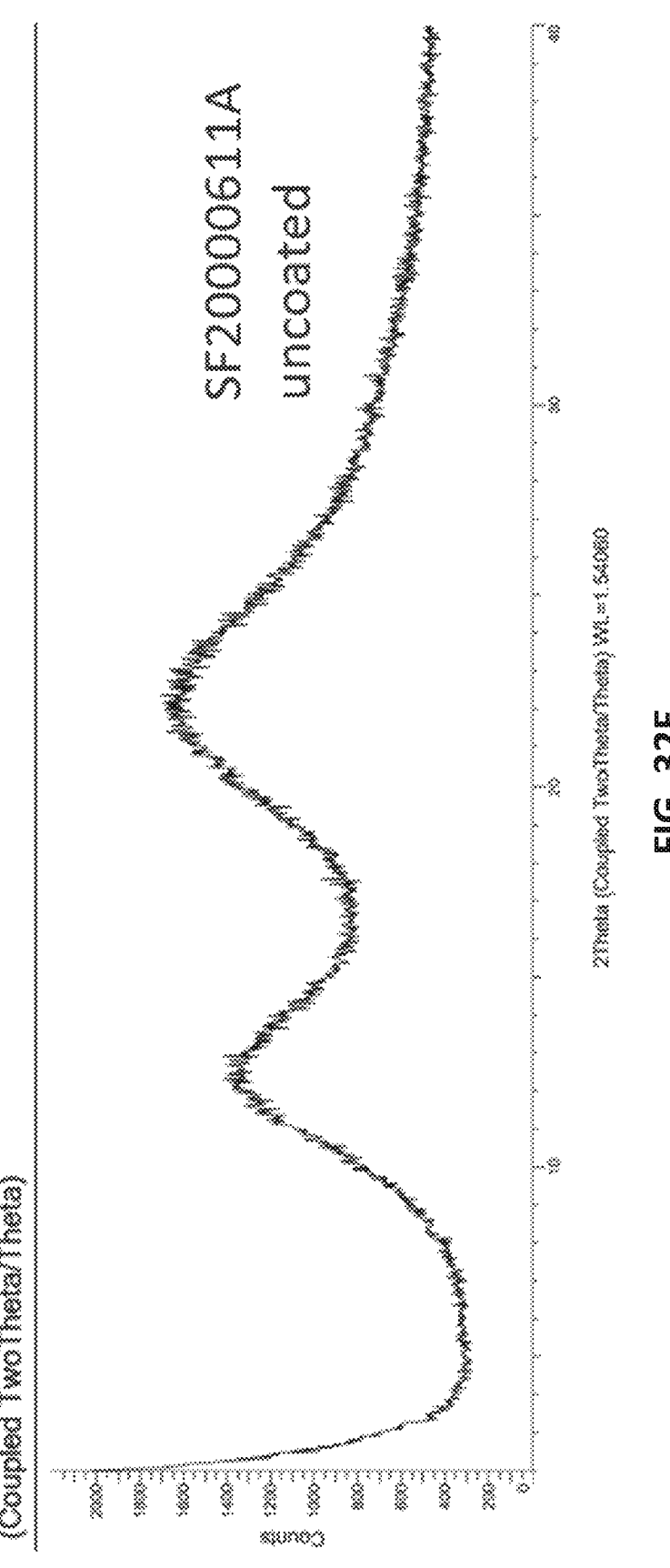
Figure 32F:
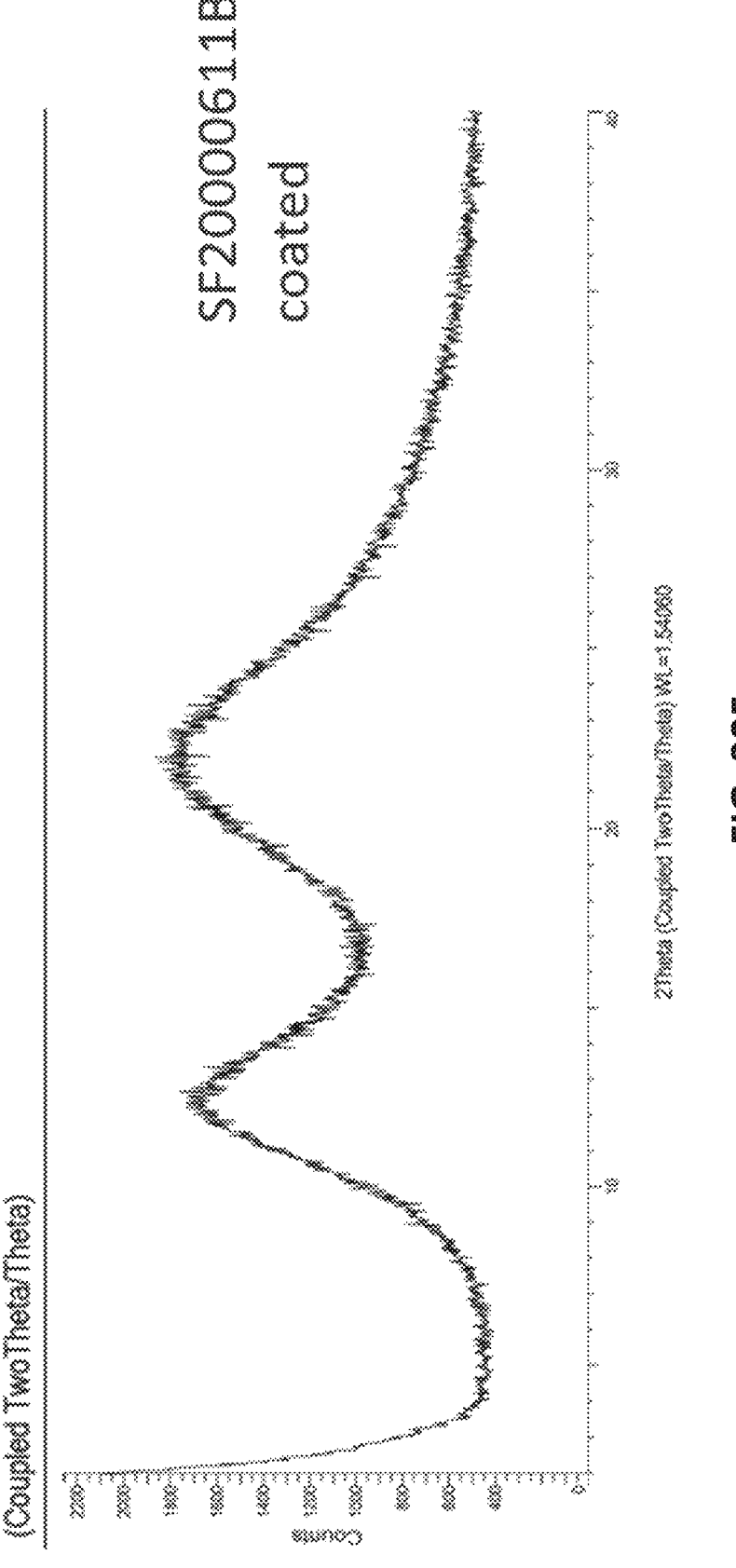

FIG. 31 depicts the appearance of the freshly prepared uncoated and metal oxide coated ASD particles (aluminum oxide/Nifedipine/PVP) with 50% (SF20000521) and 70% (SF20000611) drug loading.

FIGS. 32A-32F depict the results of x-ray diffraction analysis of PVP, nifedipine, uncoated and metal oxide coated ASD particles (aluminum oxide/Nifedipine/PVP) with 50% (SF20000521) and 70% (SF20000611) drug loading.

FIGS. 33A-33D depict the assay, moisture sorption and impurity analysis of uncoated and metal oxide coated ASD particles (aluminum oxide/Nifedipine/PVP) with 50% (SF20000521) and 70% (SF20000611) drug loading that were stored in capped amber glass bottles, capped with induction sealed HDPE bottles, or open HDPE bottles with no cap.

Figure 34A:
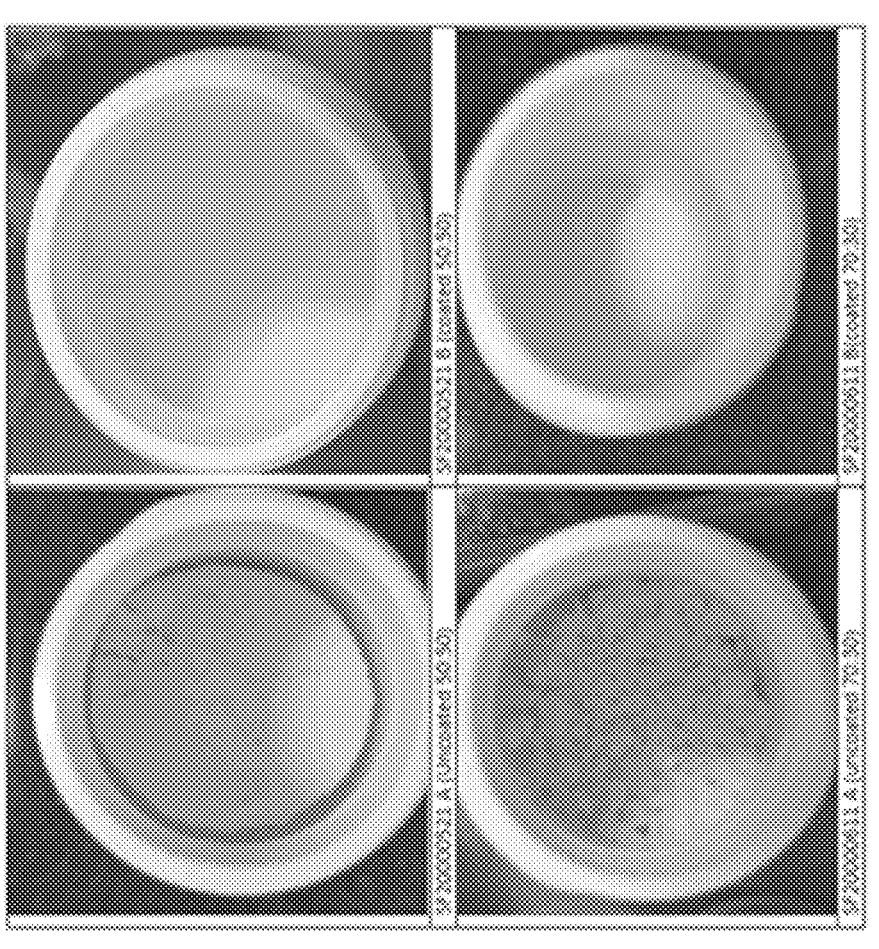
Figure 34B:
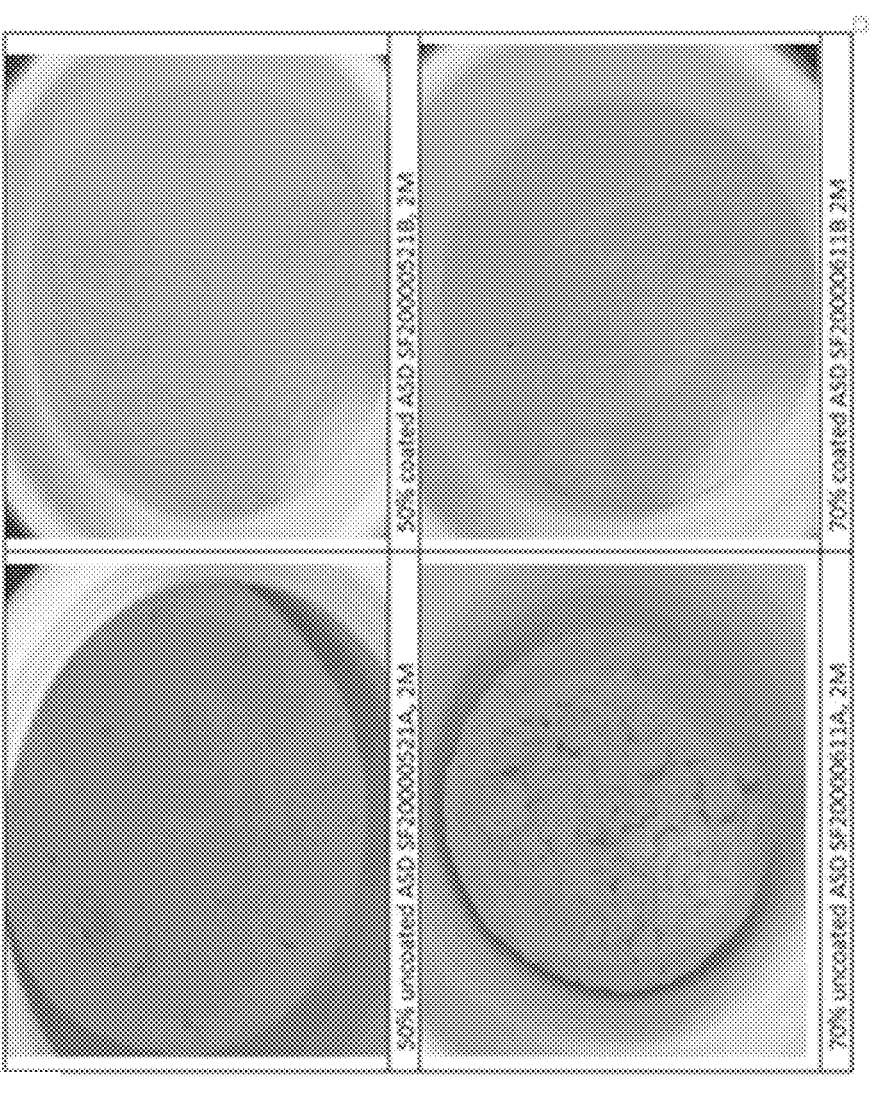
Figure 34C:
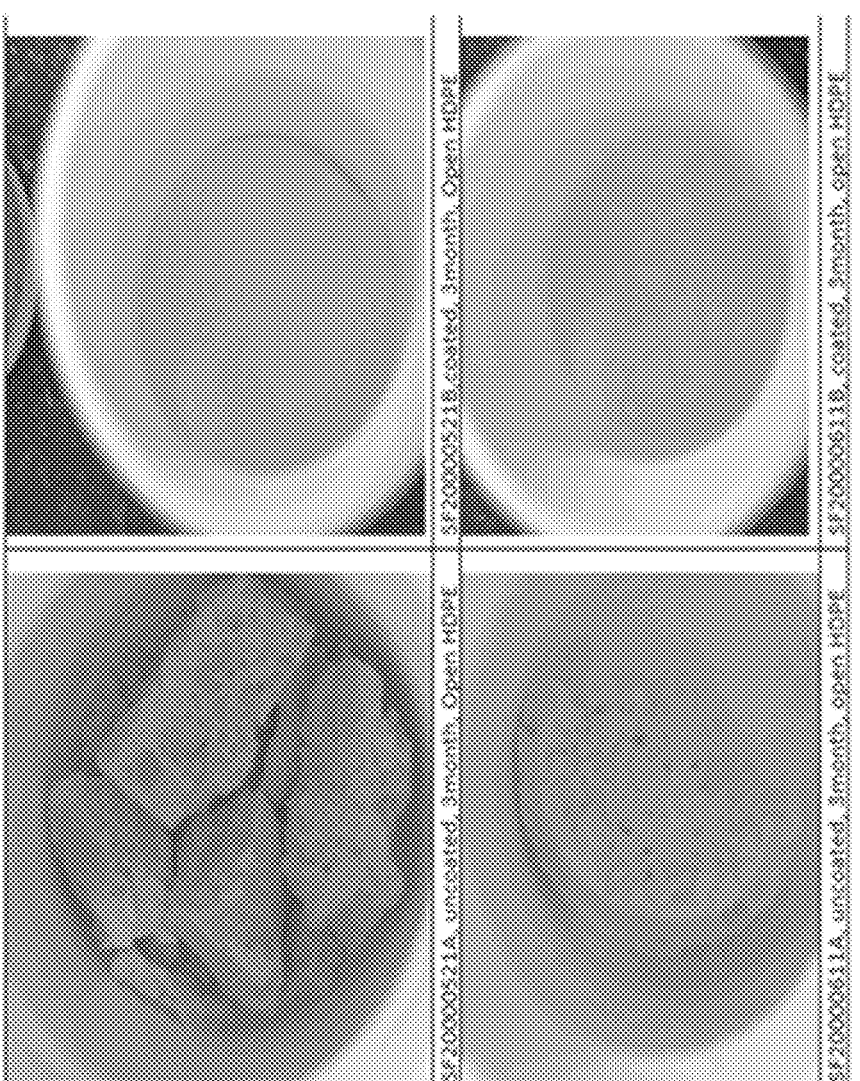
Figure 34C:

FIGS. 34A-34C depict the appearance of the uncoated and metal oxide coated ASD particles (aluminum oxide/Nifedipine/PVP) with 50% (SF20000521) and 70% (SF20000611) drug loading that were stored in open HDPE bottles with no cap for various durations at 40° C. and 75% relative humidity.

Figure 35A:
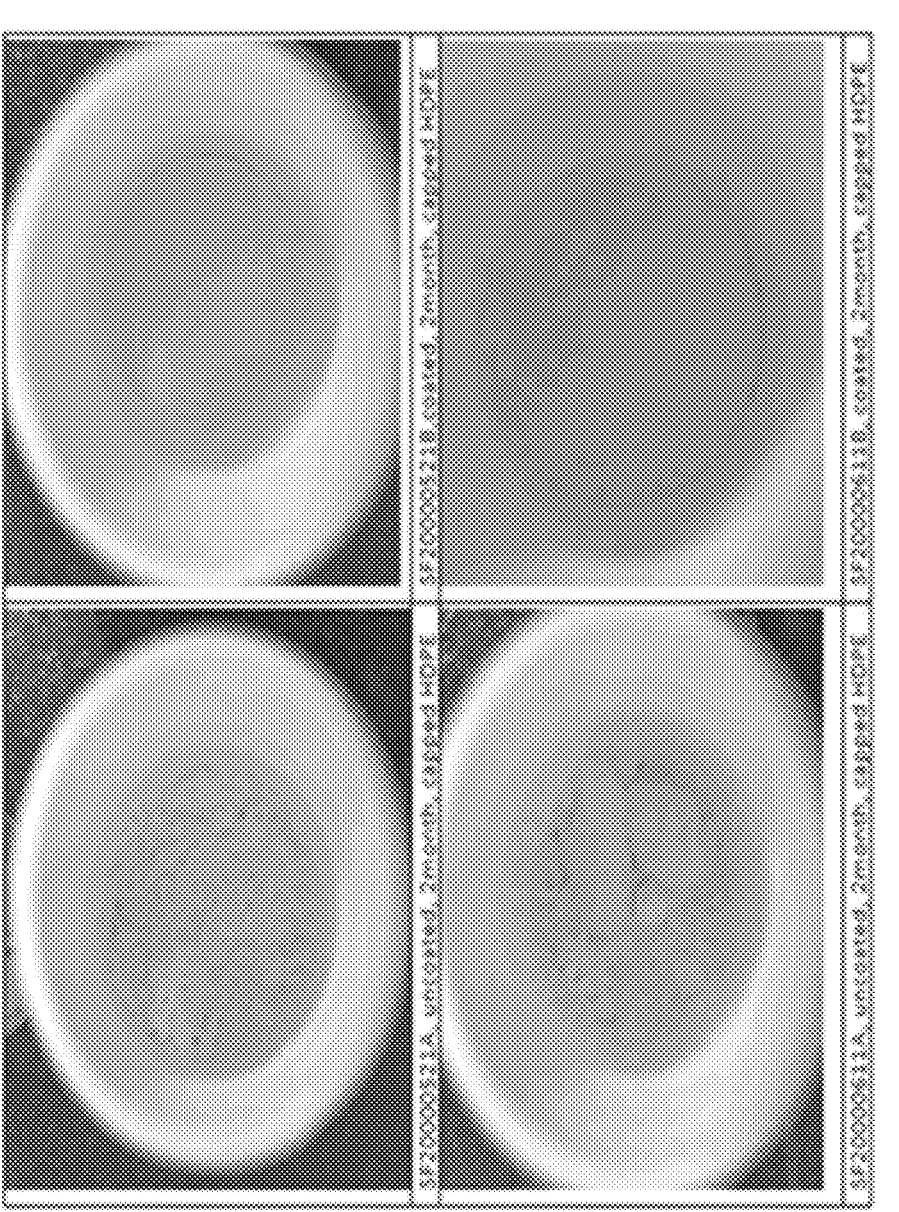
Figure 35B:
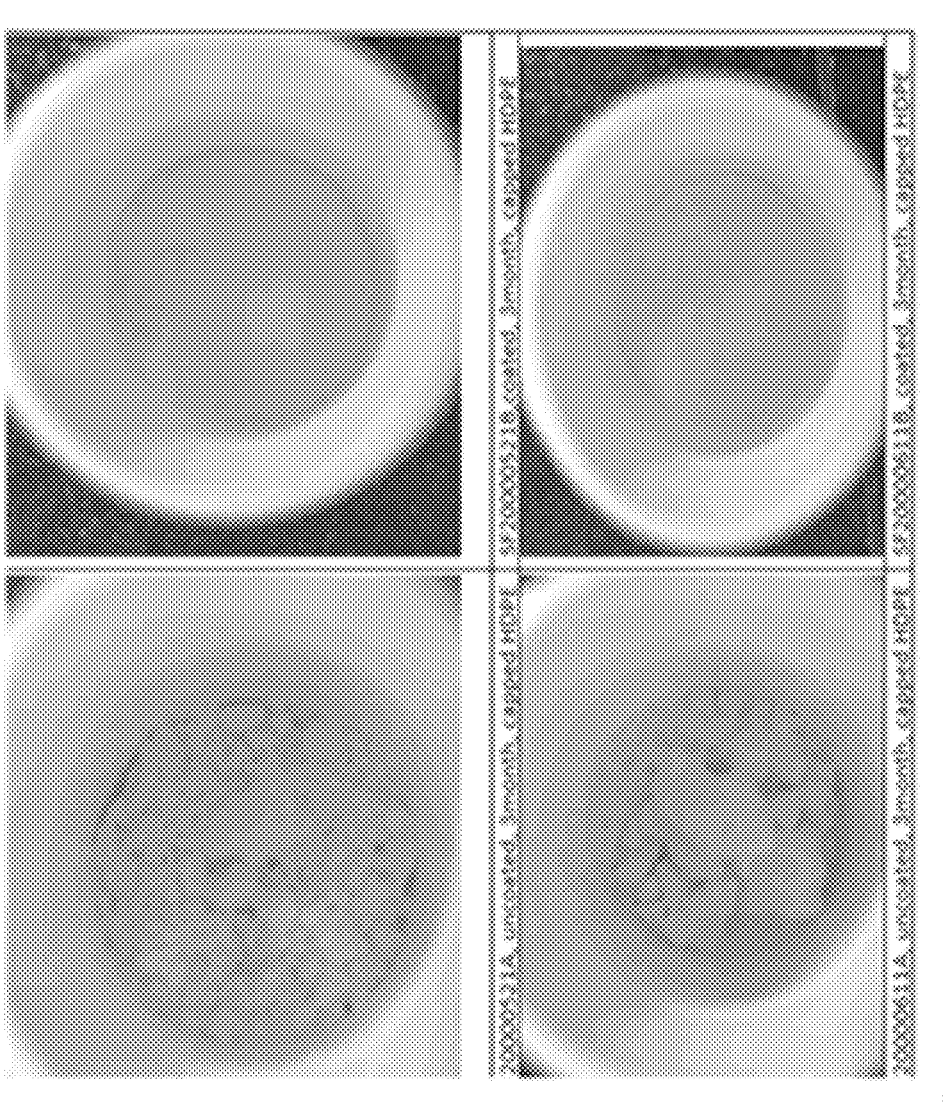
Figure 35C:
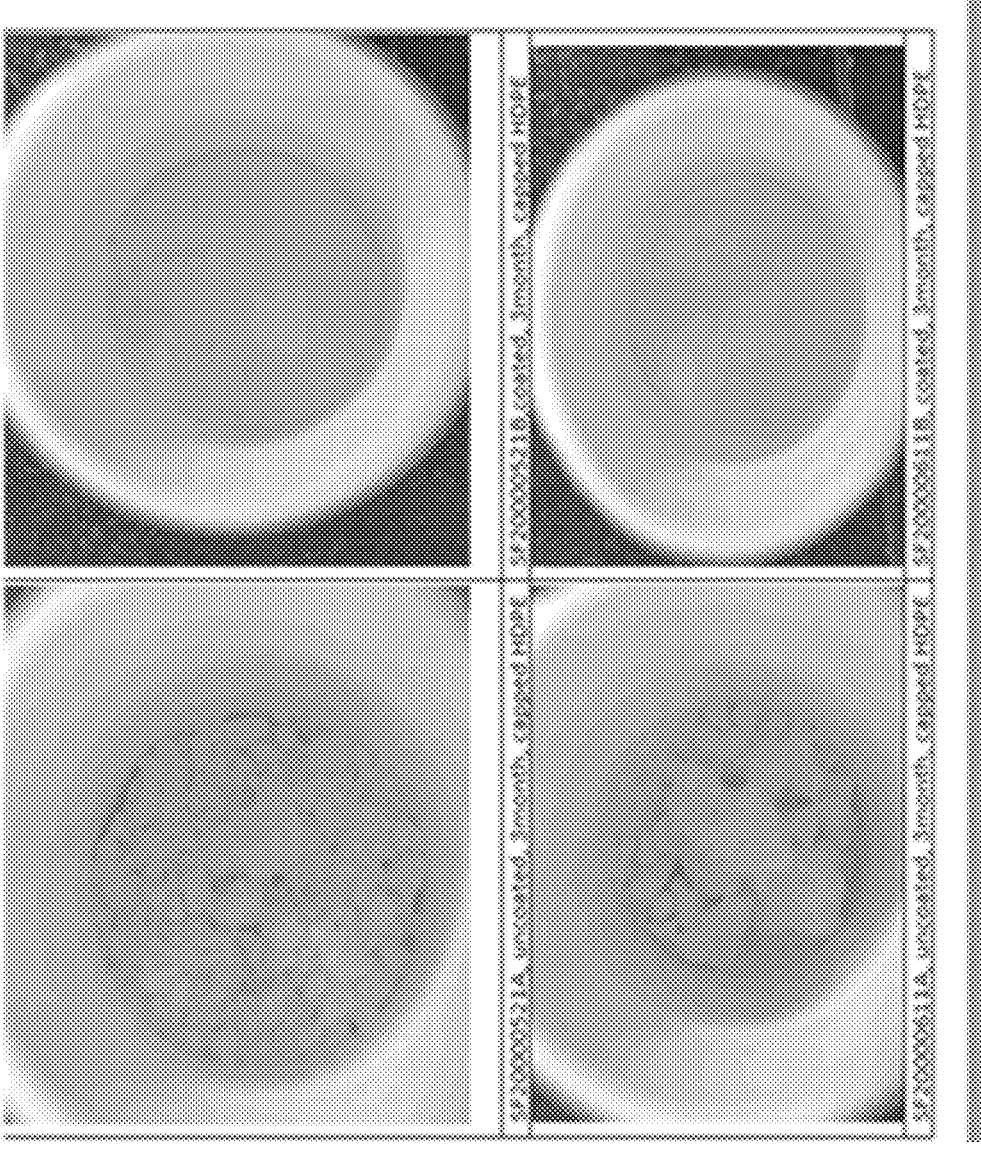

FIGS. 35A-35C depict the appearance of the uncoated and metal oxide coated ASD particles (aluminum oxide/Nifedipine/PVP) with 50% (SF20000521) and 70% (SF20000611) drug loading that were stored in capped with induction sealed HDPE bottles for various durations.

Figure 36A:
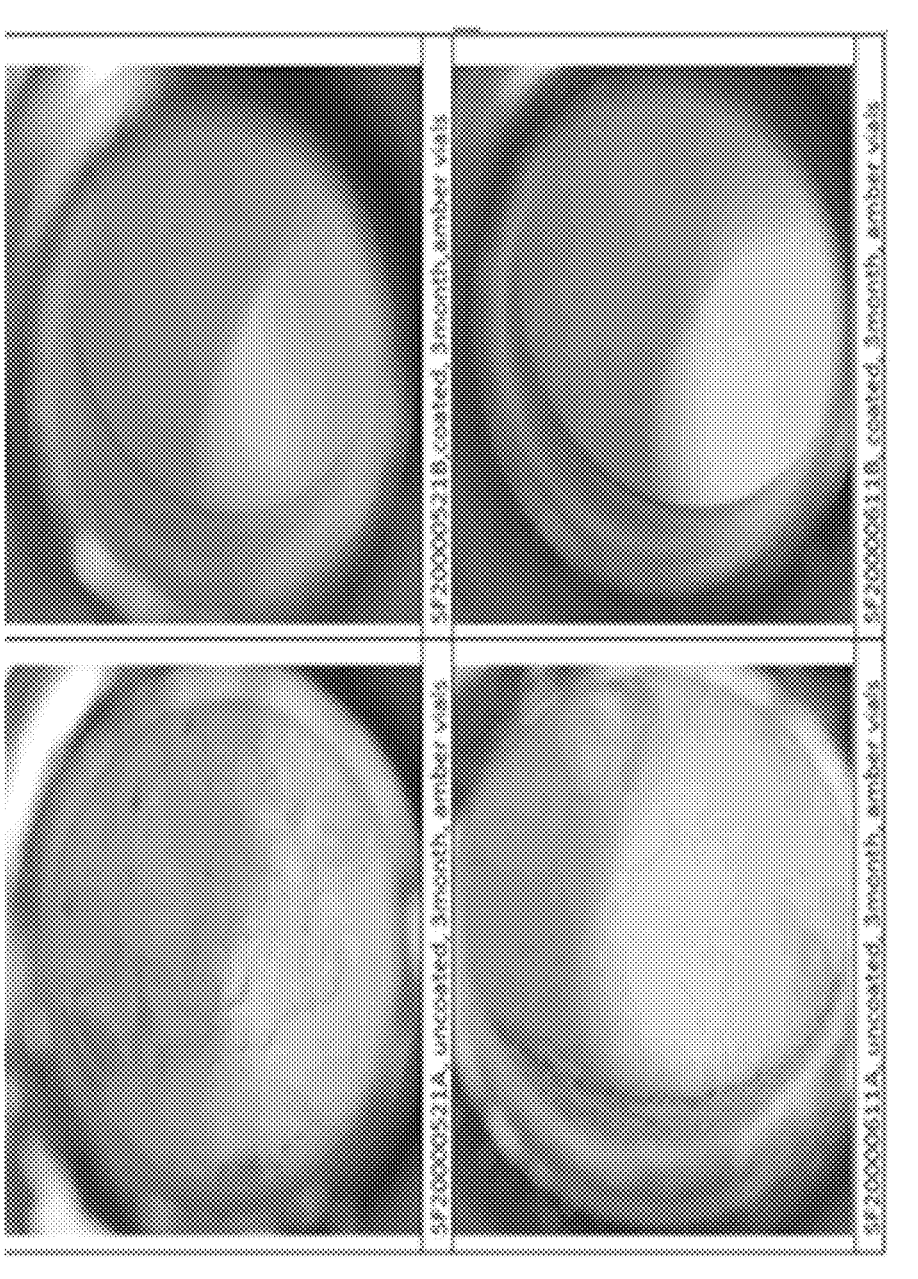
Figure 36B:
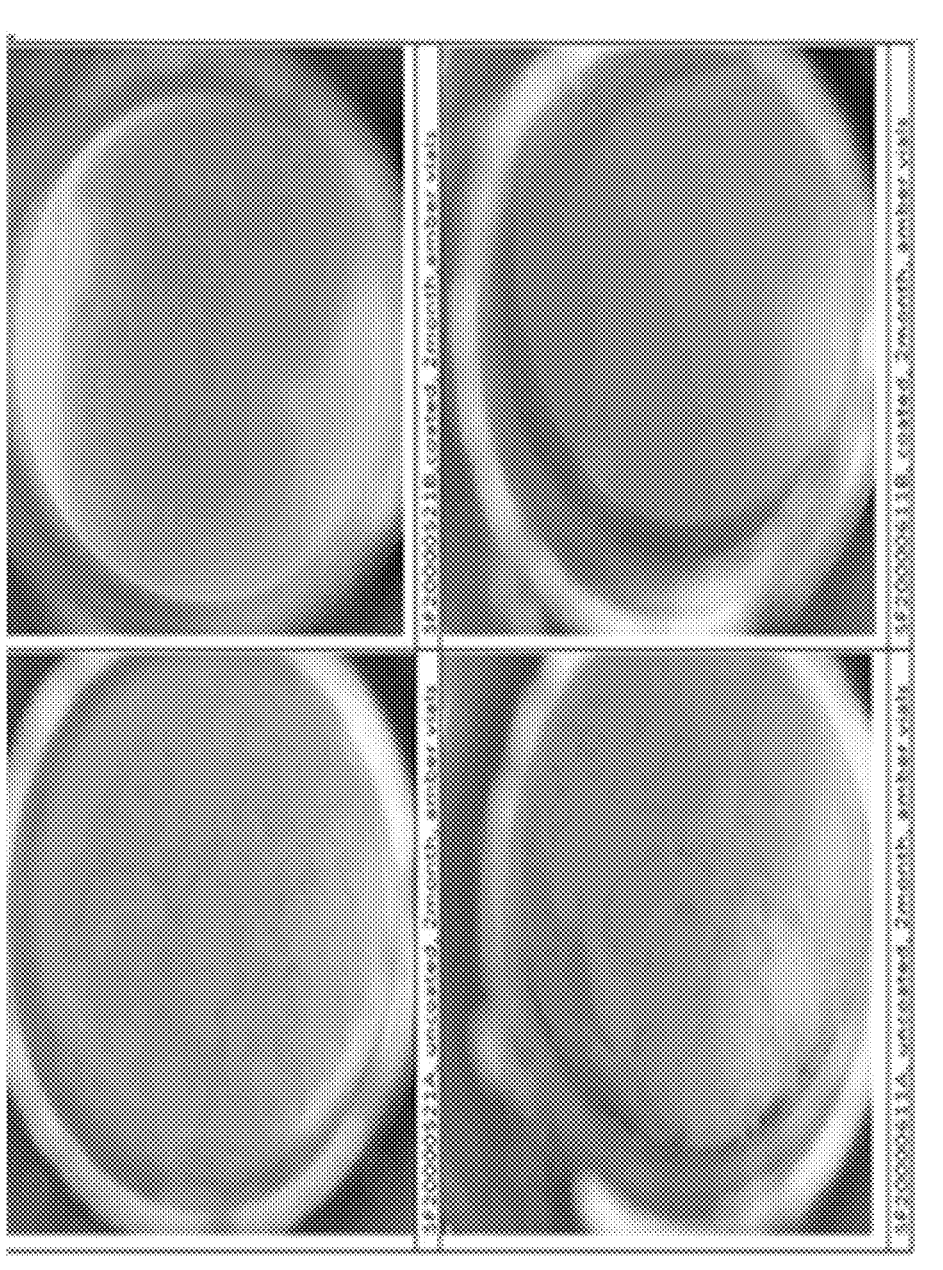
Figure 36C:
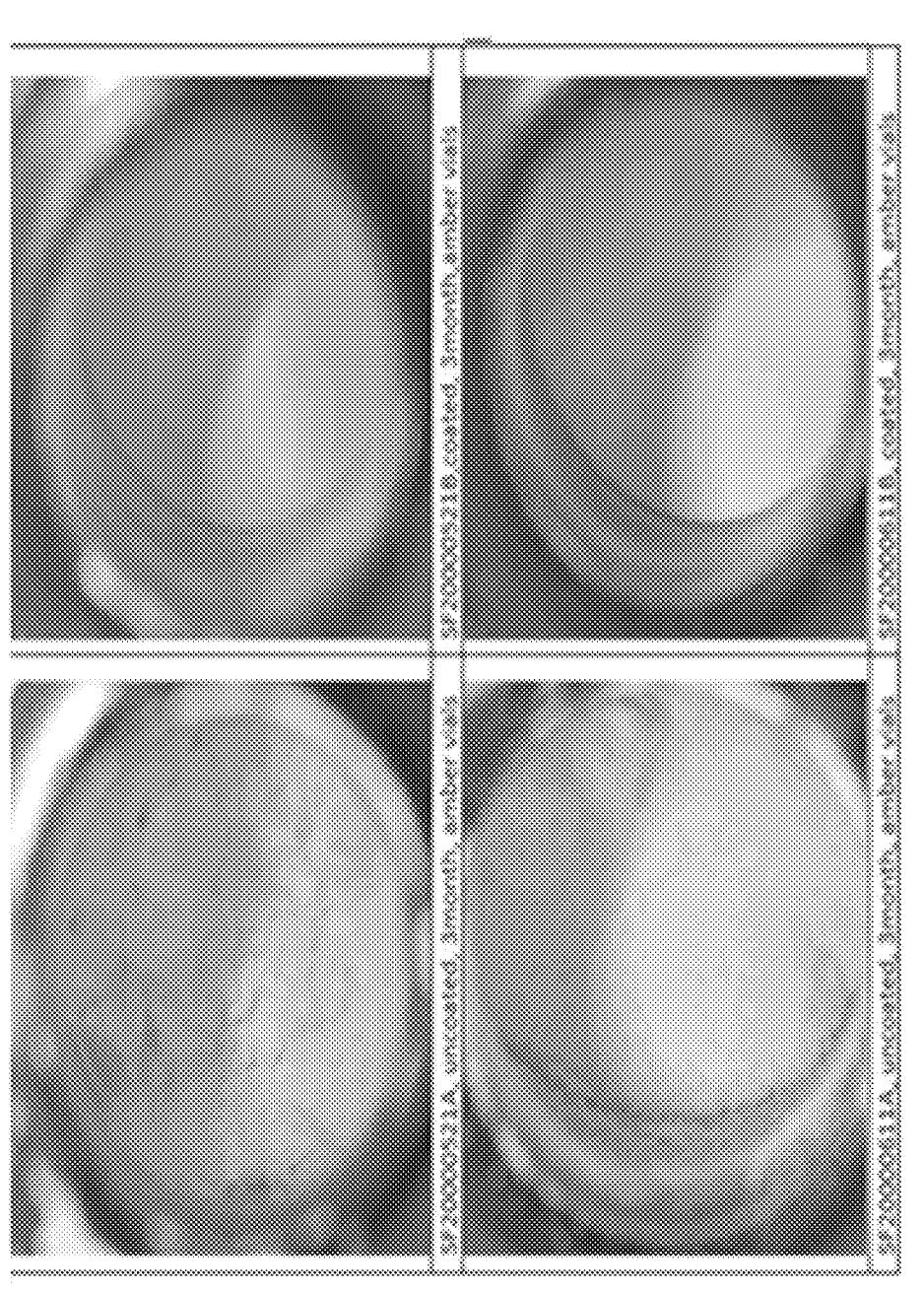
Figure 37A:
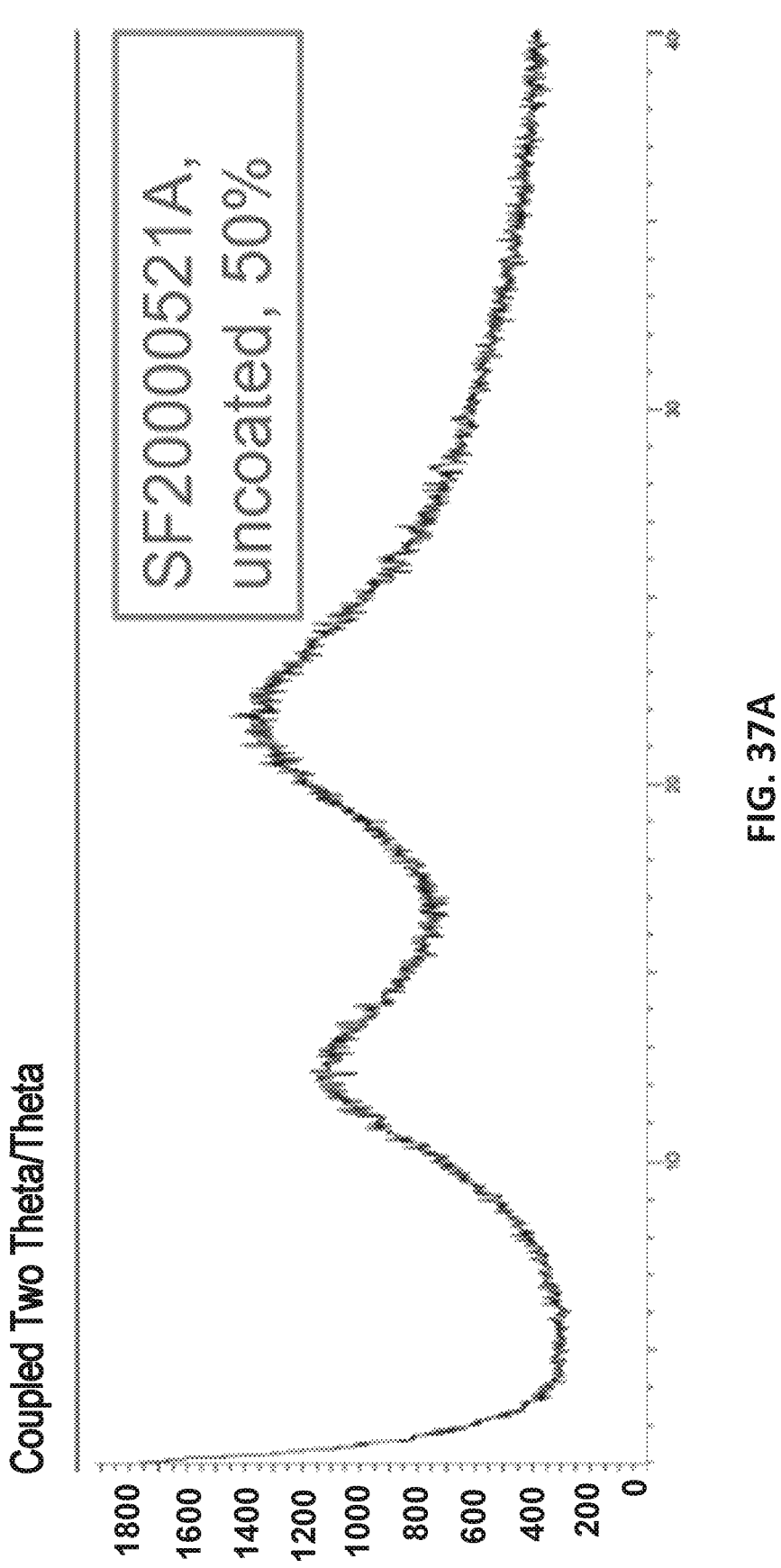
Figure 37B:
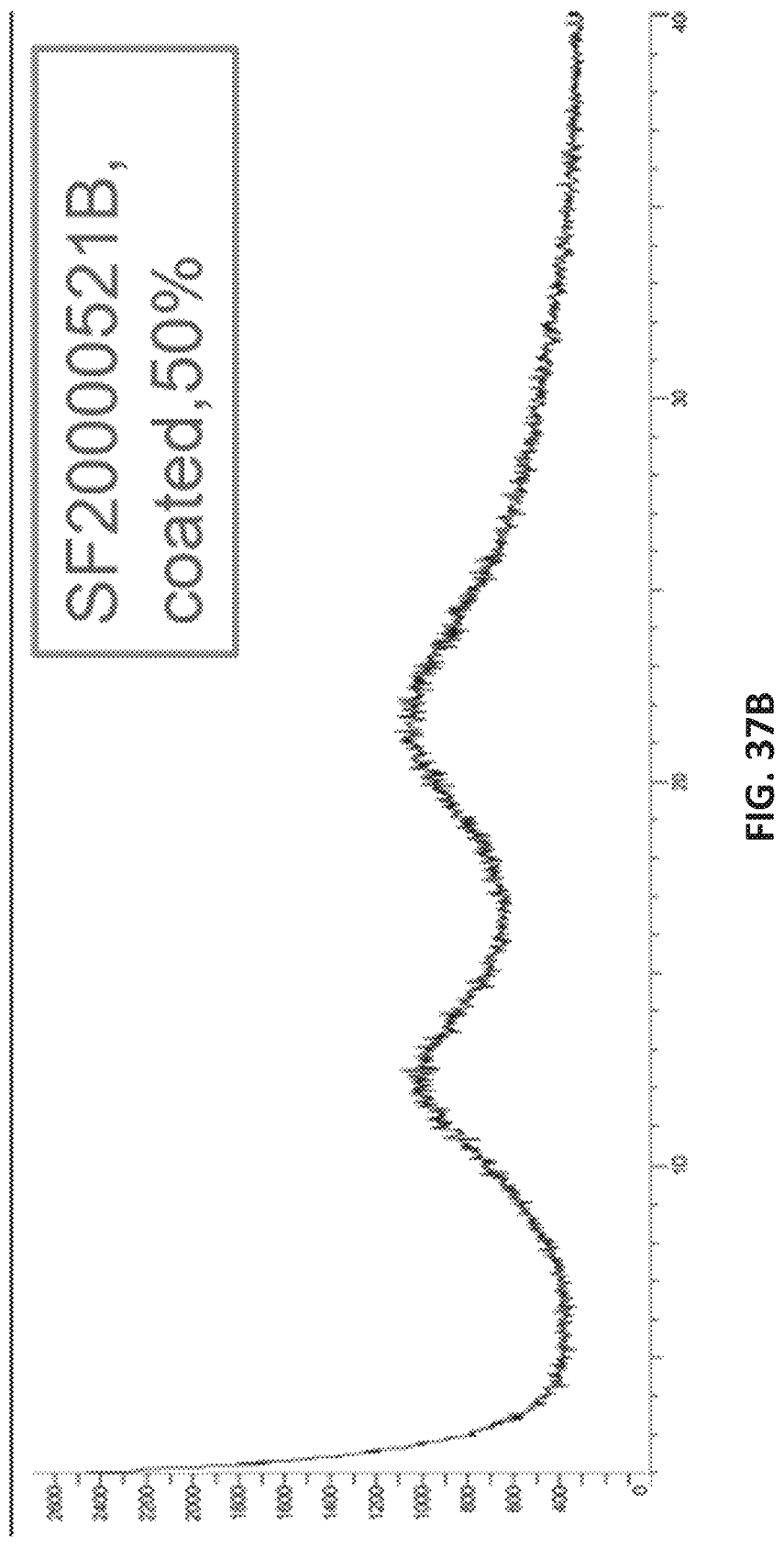
Figure 37C:
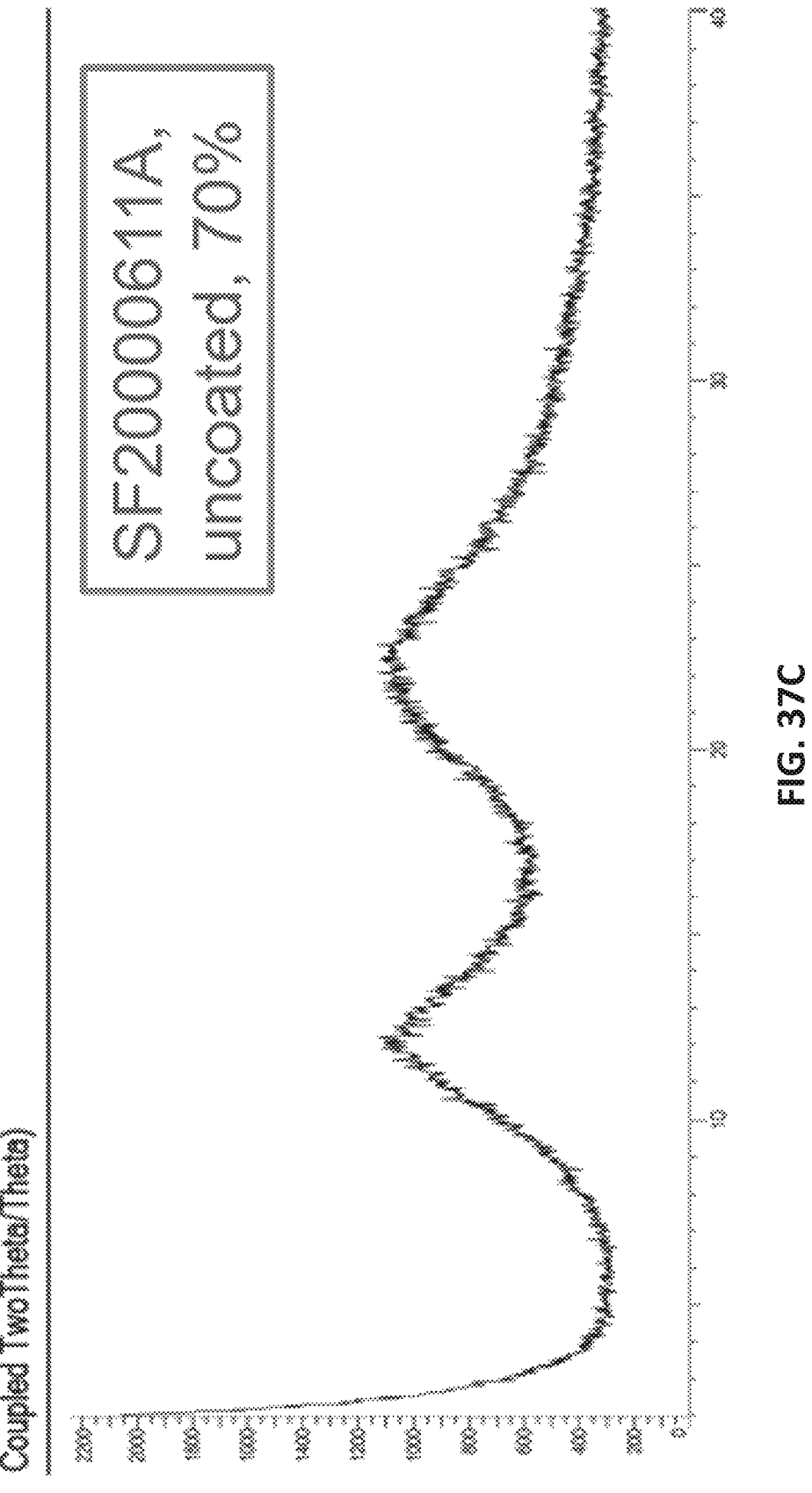
Figure 37D:
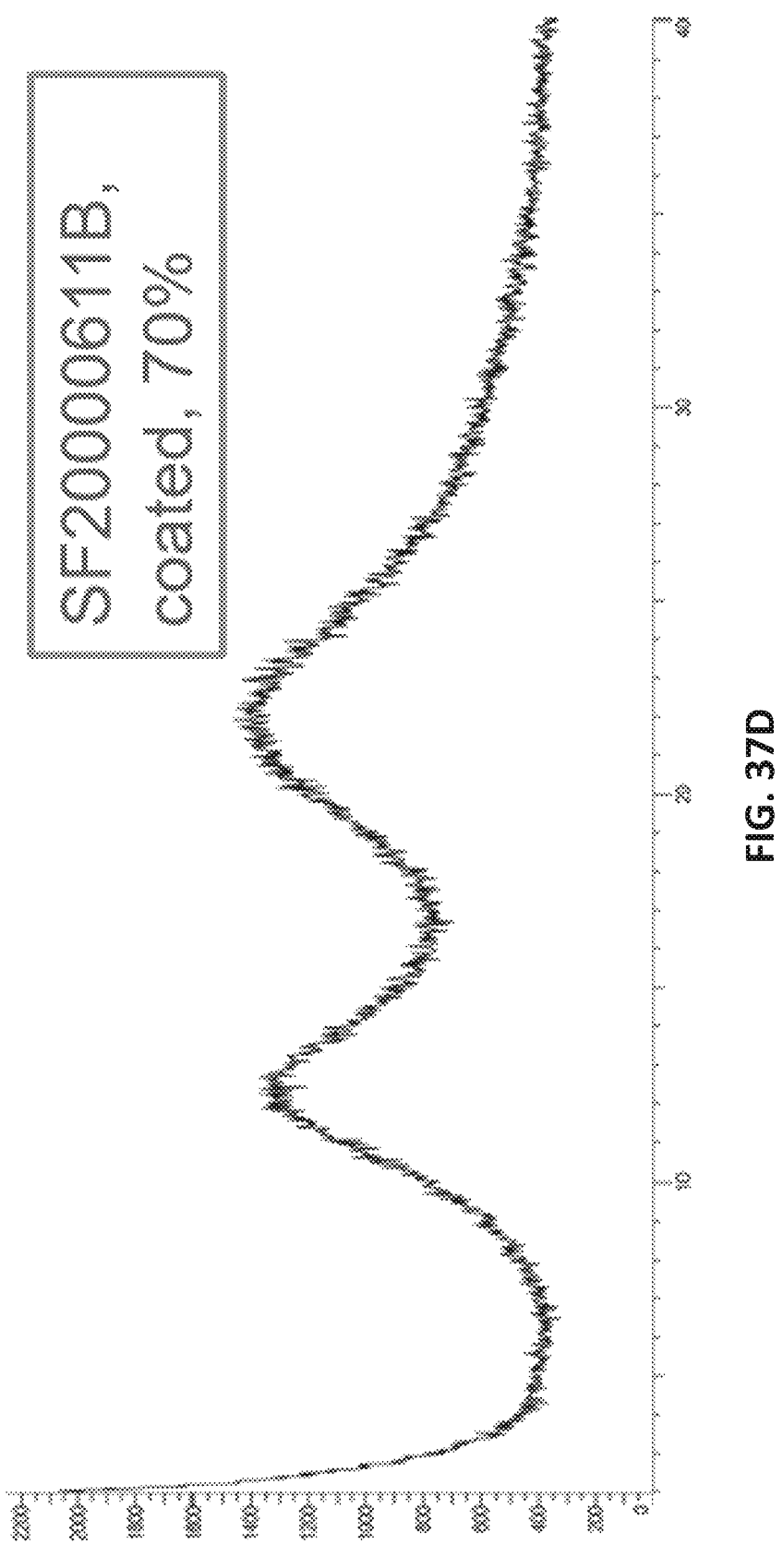
Figure 37E:
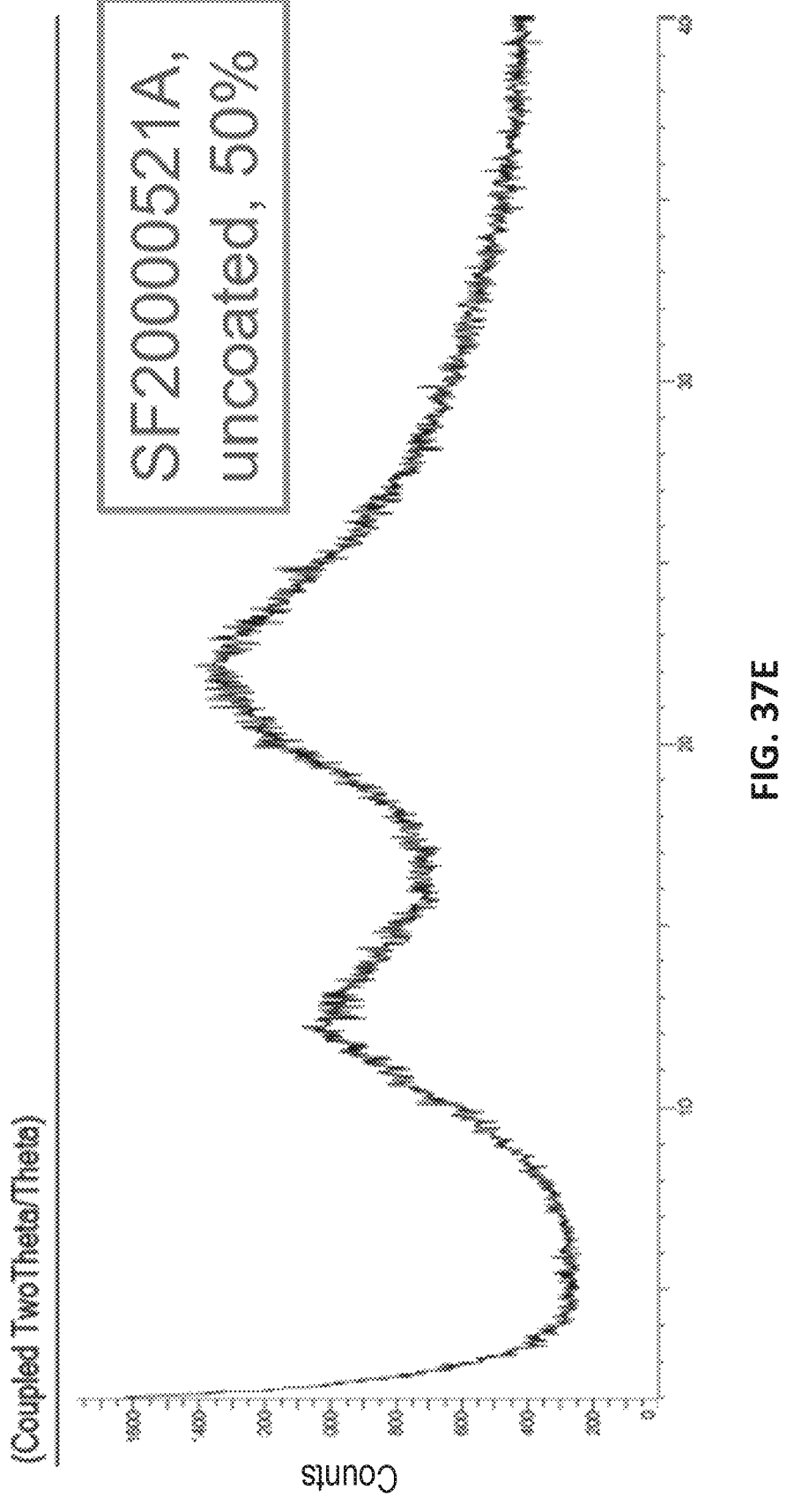
Figure 38A:
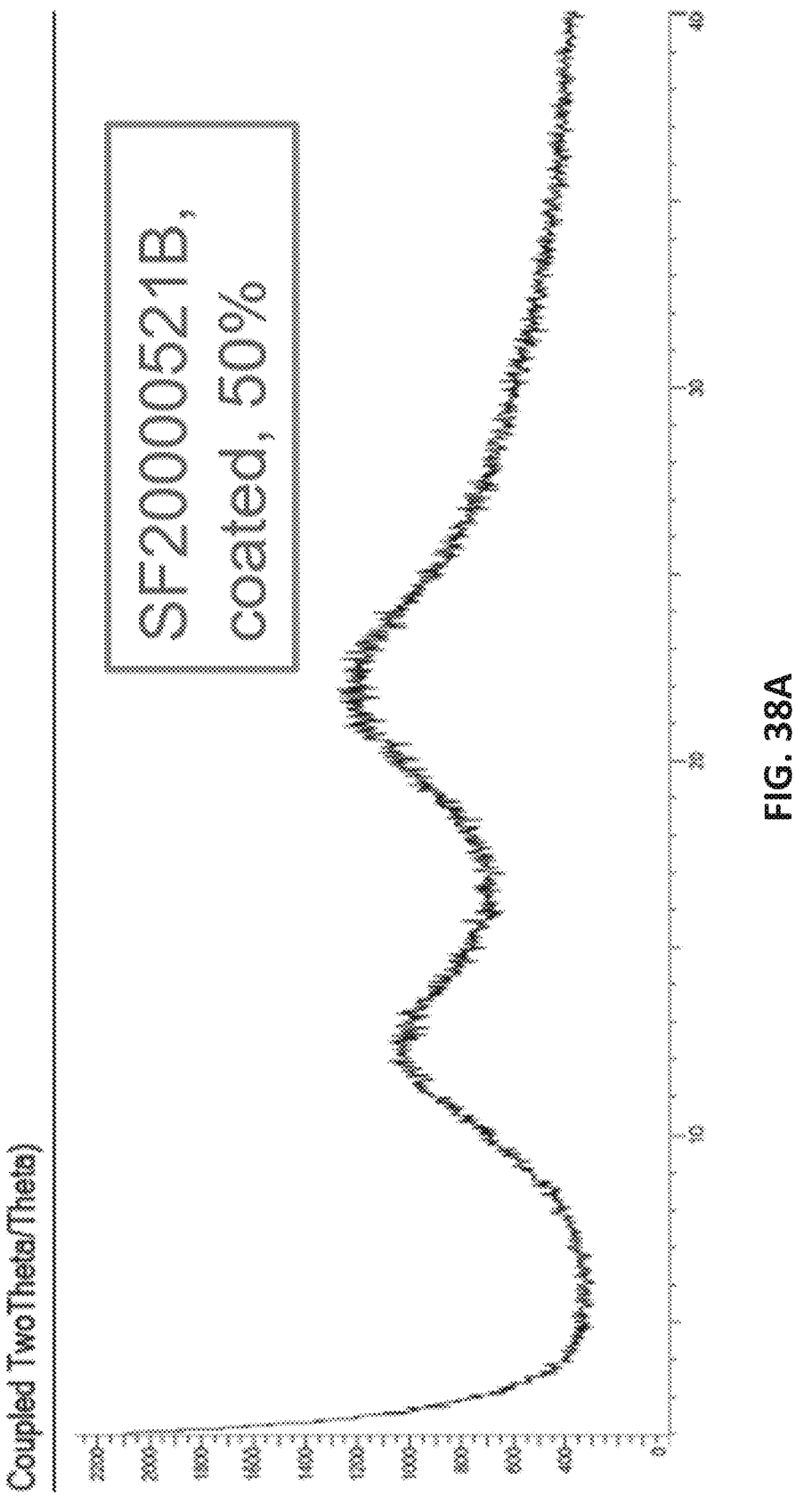
Figure 38B:
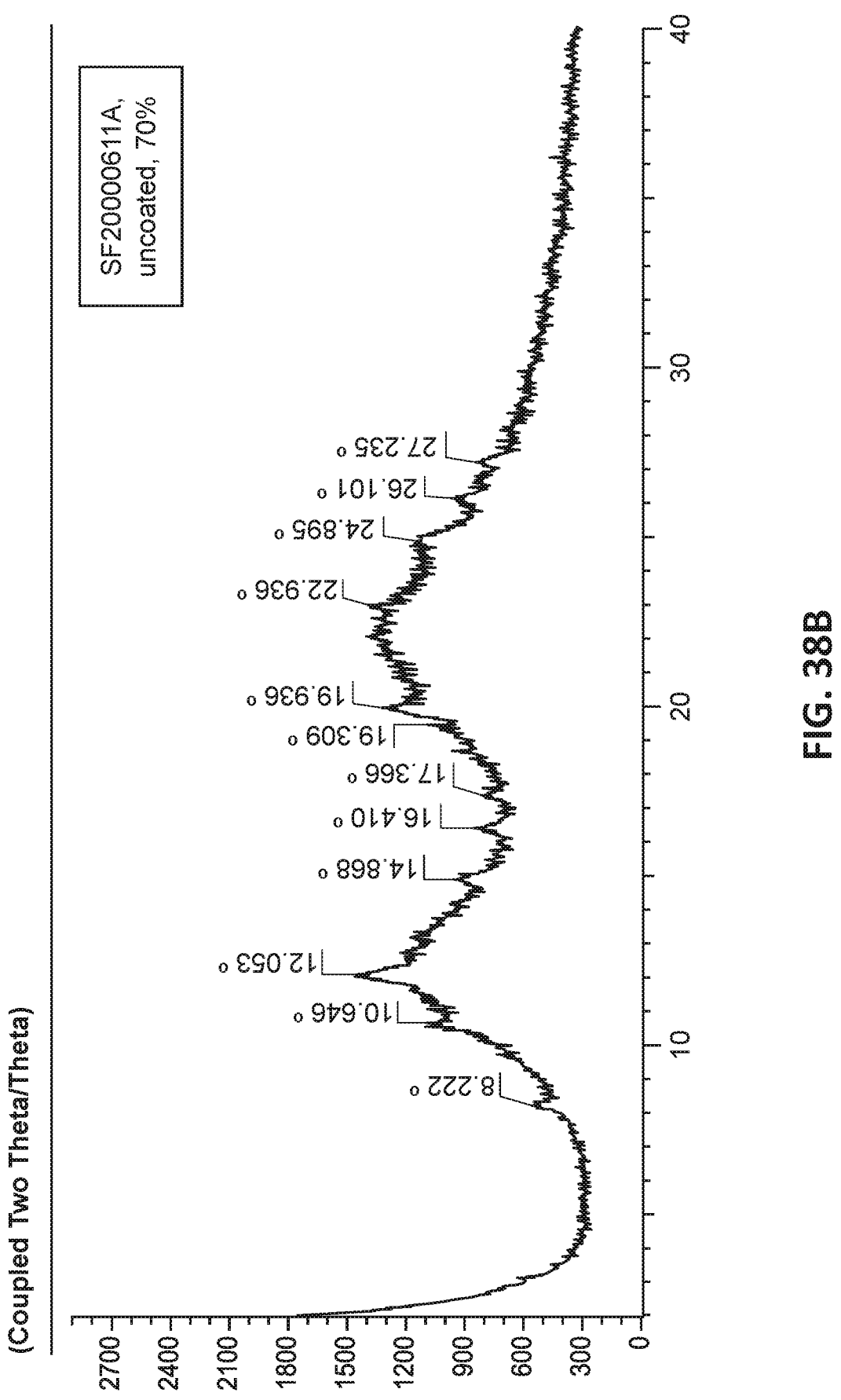
Figure 38C:
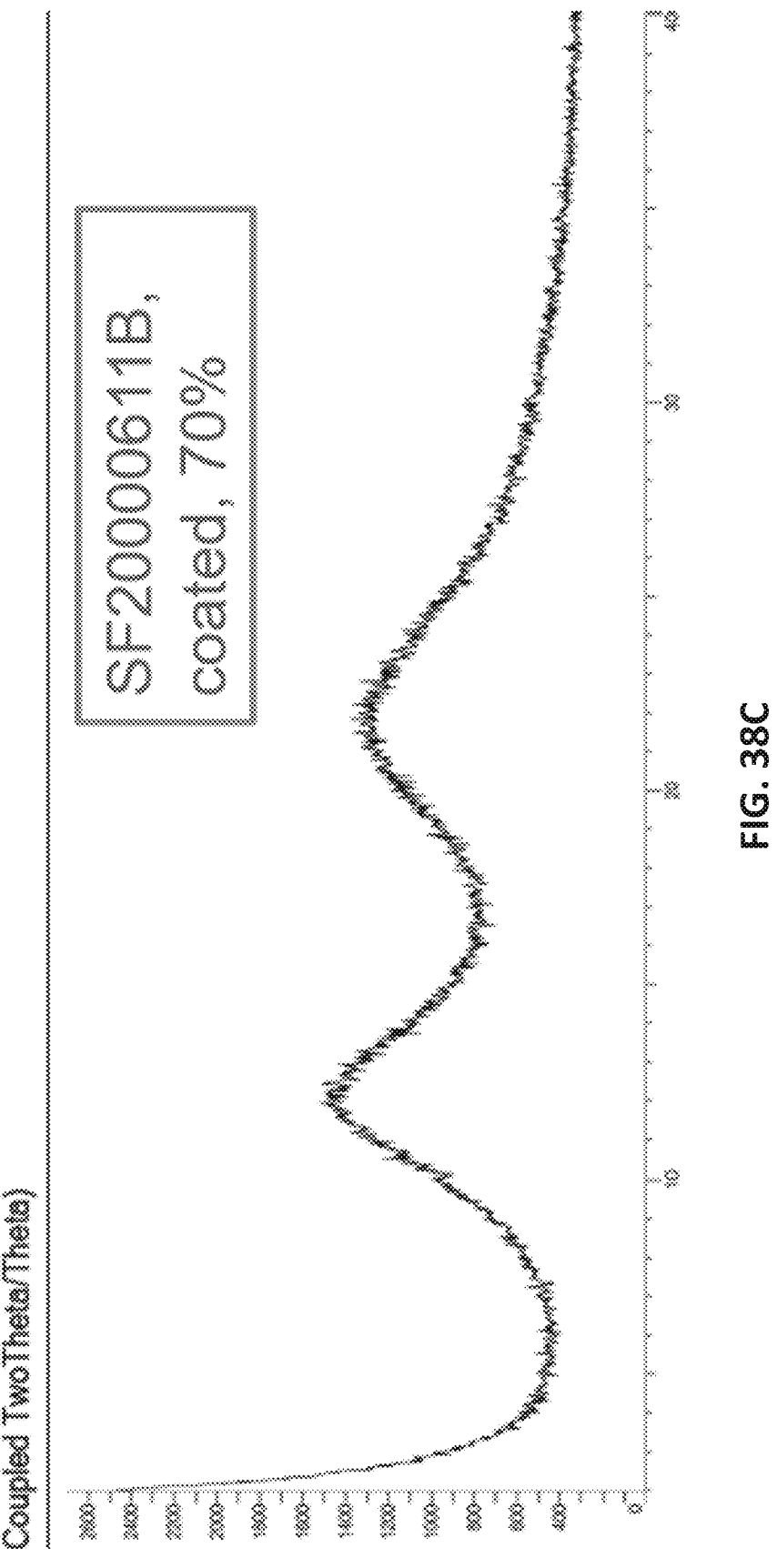
Figure 38D:
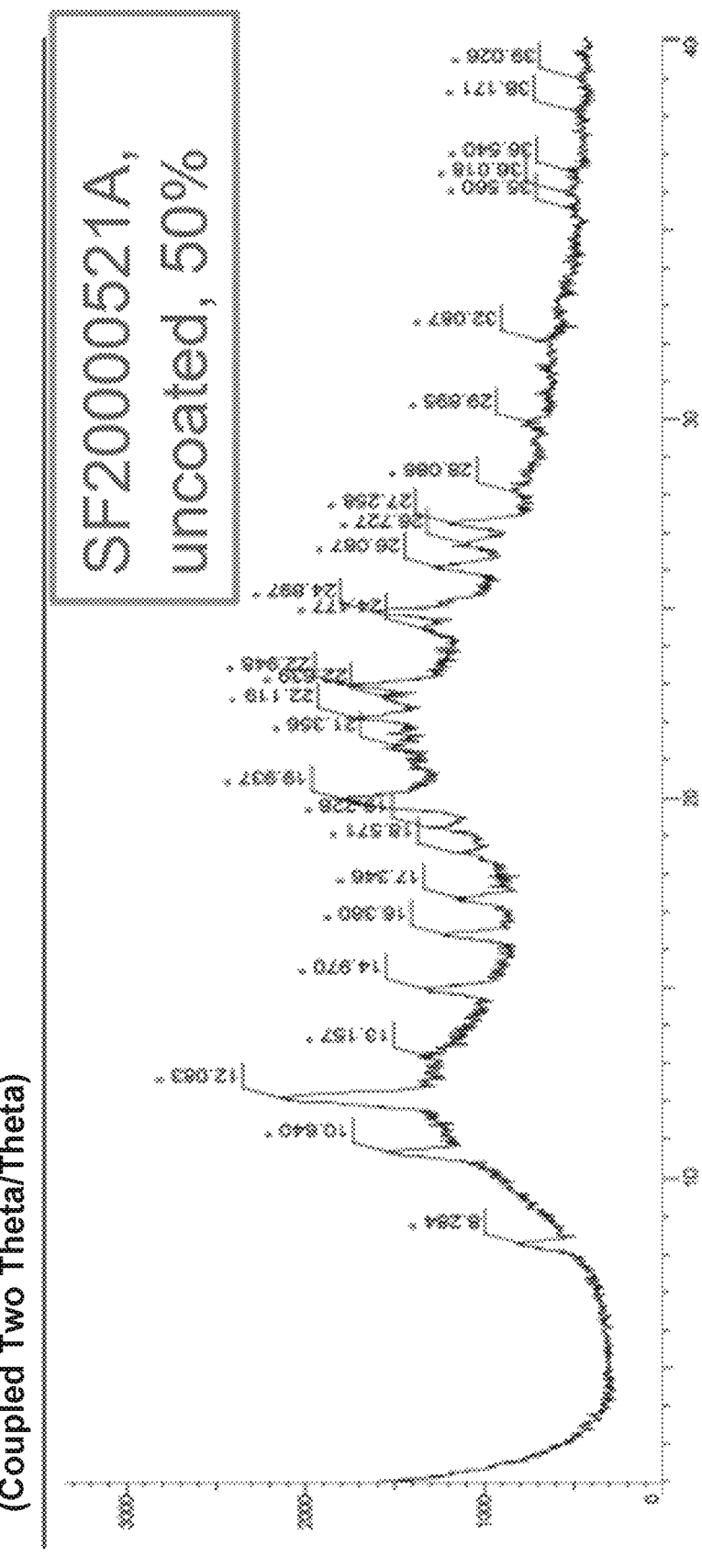

FIGS. 36A-36C depict the appearance of the uncoated and metal oxide coated ASD particles (aluminum oxide/Nifedipine/PVP) with 50% (SF20000521) and 70% (SF20000611) drug loading that were stored in capped amber bottles for various durations.

FIGS. 37A-37E depict the results of x-ray diffraction analysis of uncoated and metal oxide coated ASD particles (aluminum oxide/Nifedipine/PVP) with 50% (SF20000521) and 70% (SF20000611) drug loading that were stored in capped amber bottles for 3 months at 25° C. and 60% relative humidity.

FIGS. 38A-38D depict the results of x-ray diffraction analysis of uncoated and metal oxide coated ASD particles (aluminum oxide/Nifedipine/PVP) with 50% (SF20000521) and 70% (SF20000611) drug loading that were stored in capped with induction sealed HDPE bottles for 3 months at 40° C. and 75% relative humidity.

Figure 39A:
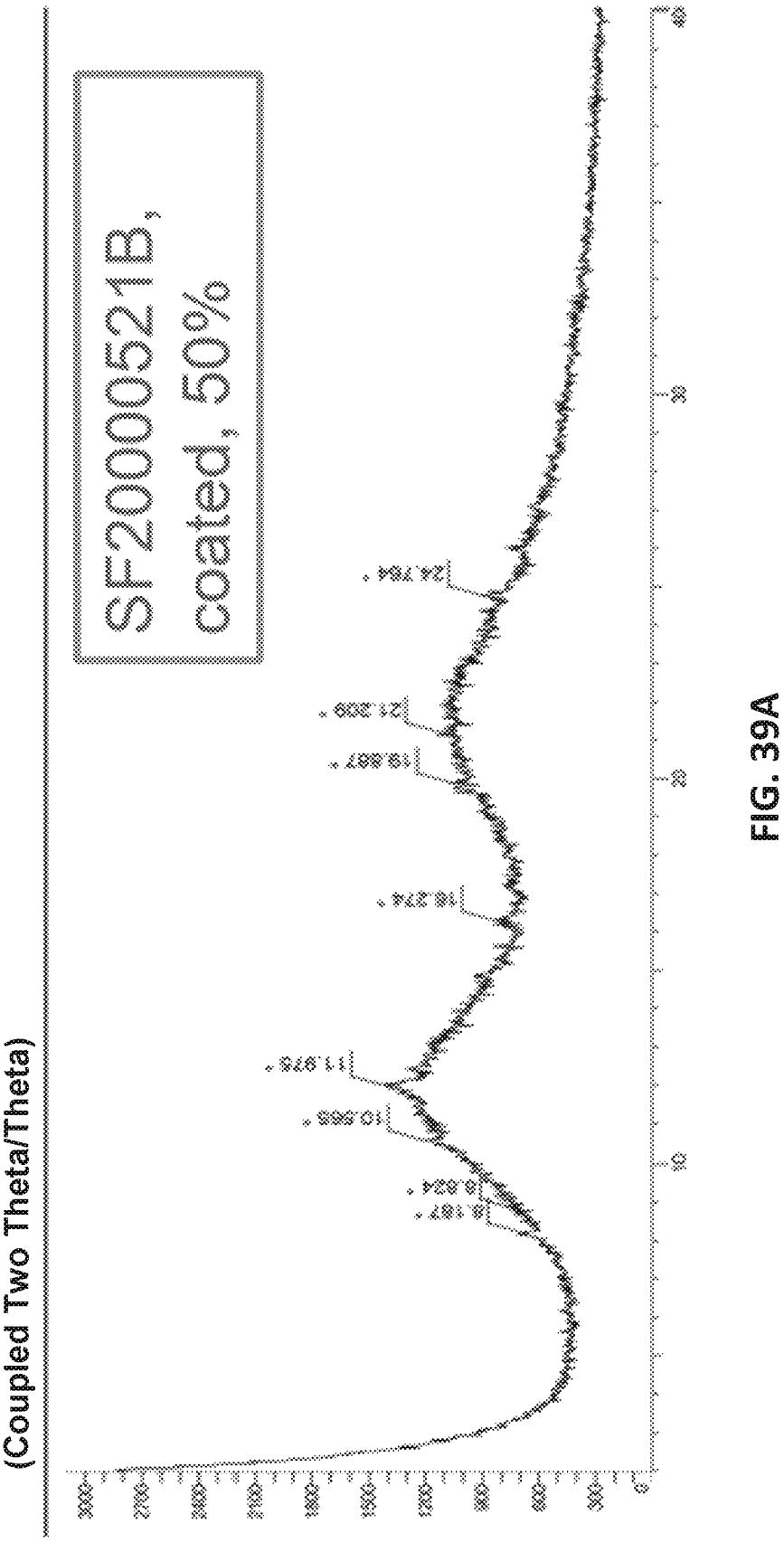
Figure 39B:
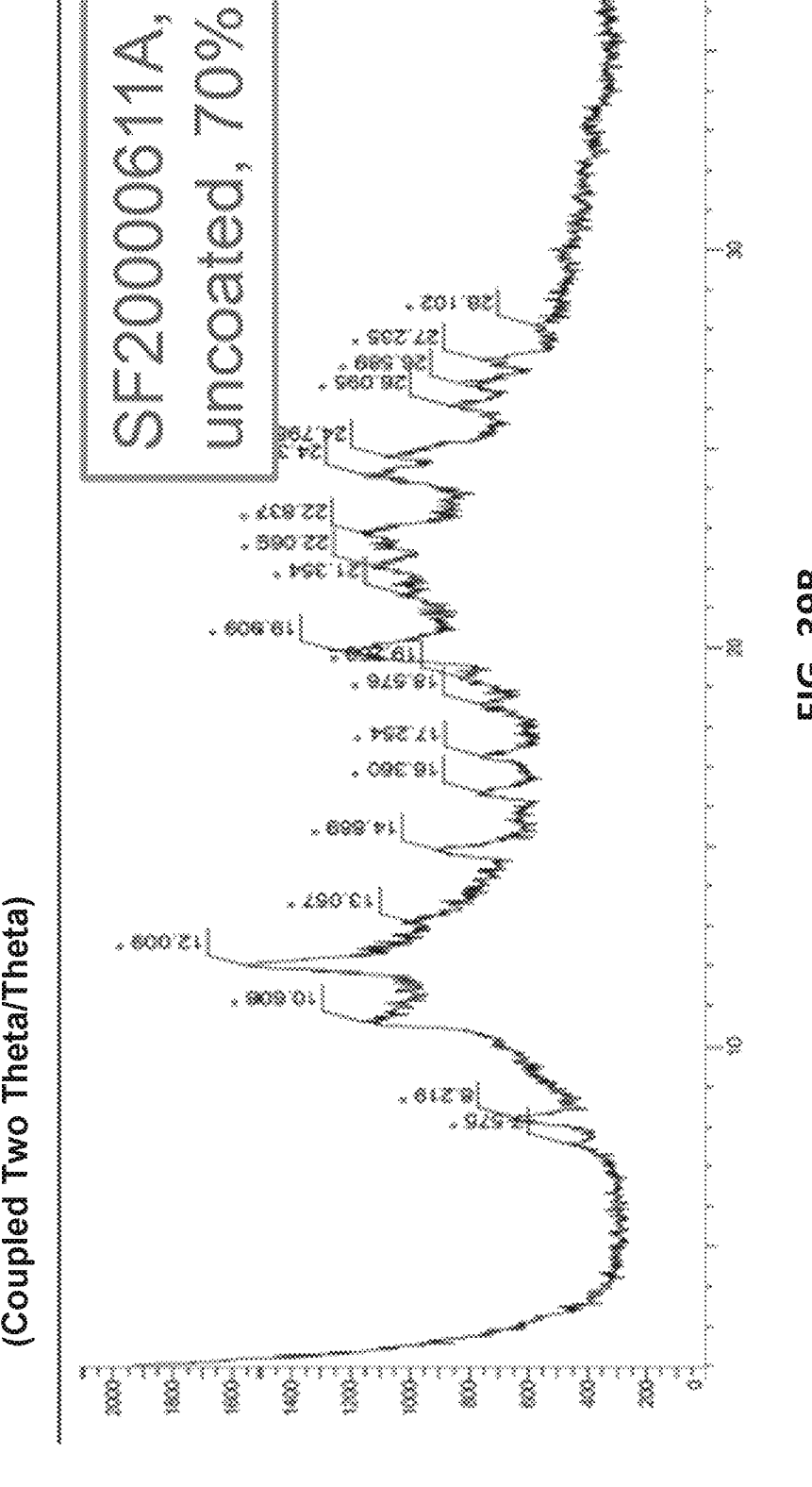
Figure 39C:
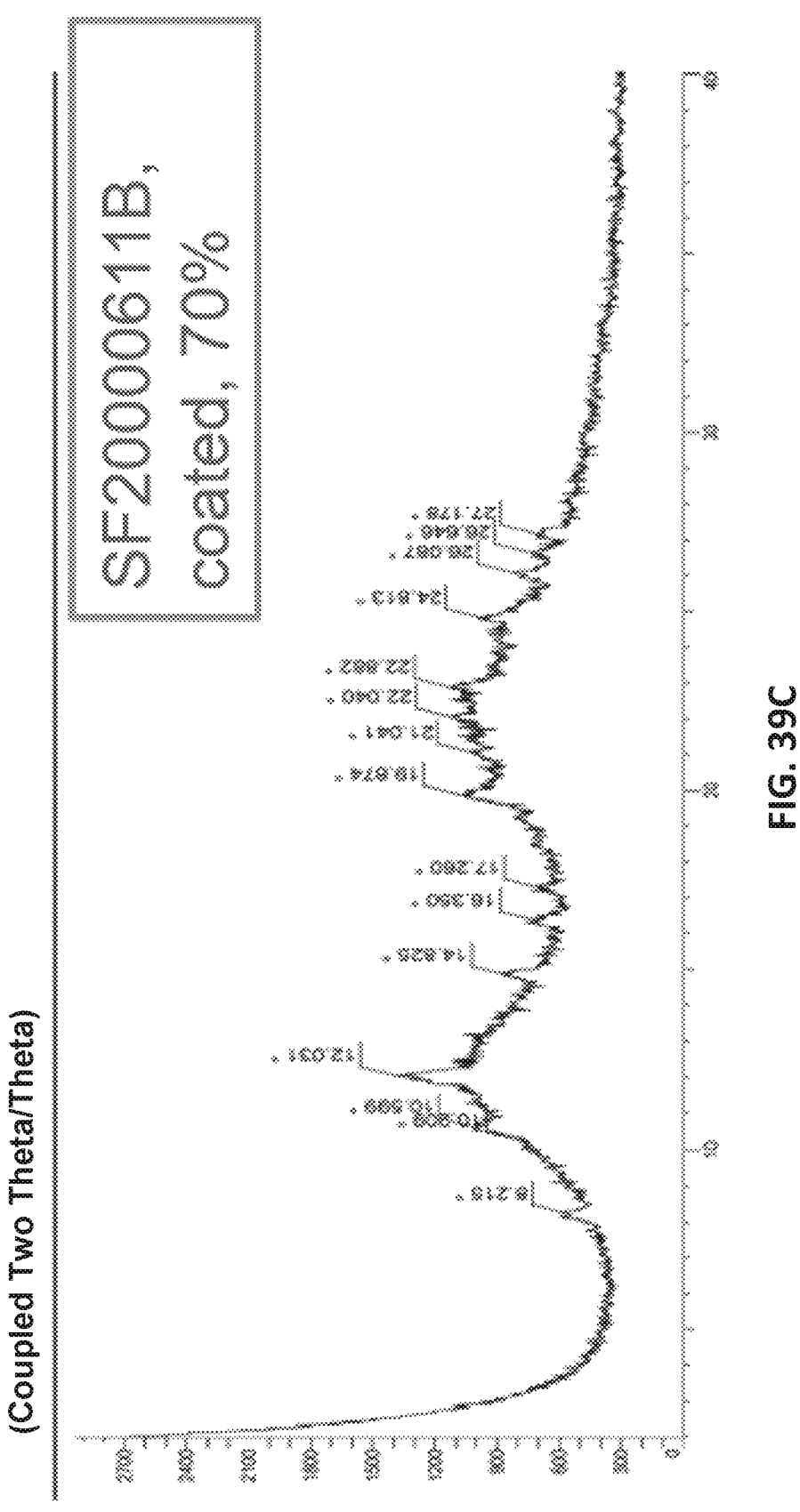

FIG. 39A-39C depict the results of x-ray diffraction analysis of uncoated and metal oxide coated ASD particles (aluminum oxide/Nifedipine/PVP) with 50% (SF20000521) and 70% (SF20000611) drug loading that were stored in open HDPE bottles with no cap for 3 months at 40° C. and 75% relative humidity.

Figure 40A:
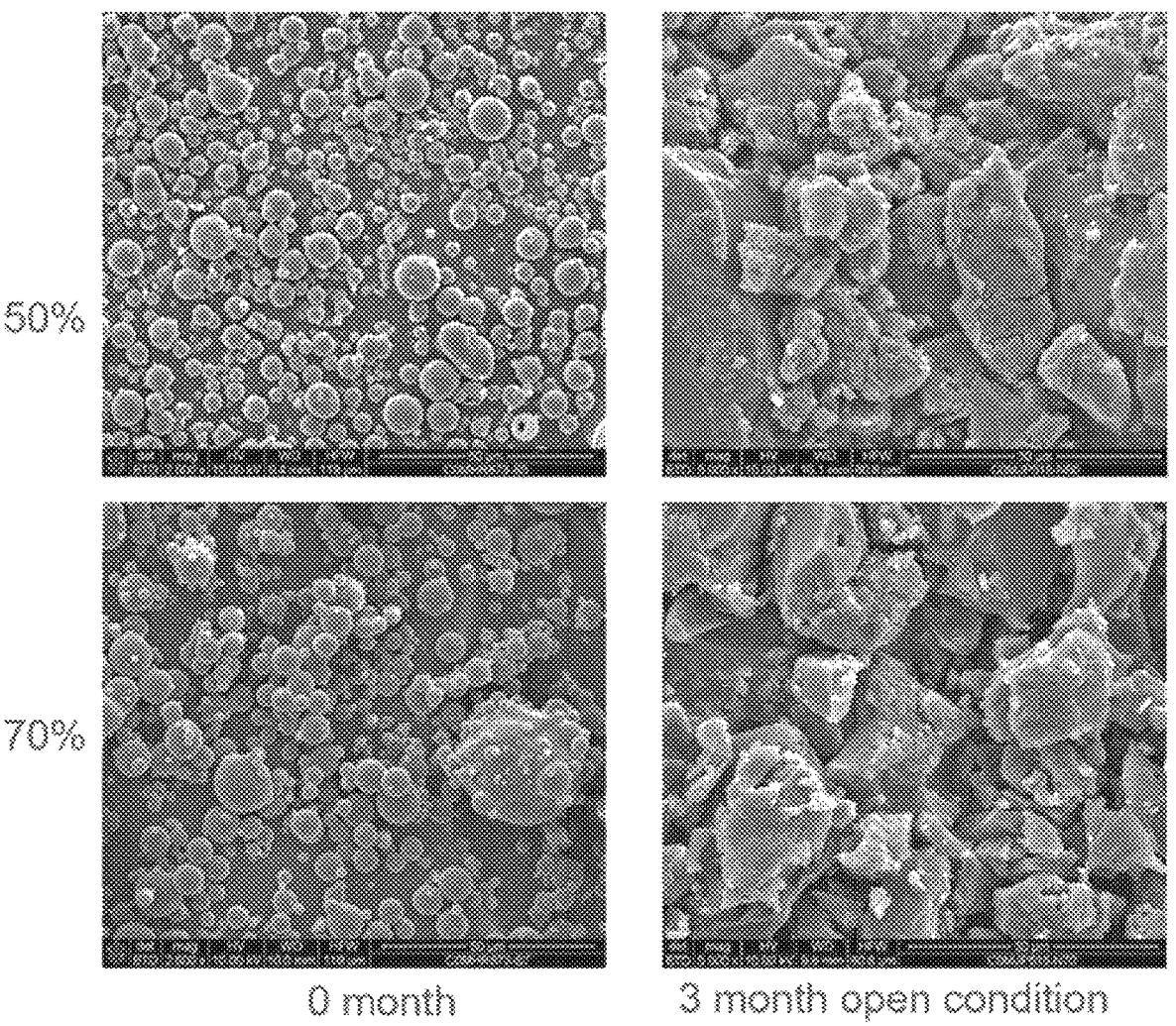
Figure 40B:
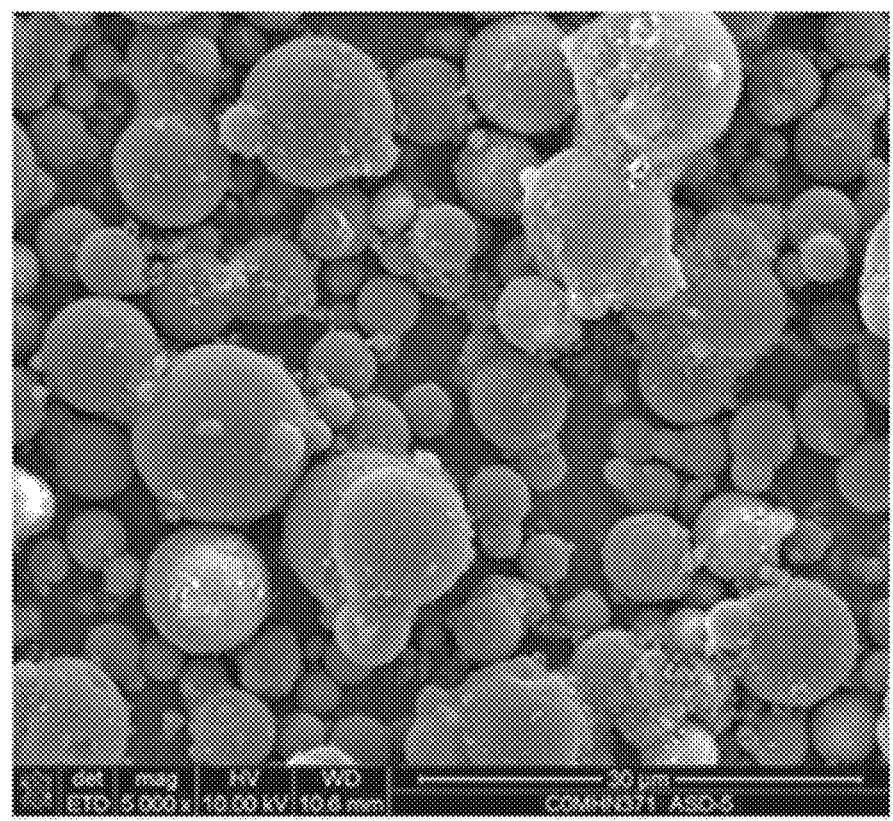
Figure 40C:
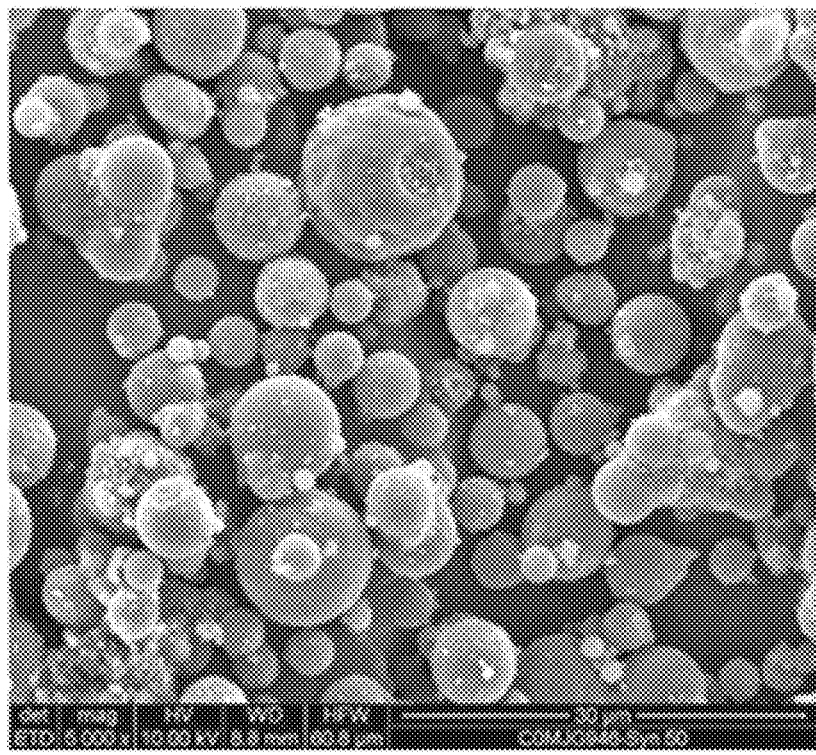
Figure 40D:
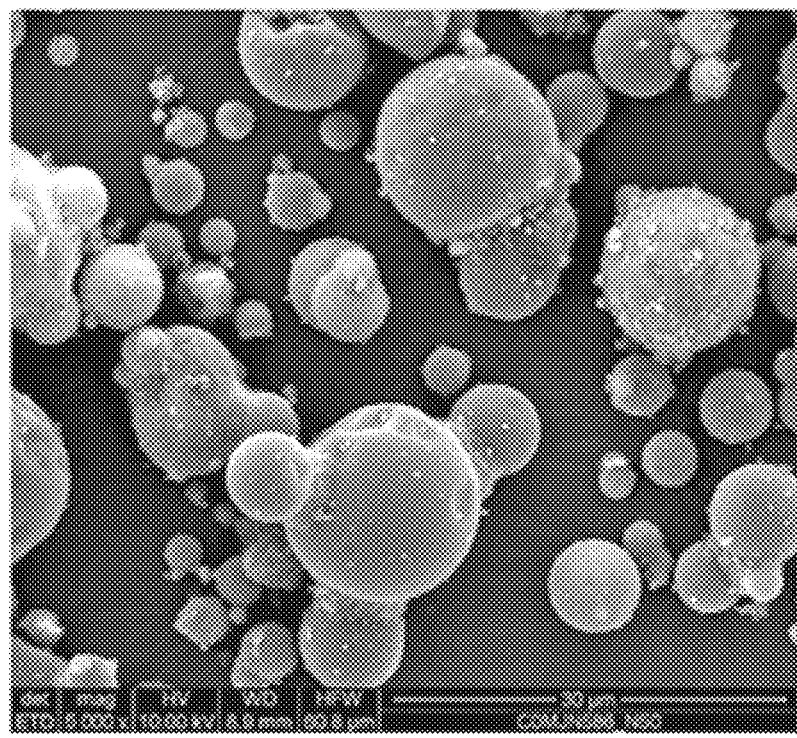
Figure 40E:
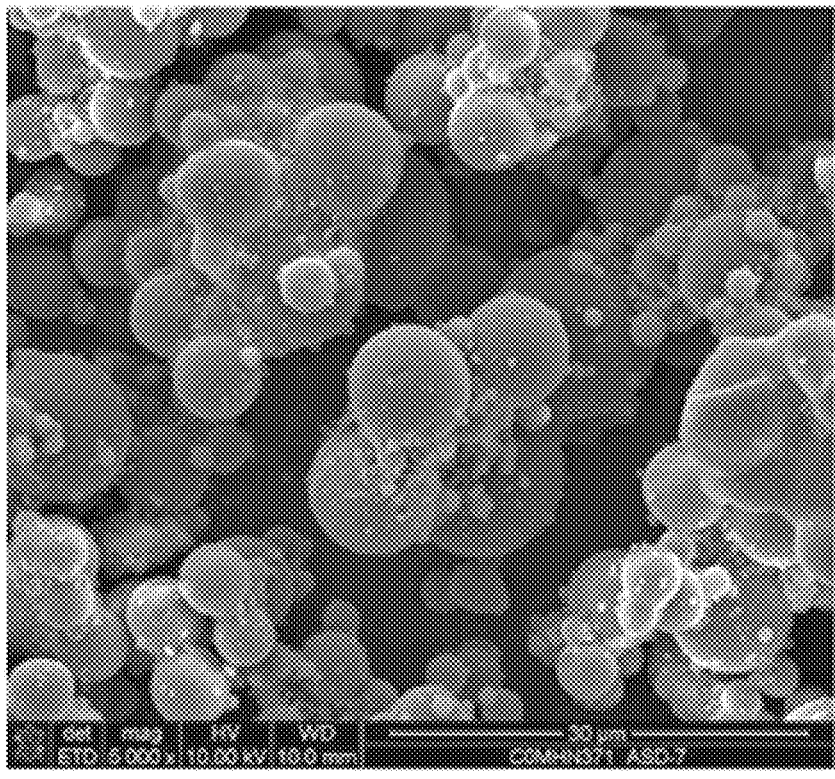
Figure 40F:
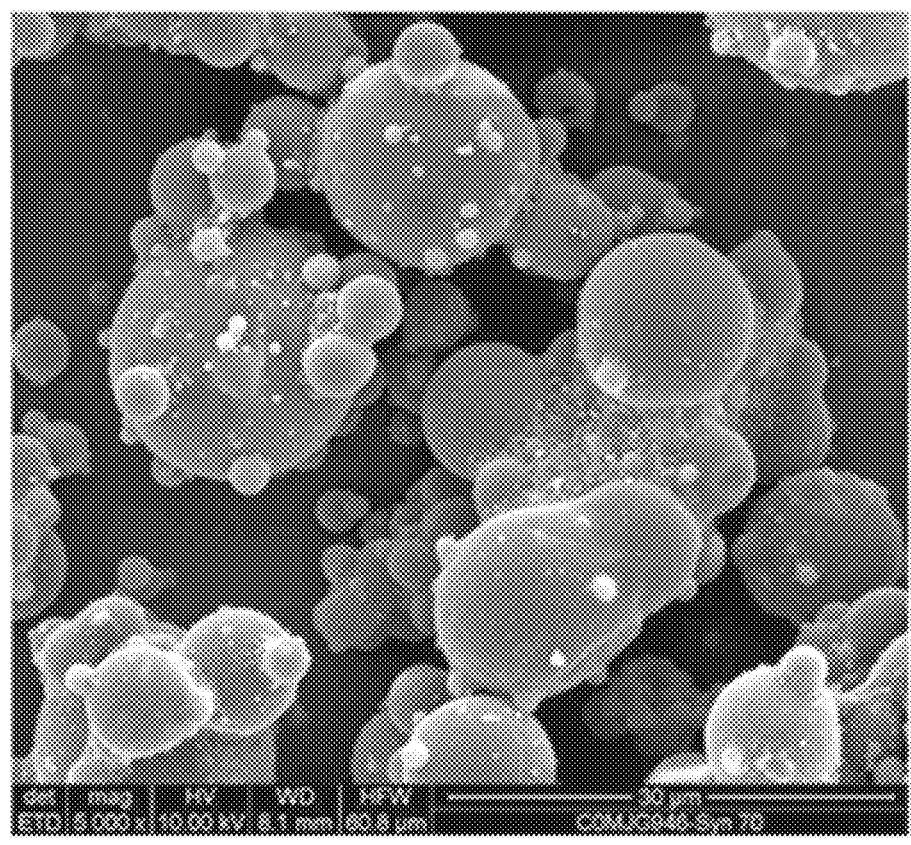
Figure 40G:
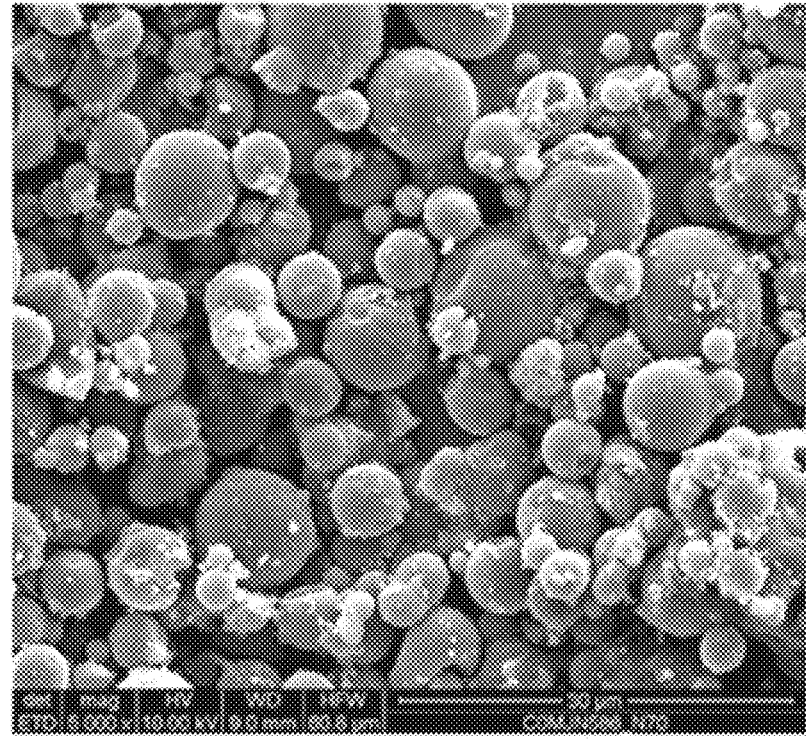

FIGS. 40A-40G depict scanning electron microscopy images of uncoated and metal oxide coated ASD particles (aluminum oxide/nifedipine/HPMCAS) with 50% (SF20000521) and 70% (SF20000611) drug loading that were either freshly prepared, after 2 month storage, or after 3 month storage in open HDPE bottles with no cap at 40° C. and 75% relative humidity. FIG. 40A depicts the images of uncoated ASDs, completely gelled and crystallization observed. FIG. 40B depicts ASD with coated 50% drug loading and FIG. 40C depicts coated ASD with 70% drug loading. No crystallization observed for both coated ASDs with 50% or 70% drug loading after 3 month storage at 40° C. and 75% relative humidity.

DETAILED DESCRIPTION

The present disclosure provides methods of preparing pharmaceutical compositions comprising particles of an amorphous solid dispersion (ASD) ("ASD particles") coated with one or more layers of an oxide, e.g., a metal oxide. The coating layers are conformal and of controlled thickness. The coating process described herein can provide ASD particles in which crystallization of the API is significantly inhibited. Importantly, the coating can reduce the need for a high weight percent of polymer in the ASD. This permits the preparation of ASD particles with high drug loading. For example, the ASD particles can have 50%, 60% or 70% wt/wt drug loading. This high drug loading of the particles together with the relative thinness of the oxide coating permits the preparation of pharmaceutical compositions. Because the coating is relatively thin, drug products with high drug loading can be produced. For example, the metal oxide layer can have a thickness in range of 0.1 nm to 100 nm. In addition, the oxide coating can improve characteristic of ASD particles related to various aspects of drug product manufacturing. For example, coated ASD particles can have improved flowability and compressibility compared to otherwise identical uncoated ASD particles. In addition, coated ASD particles can have a reduced tendency to agglomerate compared to otherwise identical uncoated ASD particles. Finally, there are benefits with respect to cost and ease of manufacture because multiple coatings can be applied in the same reactor.

Drug

The term "drug," in its broadest sense includes all small molecule (e.g., non-biologic) APIs, in particular APIs that are organic molecules. The drug could be selected from the group consisting of an analgesic, an anesthetic, an anti-inflammatory agent, an anthelmintic, an anti-arrhythmic agent, an antiasthma agent, an antibiotic, an anticancer agent, an anticoagulant, an antidepressant, an antidiabetic agent, an antiepileptic, an antihistamine, an antitussive, an antihypertensive agent, an antimuscarinic agent, an antimycobacterial agent, an antineoplastic agent, an antioxidant agent, an antipyretic, an immunosuppressant, an immunostimulant, an antithyroid agent, an antiviral agent, an anxiolytic sedative, a hypnotic, a neuroleptic, an astringent, a bacteriostatic agent, a beta-adrenoceptor blocking agent, a blood product, a blood substitute, a bronchodilator, a buffering agent, a cardiac inotropic agent, a chemotherapeutic, a contrast media, a corticosteroid, a cough suppressant, an expectorant, a mucolytic, a diuretic, a dopaminergic, an antiparkinsonian agent, a free radical scavenging agent, a growth factor, a haemostatic, an immunological agent, a lipid regulating agent, a muscle relaxant, a parasympathomimetic, a parathyroid calcitonin, a biphosphonate, a prostaglandin, a radio-pharmaceutical, a hormone, a sex hormone, an anti-allergic agent, an appetite stimulant, an anoretic, a steroid, a sympathomimetic, a thyroid agent, a vaccine, a vasodilator and a xanthine.

Exemplary types of small molecule drugs include, but are not limited to, acetaminophen, clarithromycin, azithromycin, ibuprofen, fluticasone propionate, salmeterol, pazopanib HCl, palbociclib, and amoxicillin potassium clavulanate.

Metal Oxide Material

The term "metal oxide material," in its broadest sense includes all materials formed from the reaction of elements considered metals or metalloid with oxygen-based oxidants. Exemplary metal oxide materials include, but are not limited to, aluminum oxide, titanium dioxide, iron oxide, gallium oxide, magnesium oxide, zinc oxide, niobium oxide, hafnium oxide, tantalum oxide, lanthanum oxide, and zirconium dioxide. Silicon oxide is an example of a metal oxide created by reaction between a metalloid and an oxygen-based oxidants. Exemplary oxidants include, but are not limited to, water, ozone, and inorganic peroxide.

Atomic Layer Deposition (ALD)

Atomic layer deposition is a thin film deposition technique in which the sequential addition of self-limiting monolayers of an element or compound allows deposition of a film with thickness and uniformity controlled to the level of an atomic or molecular monolayer. Self-limited means that only a single atomic layer is formed at a time, and a subsequent process step is required to regenerate the surface and allow further deposition.

Reactor System

The term "reactor system" in its broadest sense includes all systems that could be used to perform ALD. An exemplary reactor system is illustrated in FIG. 1 and further described below.

Figure 1:
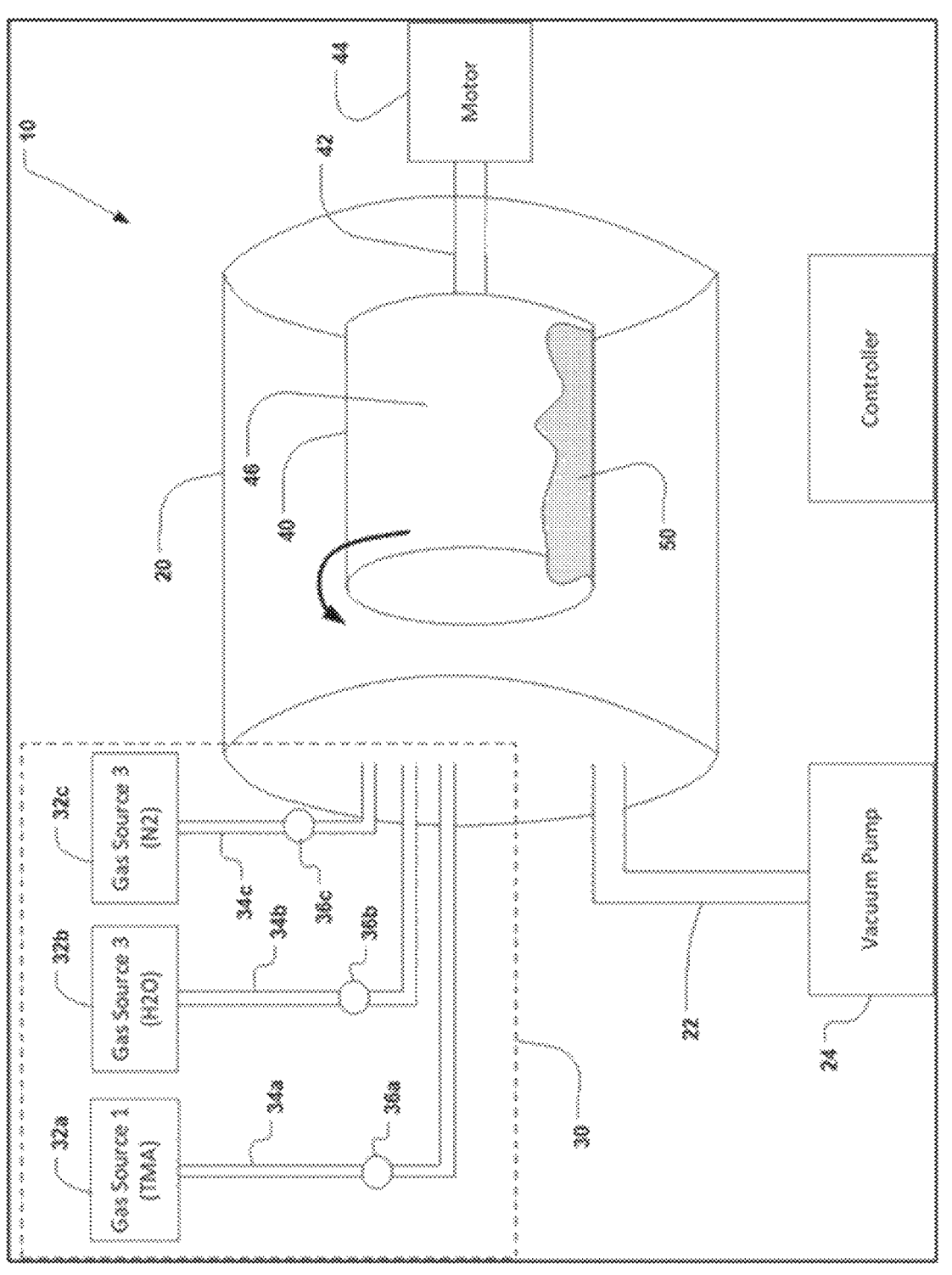
FIG. 1 is a schematic illustration of a rotary reactor for ALD coating of particles, e.g., ASD particles.

FIG. 1 illustrates a reactor system 10 for performing coating of particles, with thin-film coatings. The reactor system 10 can perform ALD coating. The reactor system 10 permits ALD coating to be performed at higher (above 50° C., e.g., 50-100° C. or higher) or lower processing temperature, e.g., below 50° C., e.g., at or below 35° C. For example, the reactor system 10 can form thin-film metal oxides on the particles primarily by ALD at temperatures of 22-35° C., e.g., 25-35° C., 25-30° C., or 30-35° C. In general, the particles can remain or be maintained at such temperatures. This can be achieved by having the reactant gases and/or the interior surfaces of the reactor chamber (e.g., the chamber 20 and drum 40 discussed below) remain or be maintained at such temperatures.

Again, illustrating an ALD process, the reactor system 10 includes a stationary vacuum chamber 20 which is coupled to a vacuum pump 24 by vacuum tubing 22. The vacuum pump 24 can be an industrial vacuum pump sufficient to establish pressures less than 1 Torr, e.g., 1 to 100 mTorr, e.g., 50 mTorr. The vacuum pump 24 permits the chamber 20 to be maintained at a desired pressure and permits removal of reaction byproducts and unreacted process gases.

In operation, the reactor 10 performs the ALD thin-film coating process by introducing gaseous precursors of the coating into the chamber 20. The gaseous precursors are spiked alternatively into the reactor. This permits the ALD process to be a solvent-free process. The half-reactions of the ALD process are self-limiting, which can provide Angstrom level control of deposition. In addition, the ALD reaction can be performed at low temperature conditions, such as below 50° C., e.g., below 35° C.

The chamber 20 is also coupled to a chemical delivery system 30. The chemical delivery system 30 includes three or more gas sources 32a, 32b, 32c coupled by respective delivery tubes 34a, 34b, 34c and controllable valves 36a, 36b, 36c to the vacuum chamber 20. The chemical delivery system 30 can include a combination of restrictors, gas flow controllers, pressure transducers, and ultrasonic flow meters to provide controllable flow rate of the various gasses into the chamber 20. The chemical delivery system 30 can also include one or more temperature control components, e.g., a heat exchanger, resistive heater, heat lamp, etc., to heat or cool the various gasses before they flow into the chamber 20. Although FIG. 1 illustrates separate gas lines extending in parallel to the chamber for each gas source, two or more of the gas lines could be joined, e.g., by one or more three-way valves, before the combined line reaches the chamber 20. In addition, although FIG. 1 illustrates three gas sources, the use of four gas sources could enable the in-situ formation of laminate structures having alternating layers of two different metal oxides.

Two of the gas sources provide two chemically different gaseous reactants for the coating process to the chamber 20. Suitable reactants for ALD methods include any of or a combination of the following: monomer vapor, metal-organics, metal halides, oxidants, such as ozone or water vapor, and polymer or nanoparticle aerosol (dry or wet). For example, the first gas source 32a can provide gaseous trimethylaluminum (TMA) or titanium tetrachloride (TiCl$_4$), whereas the second gas source 32b can provide water vapor.

One of the gas sources can provide a purge gas. In particular, the third gas source can provide a gas that is chemically inert to the reactants, the coating, and the particles being processed. For example, the purge gas can be N$_2$, or a noble gas, such as argon.

A rotatable coating drum 40 is held inside the chamber 20. The drum 40 can be connected by a drive shaft 42 that extends through a sealed port in a side wall of the chamber 20 to a motor 44. The motor 44 can rotate the drum at speeds of 1 to 100 rpm. Alternatively, the drum can be directly connected to a vacuum source through a rotary union.

The particles to be coated, shown as a particle bed 50, are placed in an interior volume 46 of the drum 40. The drum 40 and chamber 20 can include sealable ports (not illustrated) to permit the particles to be placed into and removed from the drum 40.

The body of the drum 40 is provided by one or more of a porous material, a solid metal, and a perforated metal. The pores through the cylindrical side walls of the drum 40 can have a dimension of 10 μm.

In operation, one of the gasses flows into chamber 20 from the chemical delivery system 30 as the drum 40 rotates. A combination of pores (1-100 μm), holes (0.1-10 mm), or large openings in the coating drum 40 serve to confine the particles in the coating drum 40 while allowing rapid delivery of precursor chemistry and pumping of byproducts or unreacted species. Due to the pores in the drum 40, the gas can flow between the exterior of the drum 40, i.e., the reactor chamber 20, and the interior of the drum 40. In addition, rotation of the drum 40 agitates the particles to keep them separate, ensuring a large surface area of the particles remains exposed. This permits fast, uniform interaction of the particle surface with the process gas.

In some implementations, one or more temperature control components are integrated into the drum 40 to permit control of the temperature of the drum 40. For example, resistive heater, a thermoelectric cooler, or other component can in or on the side walls of the drum 40.

The reactor system 10 also includes a controller 60 coupled to the various controllable components, e.g., vacuum pump 24, gas distribution system 30, motor 44, a temperature control system, etc., to control operation of the reactor system 10. The controller 60 can also be coupled to various sensors, e.g., pressure sensors, flow meters, etc., to provide closed loop control of the pressure of the gasses in the chamber 20.

In general, the controller 60 can operate the reactor system 10 in accord with a "recipe." The recipe specifies an operating value for each controllable element as a function of time. For example, the recipe can specify the times during which the vacuum pump 24 is to operate, the times of and flow rate for each gas source 32a, 32b, 32c, the rotation rate of the motor 44, etc. The controller 60 can receive the recipe as computer-readable data (e.g., that is stored on a non-transitory computer readable medium).

The controller 60 and other computing devices part of systems described herein can be implemented in digital electronic circuitry, or in computer software, firmware, or hardware. For example, the controller can include a processor to execute a computer program as stored in a computer program product, e.g., in a non-transitory machine-readable storage medium. Such a computer program (also known as a program, software, software application, or code) can be written in any form of programming language, including compiled or interpreted languages, and it can be deployed in any form, including as a standalone program or as a module, component, subroutine, or other unit suitable for use in a computing environment. In some implementations, the controller 60 is a general-purpose programmable computer. In some implementations, the controller can be implemented using special purpose logic circuitry, e.g., an FPGA (field programmable gate array) or an ASIC (application specific integrated circuit).

Operation

Initially, particles are loaded into the drum 40 in the reactor system 10. The particles can have a solid core comprising a drug, e.g., one of the drugs discussed above. Once any access ports are sealed, the controller 60 operates the reactor system 10 according to the recipe in order to form the thin-film metal oxide layers on the particles.

In particular, the two reactant gases are alternately supplied to the chamber 20, with each step of supplying a reactant gas followed by a purge cycle in which the inert gas is supplied to the chamber 20 to force out the reactant gas and by-products used in the prior step. Moreover, one or more of the gases (e.g., the reactant gases and/or the inert gas) can be supplied in pulses in which the chamber 20 is filled with the gas to a specified pressure, a delay time is permitted to pass, and the chamber is evacuated by the vacuum pump 24 before the next pulse commences.

In particular, the controller 60 can operate the reactor system 10 as follows.

In a first reactant half-cycle, while the motor 44 rotates the drum 40 to agitate the particles 50:

i) The gas distribution system 30 is operated to flow the first reactant gas, e.g., TMA, from the source 32a into the chamber 20 until a first specified pressure is achieved. The specified pressure can be 0.1 Torr to half of the saturation pressure of the reactant gas.

ii) Flow of the first reactant is halted, and a specified delay time is permitted to pass, e.g., as measured by a timer in the controller. This permits the first reactant to flow through the particle bed in the drum 40 and react with the surface of the particles 50 inside the drum 40.

iii) The vacuum pump 50 evacuates the chamber 20, e.g., down to pressures below 1 Torr, e.g., to 1 to 100 mTorr, e.g., 50 mTorr.

These steps (i)-(iii) can be repeated a number of times set by the recipe, e.g., two to ten times, e.g., six times.

Next, in a first purge cycle, while the motor 44 rotates the drum to agitate the particles 50:

iv) The gas distribution system 30 is operated to flow the inert gas, e.g., N$_2$, from the source 32c into the chamber 20 until a second specified pressure is achieved. The second specified pressure can be 1 to 100 Torr.

v) Flow of the inert gas is halted, and a specified delay time is permitted to pass, e.g., as measured by the timer in the controller. This permits the inert gas to flow through the pores in the drum 40 and diffuse through the particles 50 to displace the reactant gas and any vaporous by-products.

vi) The vacuum pump 50 evacuates the chamber 20, e.g., down to pressures below 1 Torr, e.g., to 1 to 500 mTorr, e.g., 50 mTorr.

These steps (iv)-(vi) can be repeated a number of times set by the recipe, e.g., six to twenty times, e.g., sixteen times.

In a second reactant half-cycle, while the motor 44 rotates the drum 40 to agitate the particles 50:

vii) The gas distribution system 30 is operated to flow the second reactant gas, e.g., H2O, from the source 32a into the chamber 20 until a third specified pressure is achieved. The third pressure can be 0.1 Torr to half of the saturation pressure of the reactant gas.

viii) Flow of the second reactant is halted, and a specified delay time is permitted to pass, e.g., as measured by the timer in the controller. This permits the second reactant to flow through the pores in the drum 40 and react with the surface of the particles 50 inside the drum 40.

ix) The vacuum pump 50 evacuates the chamber 20, e.g., down to pressures below 1 Torr, e.g., to 1 to 500 mTorr, e.g., 50 mTorr.

These steps (vii)-(ix) can be repeated a number of times set by the recipe, e.g., two to ten times, e.g., six times.

Next, a second purge cycle is performed. This second purge cycle can be identical to the first purge cycle, or can have a different number of repetitions of the steps (iv)-(vi) and/or different delay time and/or different pressure.

The cycle of the first reactant half-cycle, first purge cycle, second reactant half cycle and second purge cycle can be repeated a number of times set by the recipe, e.g., one to ten times.

As noted above, the coating process can be performed at low processing temperature, e.g., below 50° C., e.g., at or below 35° C. In particular, the particles can remain or be maintained at such temperatures during all of steps (i)-(ix) noted above. In general, the temperature of the interior of the reactor chamber does not exceed 35° C. during of steps (i)-(ix). This can be achieved by having the first reactant gas, second reactant gas and inert gas be injected into the chamber at such temperatures during the respective cycles. In addition, physical components of the chamber can remain or be maintained at such temperatures, e.g., using a cooling system, e.g., a thermoelectric cooler, if necessary.

Process for Preparing Pharmaceutical Compositions Comprising Drugs Encapsulated by One or More Layers of Metal Oxide Provided are two exemplary methods for a pharmaceutical composition comprising a drug-containing core (an ASD particle) enclosed by one or more metal oxide materials. The first exemplary method includes the sequential steps of: (a) loading the particles comprising the drug into a reactor, (b) applying a vaporous or gaseous metal precursor to the substrate in the reactor, (c) performing one or more pump-purge cycles of the reactor using inert gas, (d) applying a vaporous or gaseous oxidant to the substrate in the reactor, and (e) performing one or more pump-purge cycles of the reactor using inert gas. In some embodiments of the first exemplary method, the sequential steps (b)-(e) are optionally repeated one or more times to increase the total thickness of the one or more metal oxide materials that enclose the solid core of the coated particles. In some embodiments, the reactor pressure is allowed to stabilize following step (a), step (b), and/or step (d). In some embodiments, the reactor contents are agitated prior to and/or during step (b), step (c), and/or step (e). In some embodiments, a subset of vapor or gaseous content is pumped out prior to step (c) and/or step (e).

The second exemplary method includes (e.g., consists of) the sequential steps of (a) loading the particles comprising the drug into a reactor, (b) reducing the reactor pressure to less than 1 Torr, (c) agitating the reactor contents until the reactor contents have a desired moisture content, (d) pressurizing the reactor to at least 10 Torr by adding a vaporous or gaseous metal precursor, (e) allowing the reactor pressure to stabilize, (f) agitating the reactor contents, (g) pumping out a subset of vapor or gaseous content and determining when to stop pumping based on analysis of content in reactor including metal precursor and byproduct of metal precursor reacting with exposed hydroxyl residues on substrate or on particle surface, (h) performing a sequence of pump-purge cycles of the reactor using insert gas, (i) pressuring the reactor to at least 10 Torr by adding a vaporous or gaseous oxidant, (j) allowing the reactor pressure to stabilize, (k) agitating the reactor contents, (l) pumping out a subset of vapor or gaseous content and determining when to stop pumping based on analysis of content in reactor including metal precursor, byproduct of metal precursor reacting with exposed hydroxyl residues on substrate or on particle surface, and unreacted oxidant, and (m) performing a sequence of pump-purge cycles of the reactor using insert gas. In some embodiments of the second exemplary method, the sequential steps (b)-(m) are optionally repeated one or more times to increase the total thickness of the one or more metal oxide materials that enclose the solid core of the coated particles.

Some embodiments provide a method of preparing a pharmaceutical composition comprising coated particles comprising amorphous solid dispersion of an active pharmaceutical ingredient enclosed by one or more metal oxide layers, the method comprising the sequential steps of: (a) providing uncoated particles of an amorphous solid dispersion comprising an active pharmaceutical ingredient (API) and a polymer; (b) performing atomic layer deposition to apply a metal oxide layer to uncoated particles of an amorphous solid dispersion comprising an active pharmaceutical ingredient and a polymer thereby preparing coated particles comprising an active pharmaceutical ingredient enclosed by one or more metal oxide layers; and (c) processing the coated particles to prepare a pharmaceutical composition.

In some embodiments, the uncoated particles are at least 50% wt/wt API. In some embodiments, the uncoated particles are at least 70% wt/wt API. In some embodiments, the coated particles have a D50 of 0.5 um to 200 um on a volume average basis. In some embodiments, the coated particles have a D90 of 200 um to 2000 um on a volume average basis.

In some embodiments, the glass transition temperature of the active pharmaceutical ingredient in the coated particles is higher than the glass transition temperature of the active pharmaceutical ingredient in the provided particles.

In some embodiments, the polymer is selected from the group consisting of: hydroxypropyl methylcellulose, hydroxypropyl methyl cellulose acetate succinate (HPMCAS), and polyvinylpyrrolidone (PVP), polyvinylpyrrolidone/vinyl acetate, polyethylene glycol (PEG), polyacrylates and polymethacrylates.

In some embodiments, step (a) comprises hot melt extrusion. In some embodiments, step (a) comprises spray drying a composition comprising the polymer and the active pharmaceutical ingredient. In some embodiments, the polymer and the active pharmaceutical ingredient are agitated prior to and/or during step (a).

In some embodiments, the step of performing atomic layer deposition comprises: (b1) loading the particles comprising the drug into a reactor; (b2) applying a vaporous or gaseous metal precursor to the particles in the reactor; (b3) performing one or more pump-purge cycles of the reactor using inert gas; (b4) applying a vaporous or gaseous oxidant to the particles in the reactor; and (b5) performing one or more pump-purge cycles of the reactor using inert gas. In some embodiments, steps (b2)-(b5) are performed two or more times to increase the total thickness of the metal oxide layer before step (c) is performed.

In some embodiments, the reactor pressure is allowed to stabilize following step (b1), step (b2), and/or step (b4). In some embodiments, the reactor contents are agitated prior to and/or during step (b1), step (b3), and/or step (b5). In some embodiments, a subset of vapor or gaseous content is pumped out prior to step (b3) and/or step (b5). In some embodiments, step (b) takes place at a temperature between 35° C. and 50° C. In some embodiments, step (c) comprises combining the coated particles with one or more pharmaceutically acceptable excipients.

In some embodiments, the metal oxide layer has a thickness in range of 0.1 nm to 100 nm. In some embodiments, the metal oxide is selected from the group consisting of: zinc oxide, aluminum oxide, silicon oxide and titanium oxide. In some embodiments, the metal oxide is aluminum oxide. In some embodiments, the metal oxide is selected from the group consisting of aluminum oxide and titanium oxide. In some embodiments, the API is selected from the group consisting of ezetimibe, erlotinib and nifedipine. In some embodiments, the polymer is selected from the group consisting of HPMCAS, PVPVA and PVP.

In some embodiments, the coated particles in step (b) are less prone to agglomeration than the uncoated particles in step (a) during storage. In some embodiments, the coated particles in step (b) remain amorphous for a longer time than the uncoated particles in step (a) during storage. In some embodiments, the coated particles in step (b) are less hygroscopic than the uncoated particles in step (a). In some embodiments, the coated particles in step (b) show slower crystallization than the uncoated particles in step (a) during storage.

Some embodiments provide a pharmaceutical composition comprising coated particles comprising amorphous solid dispersion of an active pharmaceutical ingredient enclosed by one or more metal oxide layers, prepared by a method comprising the sequential steps of: (a) providing uncoated particle of an amorphous solid dispersion comprising an active pharmaceutical ingredient and a polymer; (b) performing atomic layer deposition to apply a metal oxide layer to uncoated particles of an amorphous solid dispersion comprising an active pharmaceutical ingredient and a polymer thereby preparing coated particles comprising an active pharmaceutical ingredient enclosed by one or more metal oxide layers; and (c) processing the coated particles to prepare a pharmaceutical composition.

In some embodiments, the step of performing atomic layer deposition comprises: (b1) loading the particles comprising the drug into a reactor; (b2) applying a vaporous or gaseous metal precursor to the particles in the reactor; (b3) performing one or more pump-purge cycles of the reactor using inert gas; (b4) applying a vaporous or gaseous oxidant to the particles in the reactor; and (b5) performing one or more pump-purge cycles of the reactor using inert gas.

In some embodiments, steps (b2)-(b5) are performed two or more times to increase the total thickness of the metal oxide layer before step (c) is performed. In some embodiments, the polymer and the active pharmaceutical ingredient are agitated prior to and/or during step (a). In some embodiments, the reactor pressure is allowed to stabilize following step (b1), step (b2), and/or step (b4). In some embodiments, the reactor contents are agitated prior to and/or during step (b1), step (b3), and/or step (b5). In some embodiments, a subset of vapor or gaseous content is pumped out prior to step (b3) and/or step (b5). In some embodiments, step (b) takes place at a temperature between 35° C. and 50° C.

In some embodiments, the metal oxide layer has a thickness in range of 0.1 nm to 100 nm. In some embodiments, the uncoated particles have a median particle size, on a volume average basis between 0.1 μm and 1000 μm.

In some embodiments, the coated particles comprising an active pharmaceutical ingredient further comprise one or more pharmaceutically acceptable excipients. In some embodiments, the uncoated particles consist of the active pharmaceutical ingredient.

In some embodiments, the metal oxide is selected from the group consisting of aluminum oxide and titanium oxide. In some embodiments, the API is selected from the group consisting of ezetimibe, erlotinib and nifedipine. In some embodiments, the polymer is selected from the group consisting of HPMCAS, PVPVA and PVP.

In some embodiments, the coated particles in step (b) are less prone to agglomeration than the uncoated particles in step (a) during storage. In some embodiments, the coated particles in step (b) remain amorphous for a longer time than the uncoated particles in step (a) during storage. In some embodiments, the coated particles in step (b) are less hygroscopic than the uncoated particles in step (a). In some embodiments, the coated particles in step (b) show slower crystallization than the uncoated particles in step (a) during storage.

Pharmaceutically Acceptable Excipients, Diluents, and Carriers

Pharmaceutically acceptable excipients include, but are not limited to:

(1) surfactants and polymers including: polyethylene glycol (PEG), polyvinylpyrrolidone (PVP), sodium lauryl sulfate, polyvinylalcohol, crospovidone, polyvinylpyrrolidone-polyvinylacrylate copolymer (PVPVA), cellulose derivatives, hydroxypropylmethyl cellulose, hydroxypropyl cellulose, carboxymethylethyl cellulose, hydroxypropyllmethyl cellulose phthalate, polyacrylates and polymethacrylates, urea, sugars, polyols, carbomer and their polymers, emulsifiers, sugar gum, starch, organic acids and their salts, (2) binding agents such as cellulose, cross-linked polyvinylpyrrolidone, microcrystalline cellulose;

(3) filling agents such as lactose monohydrate, lactose anhydrous, microcrystalline cellulose and various starches;

(4) lubricating agents such as agents that act on the flowability of a powder to be compressed, including colloidal silicon dioxide, talc, stearic acid, magnesium stearate, calcium stearate, silica gel;

(5) sweeteners such as any natural or artificial sweetener including sucrose, xylitol, sodium saccharin, cyclamate, aspartame, and acesulfame K;

(6) flavoring agents;

(7) preservatives such as potassium sorbate, methylparaben, propylparaben, benzoic acid and its salts, other esters of parahydroxybenzoic acid such as butylparaben, alcohols such as ethyl or benzyl alcohol, phenolic chemicals such as phenol, or quarternary compounds such as benzalkonium chloride;

(8) buffers;

(9) diluents such as pharmaceutically acceptable inert fillers, such as microcrystalline cellulose, lactose, dibasic calcium phosphate, saccharides, and/or mixtures of any of the foregoing;

(10) wetting agents such as corn starch, potato starch, maize starch, and modified starches, and mixtures thereof;

(11) disintegrants; such as croscarmellose sodium, crospovidone, sodium starch glycolate; and

(12) effervescent agents such as effervescent couples such as an organic acid (e.g., citric, tartaric, malic, fumaric, adipic, succinic, and alginic acids and anhydrides and acid salts), or a carbonate (e.g., sodium carbonate, potassium carbonate, magnesium carbonate, sodium glycine carbonate, L-lysine carbonate, and arginine carbonate) or bicarbonate (e.g. sodium bicarbonate or potassium bicarbonate).

EXAMPLES

The following materials and methods were used in the Examples.

To apply an aluminum oxide coating, the vaporous or gaseous metal precursor was tri-methyl aluminum (TMA), the byproduct gaseous methane forms after TMA reacts with exposed hydroxyl groups on the particles or on surface of the coated particles, and the oxidant is water vapor.

Method for ALD Coating

In brief, the method for creating an $Al_2O_3$ coating comprised the sequential steps of:

(a) loading particles comprising the drug into a reactor;

(b) reducing the reactor pressure to less than 1 Torr;

(c) agitating the reactor contents until the reactor contents has a desired water content by performing residual gas analysis (RGA) to monitor levels of water vapor in the reactor;

(d) pressurizing the reactor to at least 1 Torr by adding a vaporous or gaseous TMA;

(e) allowing the reactor pressure to stabilize;

(f) agitating the reactor contents;

(g) pumping out a subset of vapor or gaseous content, including gaseous methane and unreacted TMA, and determining when to stop pumping by performing RGA to monitor levels of gaseous methane and unreacted TMA in the reactor;

(h) performing a sequence of pump-purge cycles on the reactor using nitrogen gas;

(i) pressuring the reactor to at least 1 Torr by adding water vapor;

(j) allowing the reactor pressure to stabilize;

(k) agitating the reactor contents;

(l) pumping out a subset of vapor or gaseous content, including water vapor, and determining when to stop pumping by performing RGA to monitor levels of water vapor in the reactor; and (m) performing a sequence of pump-purge cycles on the reactor using nitrogen gas.

In some cases, the steps of (b)-(m) were repeated more than once to increase the total thickness of the metal oxide that enclose the drug particle core. A $TiO_2$ coating can be applied by a similar process using $TiCl_4$.

Example 1: Metal Oxide Coated ASD Particles are Resistant to Crystallization, Exhibit Less Agglomeration and Have Improved Compressibility and Flowability Compared to Uncoated ASD Particles Particles of an ASD of ezetimibe in hydroxypropyl methyl cellulose acetate succinate (HPMCAS) with 50% or 70% drug loading, were prepared by spray drying. The particles with 50% (B3-140 and B3-141) or 70% (B3-139A, B3-138B and B3-139B) drug loading were coated with aluminum oxide by ALD at 35° C., essentially as described above. The ASD particles received an approximately 5 nm thick (B3-140 and B3-139A), an approximately 15-20 nm thick (B3-138B) or an approximately 20-30 nm think coating (B3-141 and B3-139B). The size distribution of the various ASD particles is shown in Table 1.

TABLE 1

| | Size (μm) | | |
|---|---|---|---|
| Sample | $D_{10}$ | $D_{50}$ | $D_{90}$ |
| 50% Uncoated | 1.5 ± 0.0 | 11.4 ± 0.5 | 769.3 ± 69.1 |
| B3-140 | 1.9 ± 0.0 | 11.7 ± 0.5 | 784.7 ± 67.9 |
| B3-141 | 2.5 ± 0.0 | 13.6 ± 0.1 | 864.0 ± 14.4 |
| 70% Uncoated | 3.3 ± 0.0 | 28.2 ± 1.4 | 663.3 ± 45.2 |
| B3-139A | 3.1 ± 0.0 | 15.8 ± 0.3 | 603.7 ± 13.8 |
| B3-138B | 3.7 ± 0.0 | 22.5 ± 0.7 | 509.7 ± 22.8 |
| B3-139B | 3.5 ± 0.1 | 27.8 ± 2.5 | 744.3 ± 80.5 |

Figure 2:
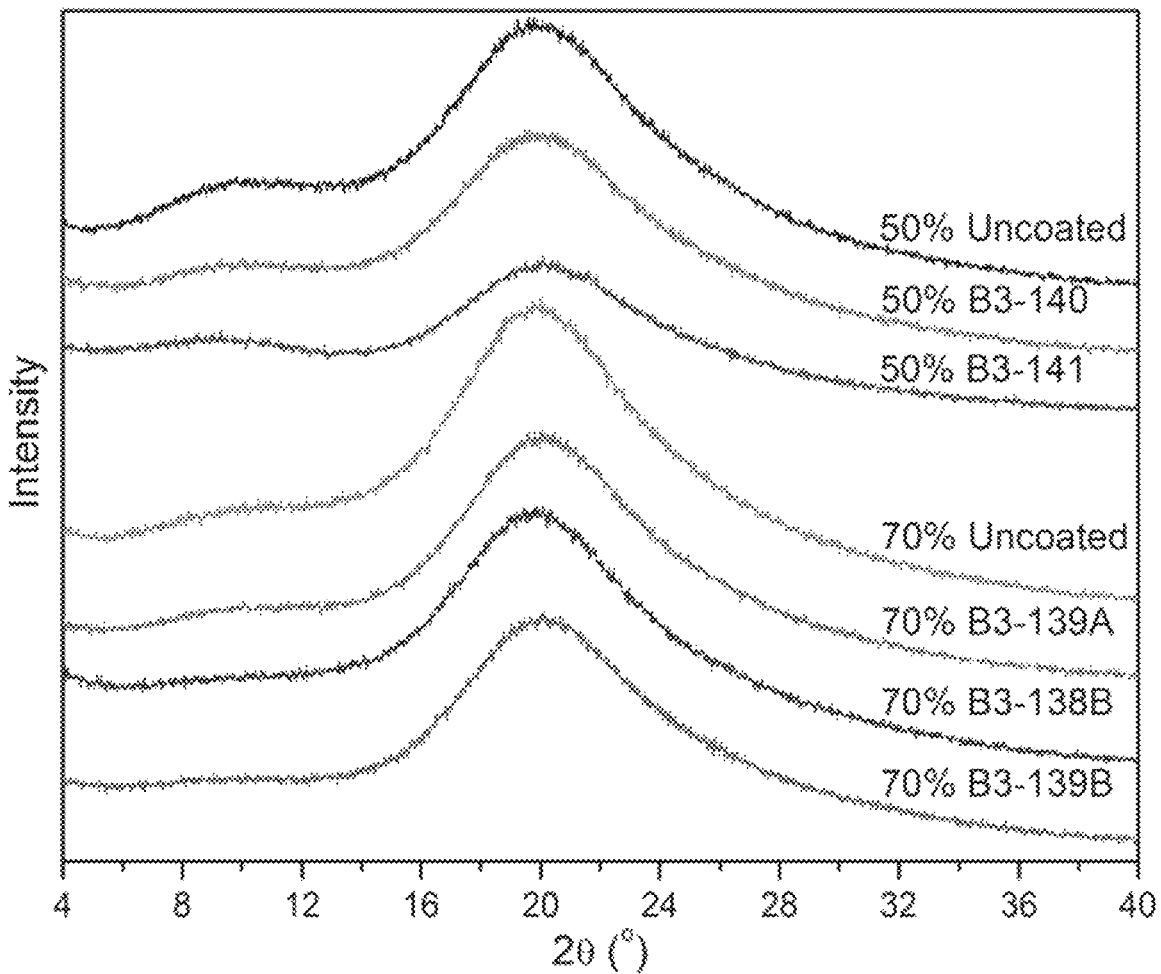
FIG. 2 depicts the results of x-ray diffraction analysis of uncoated and metal oxide coated ASD particles.
Figure 3:
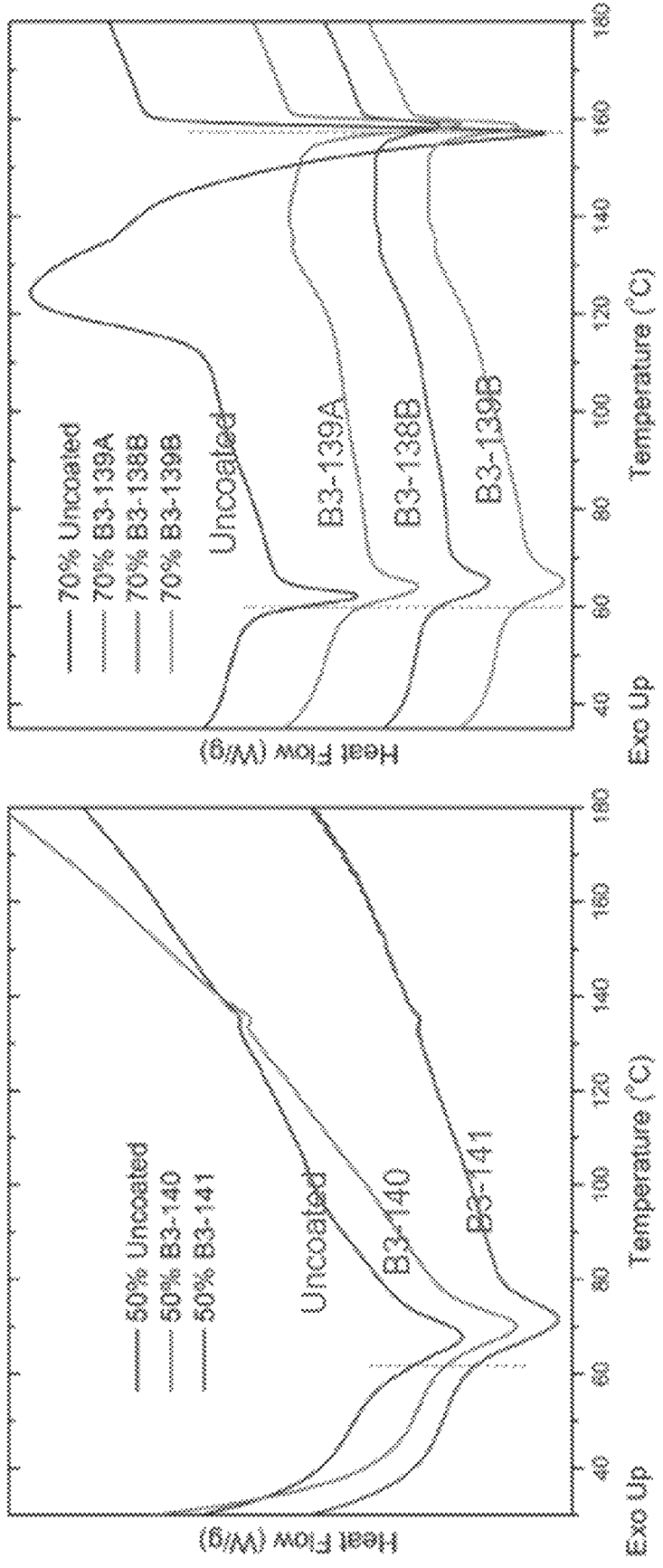
FIG. 3 depicts the results of differential scanning calorimetry (DSC) analysis of uncoated and metal oxide coated ASD particles.

X-ray diffraction was used to assess the coated and uncoated ASD particles. As shown in FIG. 2, x-ray diffraction analysis showed that the coated and uncoated ASD particles where amorphous. Thermal analysis was used to assess the glass transition temperature (Tg) and thermal-induced crystallization of the coated and uncoated ASD particles. As can be seen in FIG. 3, the coated ASD particles appeared to have a higher glass transition temperature (Tg) than the uncoated ASD particles. As can also be seen, particularly for the ASD particles with 70% drug loading, the coating dramatically decreased thermal-induced crystallization.

Figure 4A:
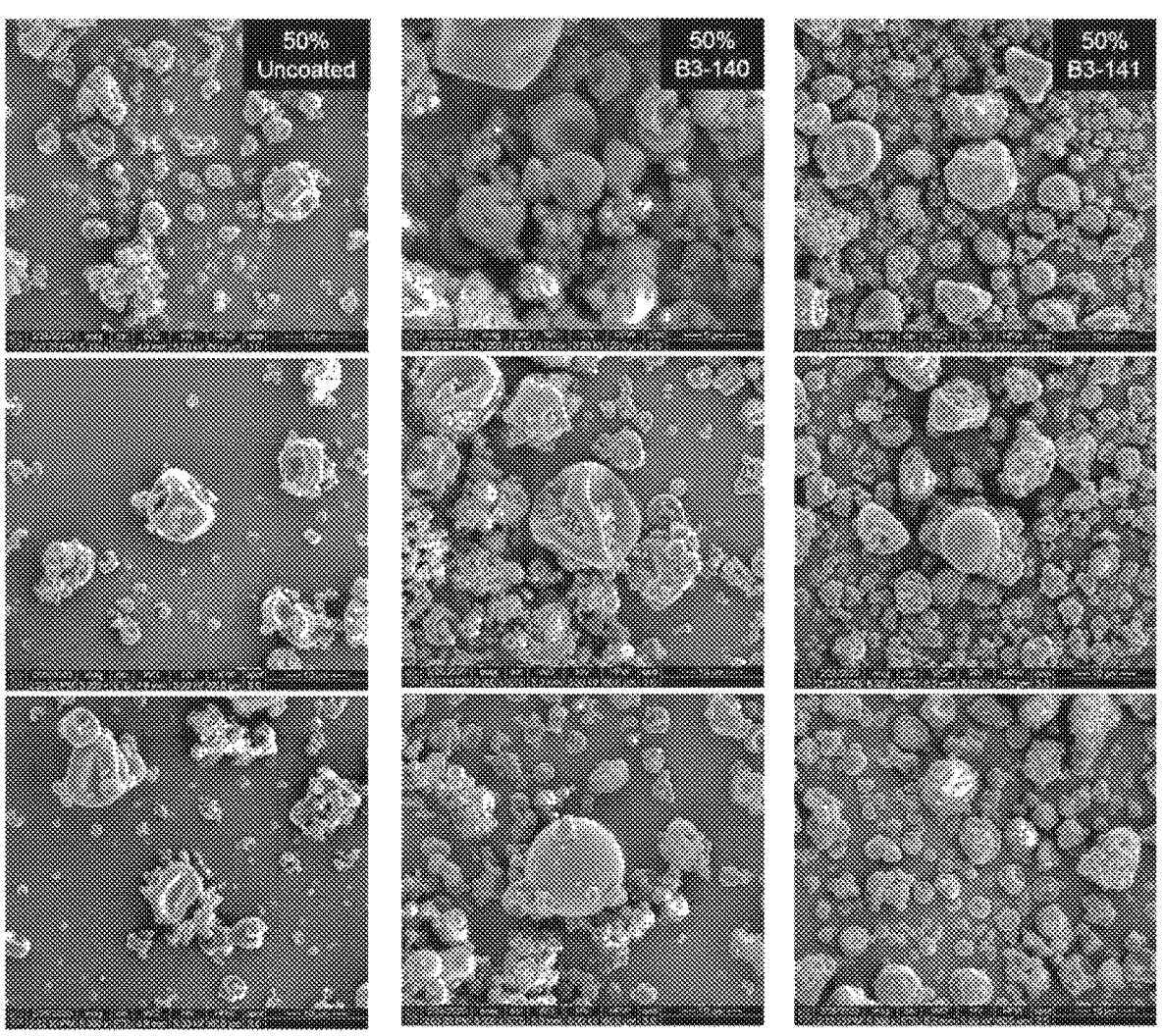
FIGS. 4A-4B depict scanning electron microscopy images of uncoated and metal oxide coated ASD particles.
Figure 4B:
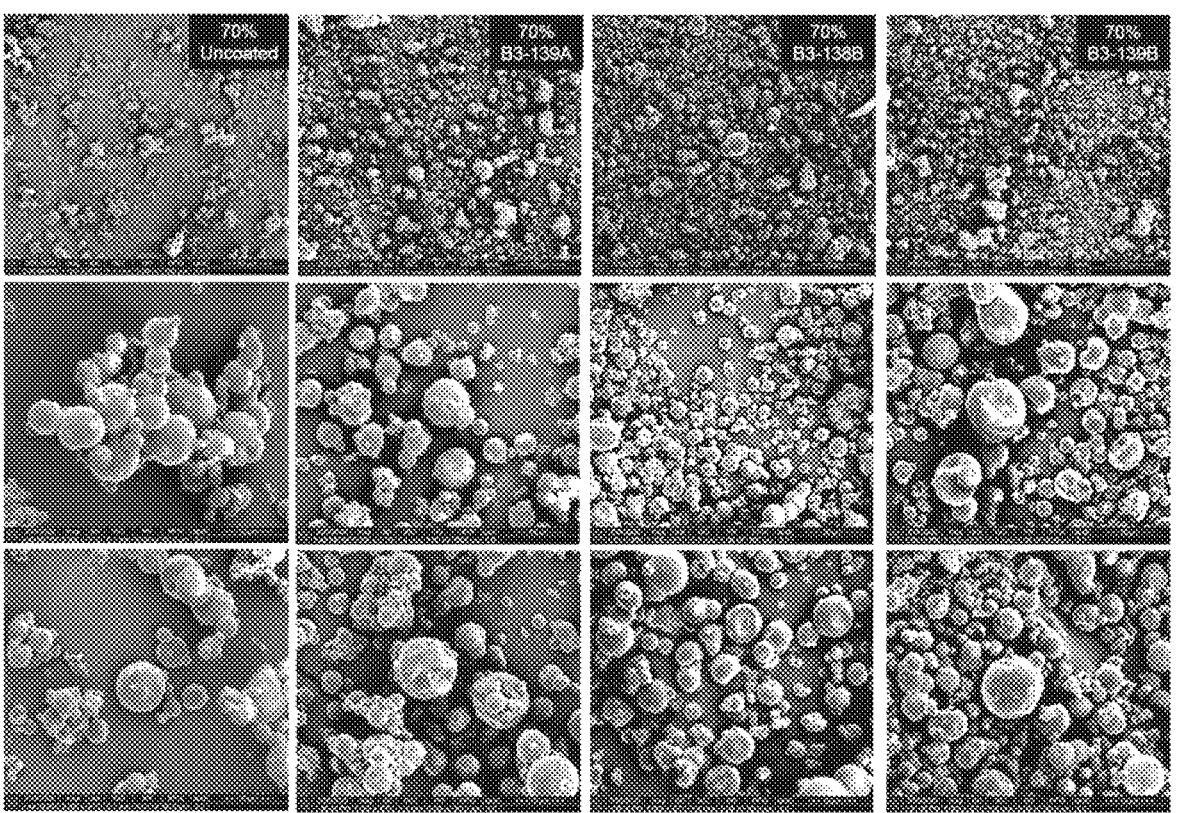

Scanning electron microscopy was used to assess the morphology of the coated and uncoated ASD particles. As can be seen in FIG. 4, the coated ASD particles were less agglomerated than the uncoated ASD particles.

The compressibility and the flowability of the coated and uncoated ASD particles were measured. As can be seen in FIG. 5, the coating improved the compressibility and flowability of the ASD particles.

Figure 6:
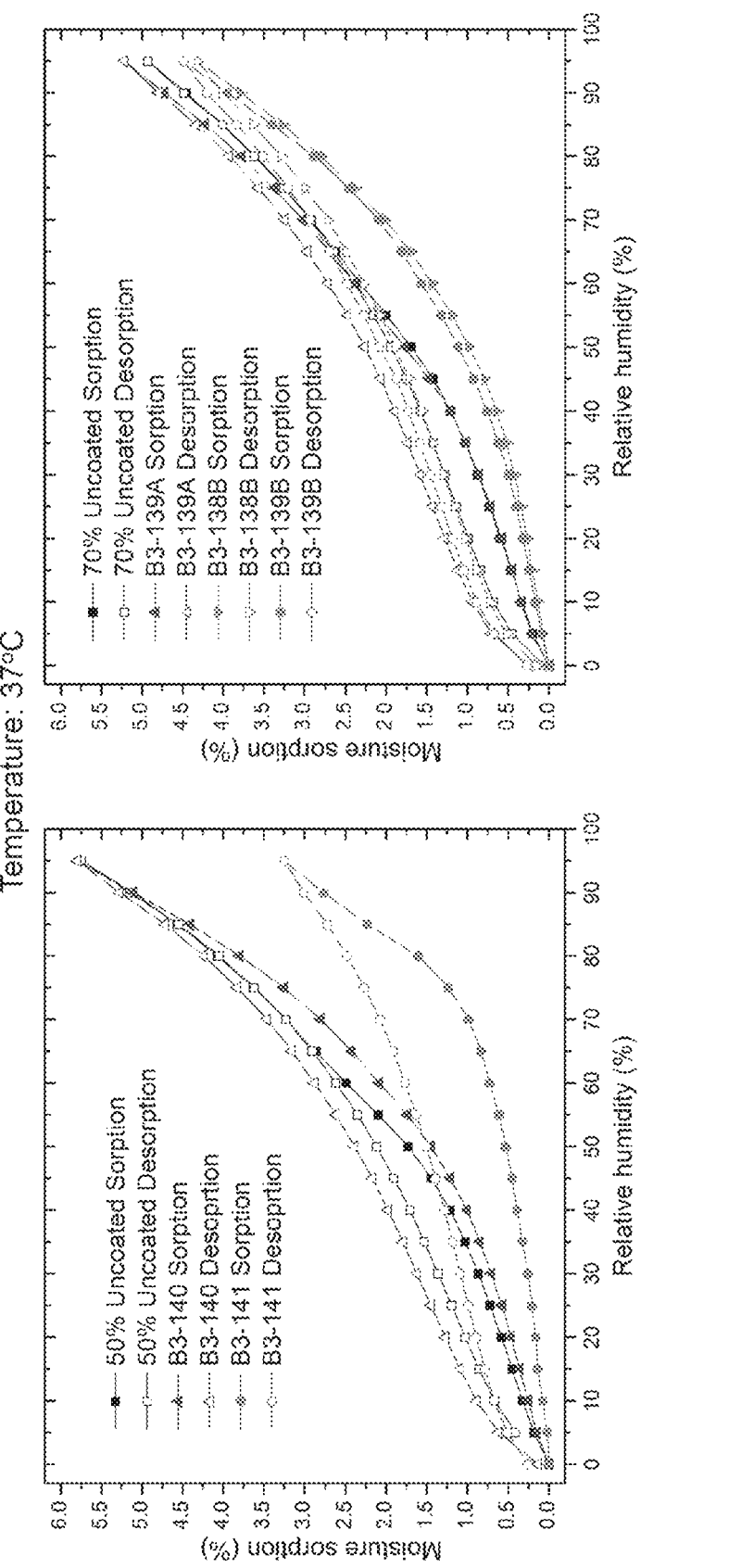
FIG. 6 depicts the results of moisture absorption analysis of uncoated and metal oxide coated ASD particles.

Isothermal moisture sorption was used to assess the moisture absorption tendency of the coated and uncoated ASD particles. As can be seen in FIG. 6, the coated ASD particles were less hygroscopic than the uncoated ASD particles.

Figure 7A:
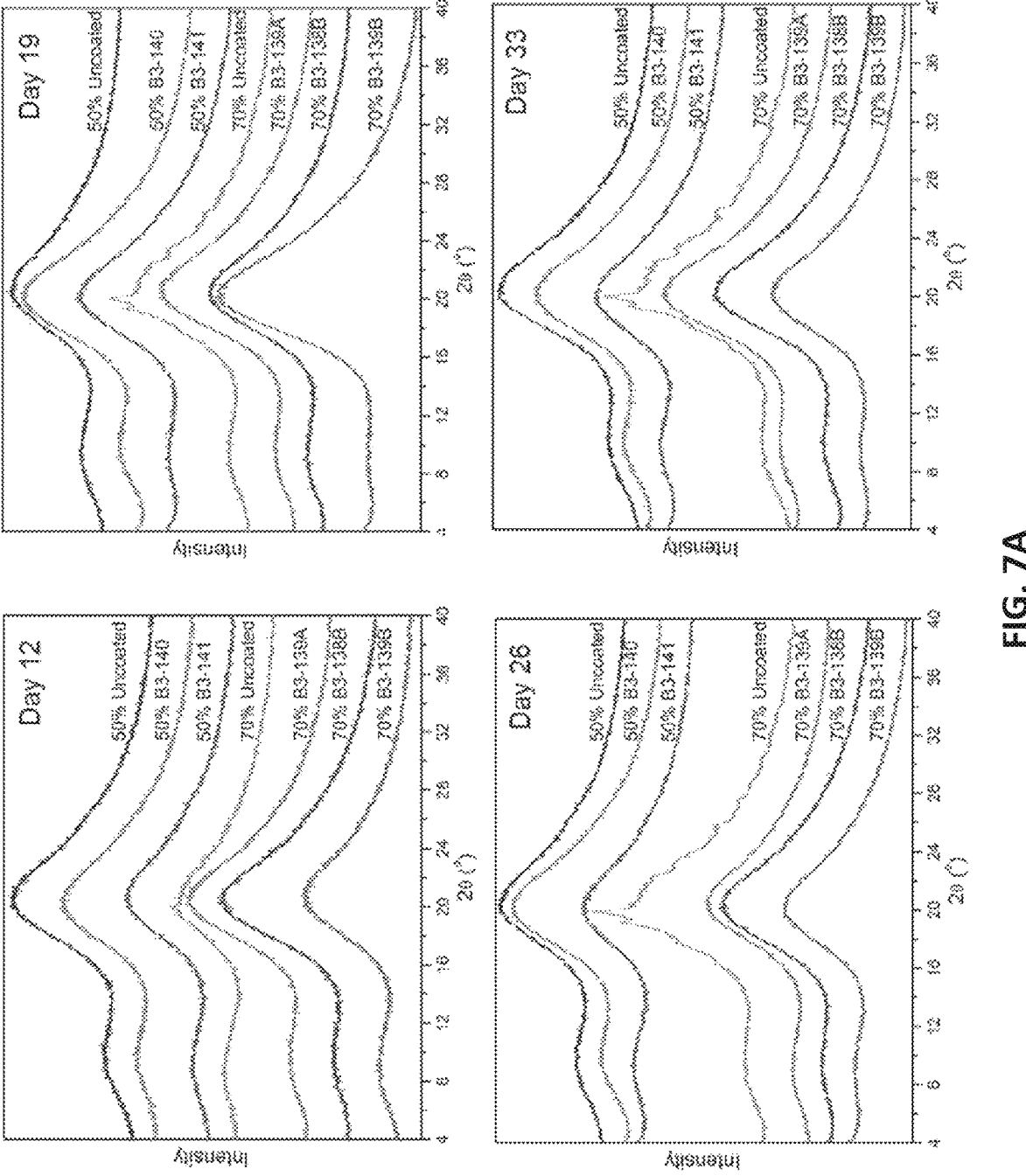
FIGS. 7A-7B depict the results of x-ray diffraction analysis of uncoated and metal oxide coated ASD particles under accelerated stability testing.
Figure 7B:
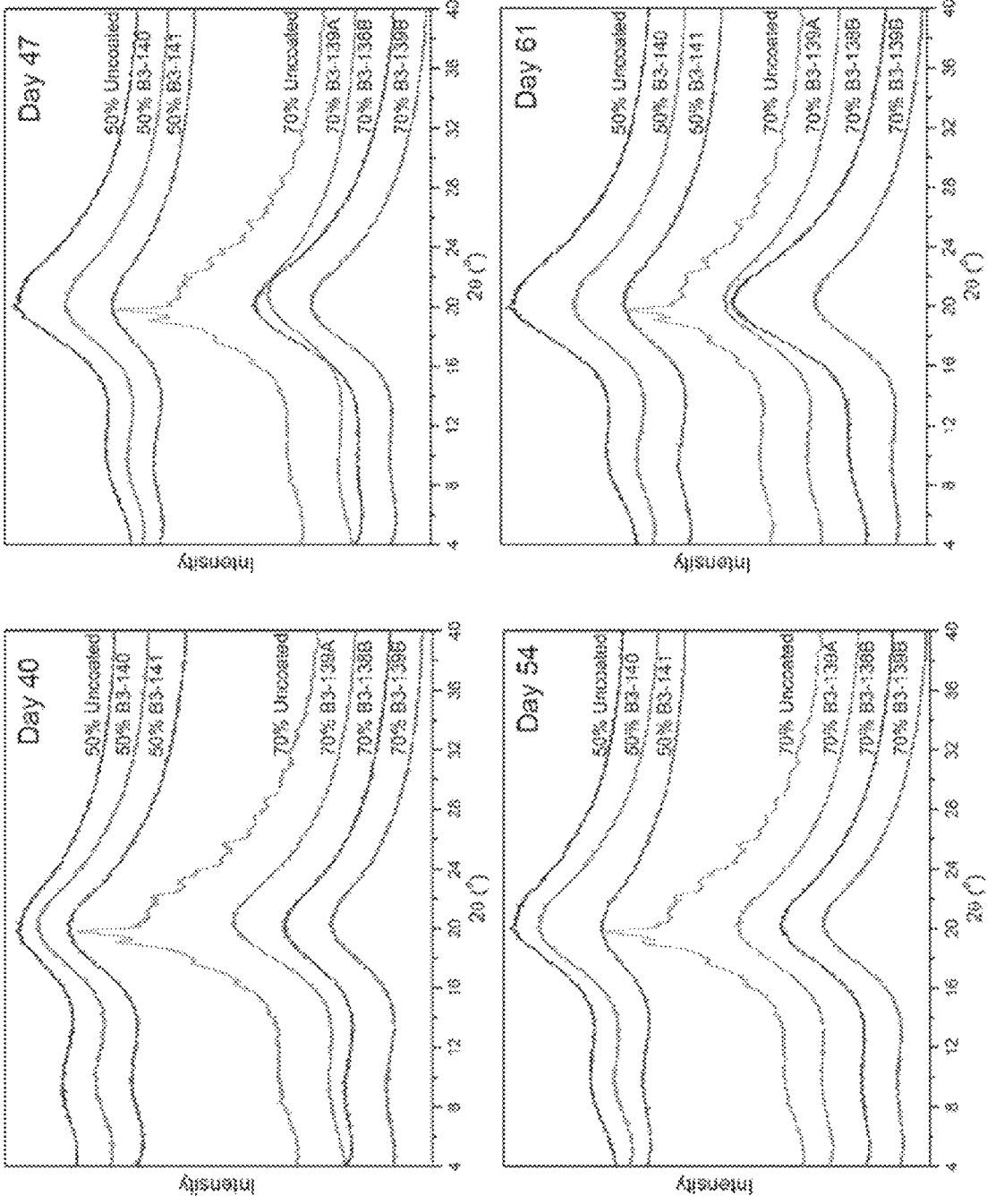
Figure 8:
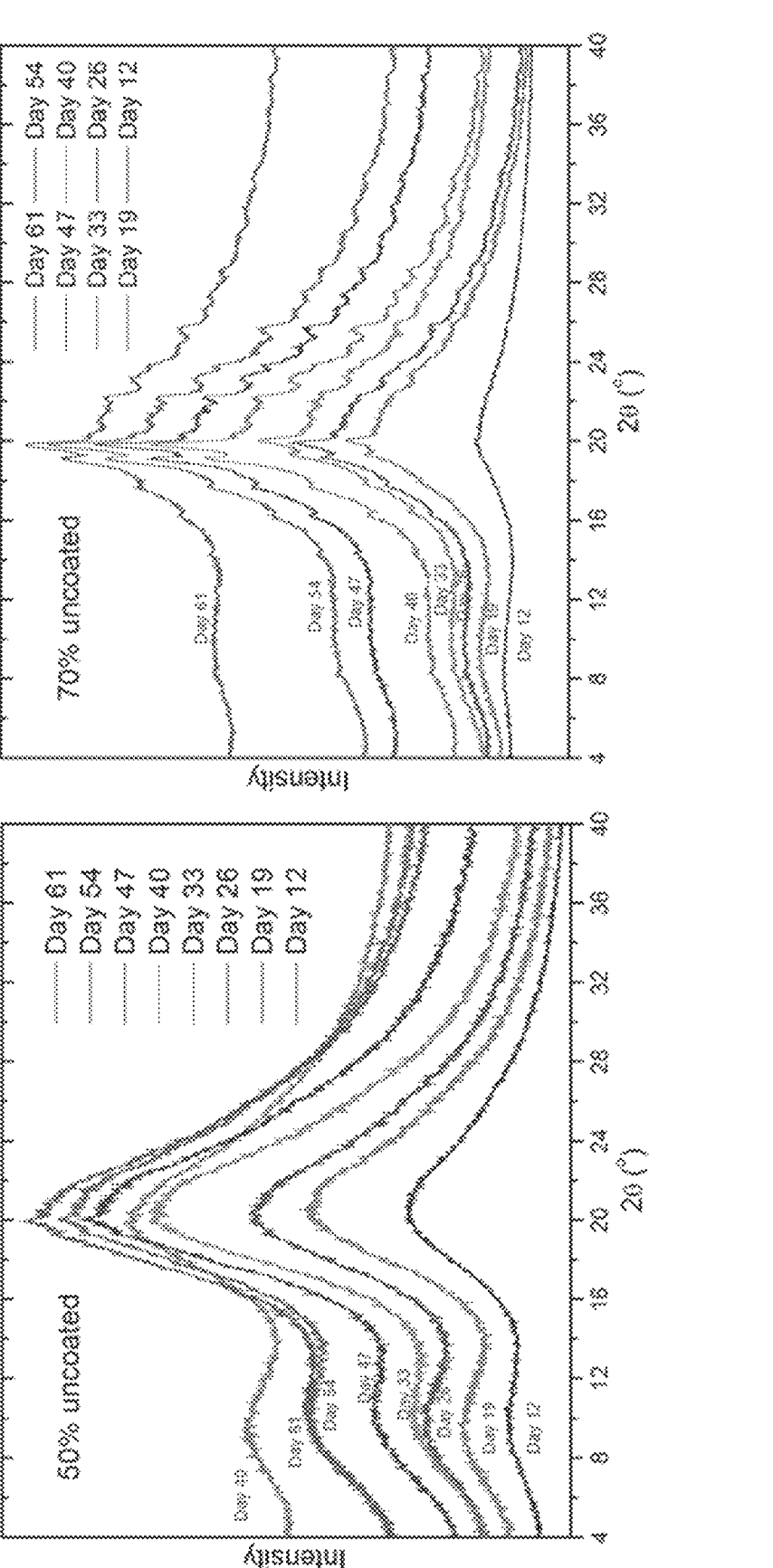
FIG. 8 depicts the results of x-ray diffraction analysis of uncoated ASD particles under accelerated stability testing.

Example 2: Metal Oxide Coated ASD Particles are Resistant to Crystallization in Accelerated Stability Study Conditions The coated and uncoated ASD particles of Example 1 were subjected to an accelerated stability study. The coated and uncoated ASD particles were stored at 40° C./75% relative humidity. Samples of the coated and uncoated ASD particles were analyzed by x-ray diffraction at Days 12, 19, 26, 33, 40, 47, 54 and 61. As can be seen in FIG. 7, the uncoated ASD particles became increasingly crystalline, particularly the 70% drug loading ASD particles, while the coated ASD particles remained essentially amorphous. FIG. 8 presents the x-ray diffraction data for just the uncoated ASD particles. Here the increasing crystallinity of these ASF particles can be seen more readily.

Figure 9A:
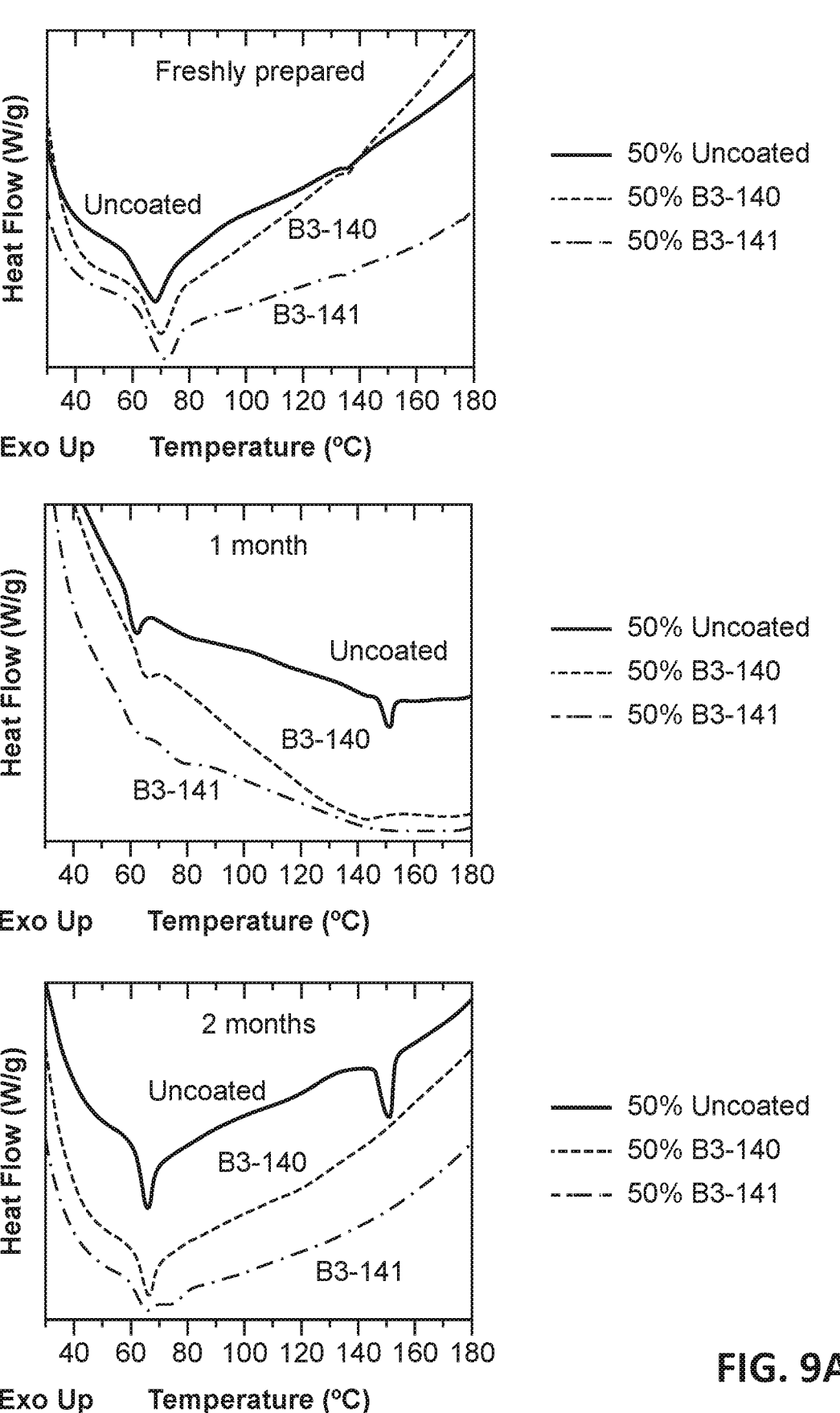
FIGS. 9A-9B depict the results of differential scanning calorimetry (DSC) analysis of uncoated and metal oxide coated ASD particles under accelerated stability testing.
Figure 9B:
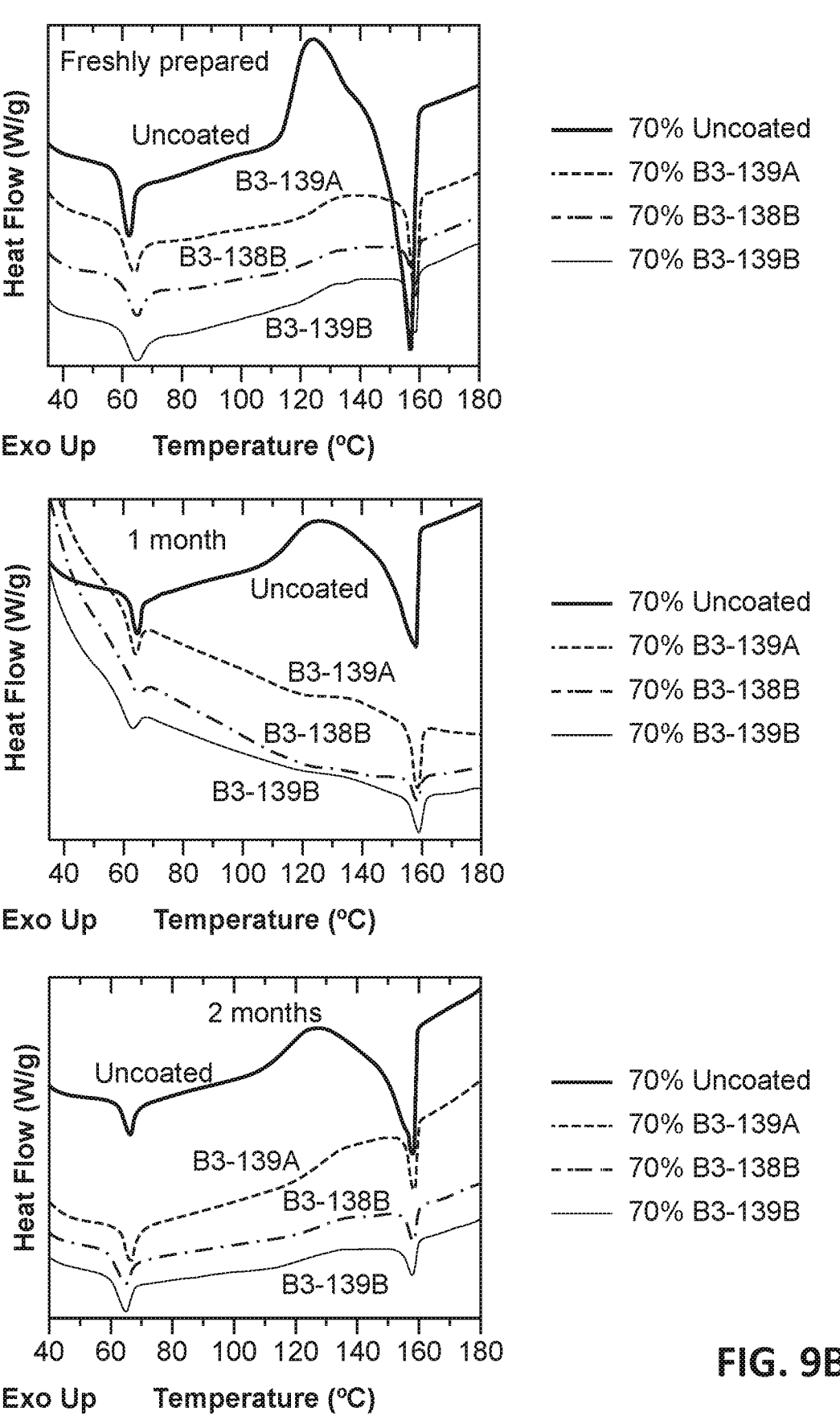
Figure 10A:
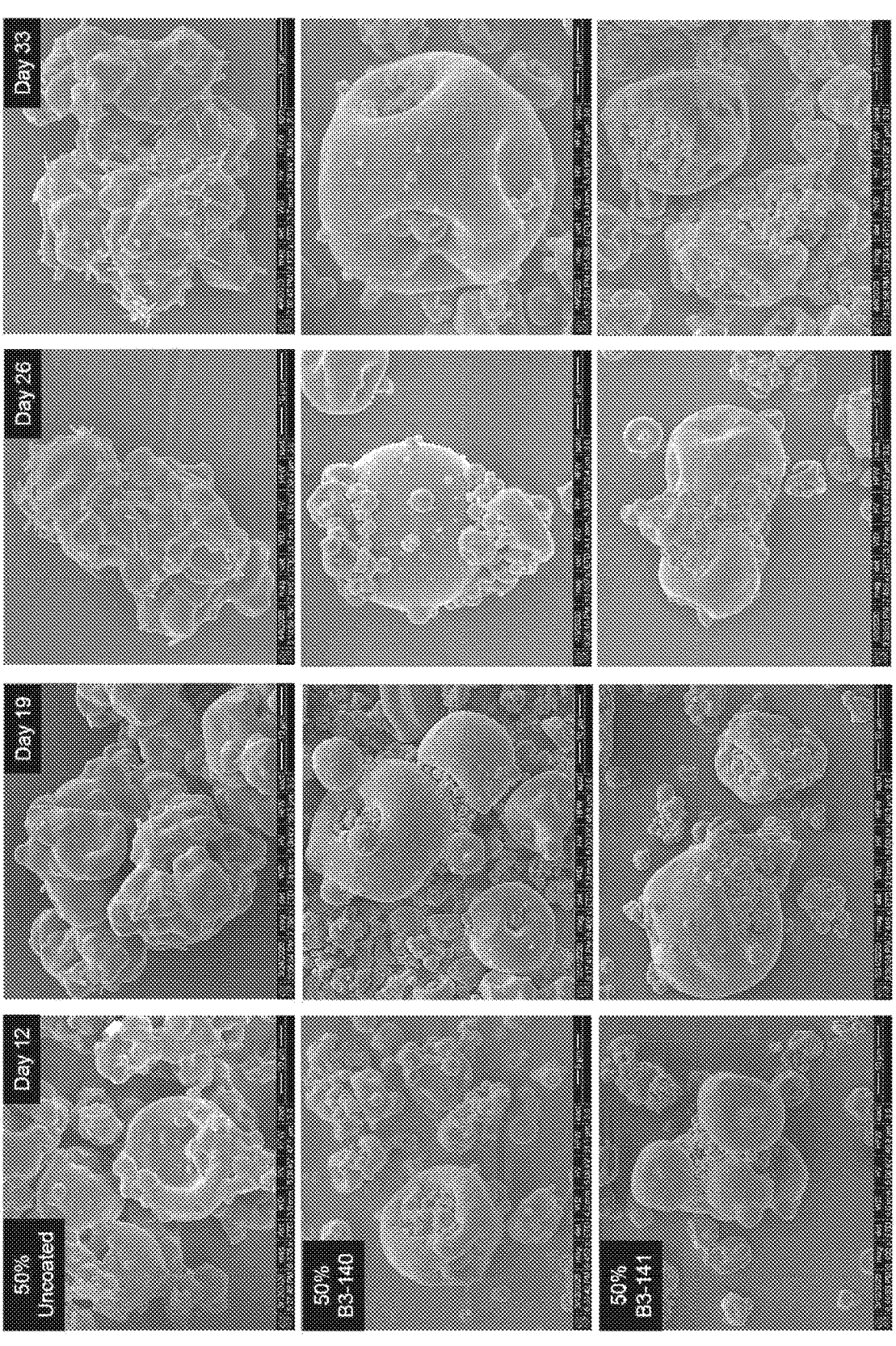
FIGS. 10A-10B depict scanning electron microscopy images of uncoated and metal oxide coated ASD particles under accelerated stability testing.
Figure 10B:
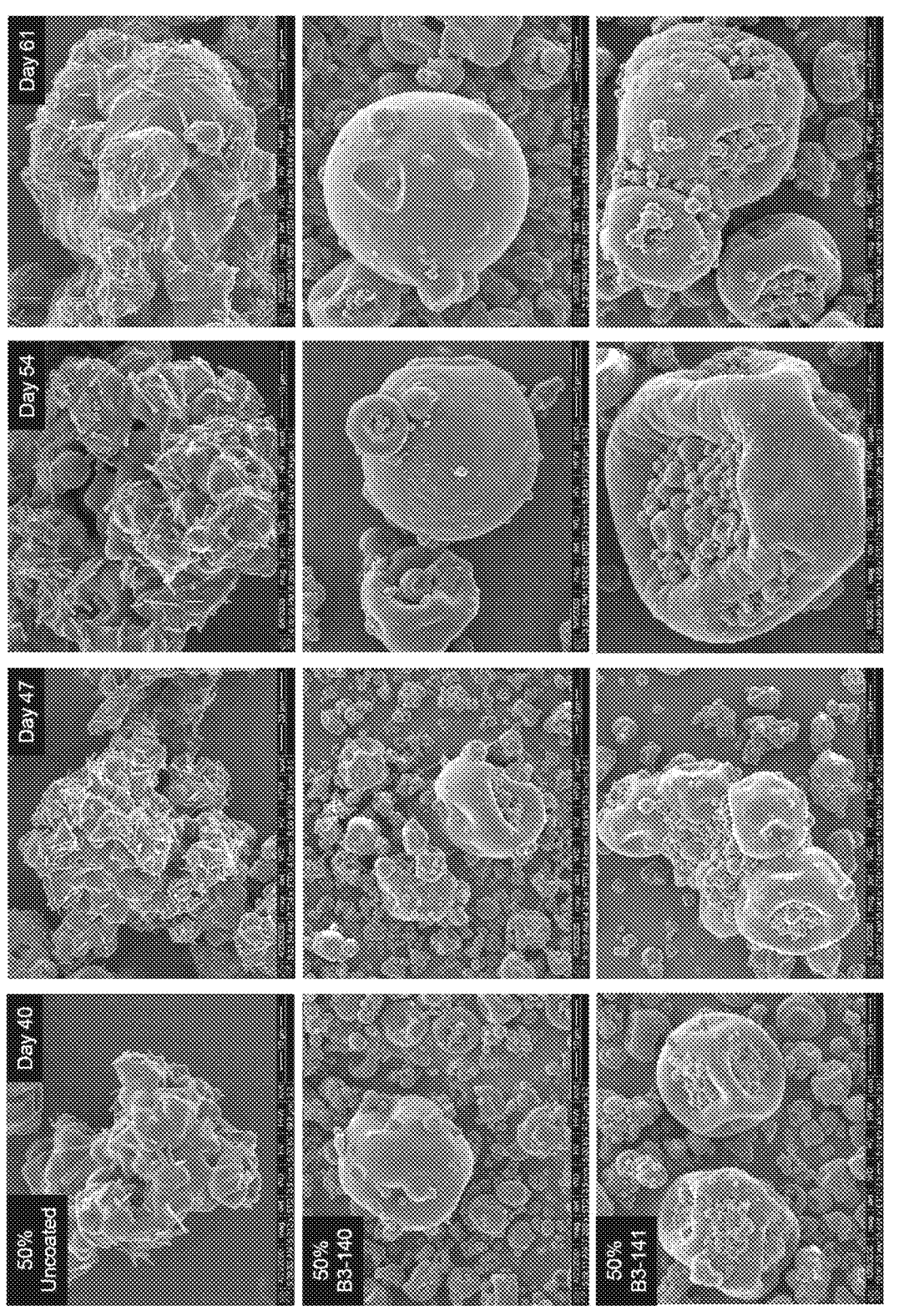
Figure 11A:
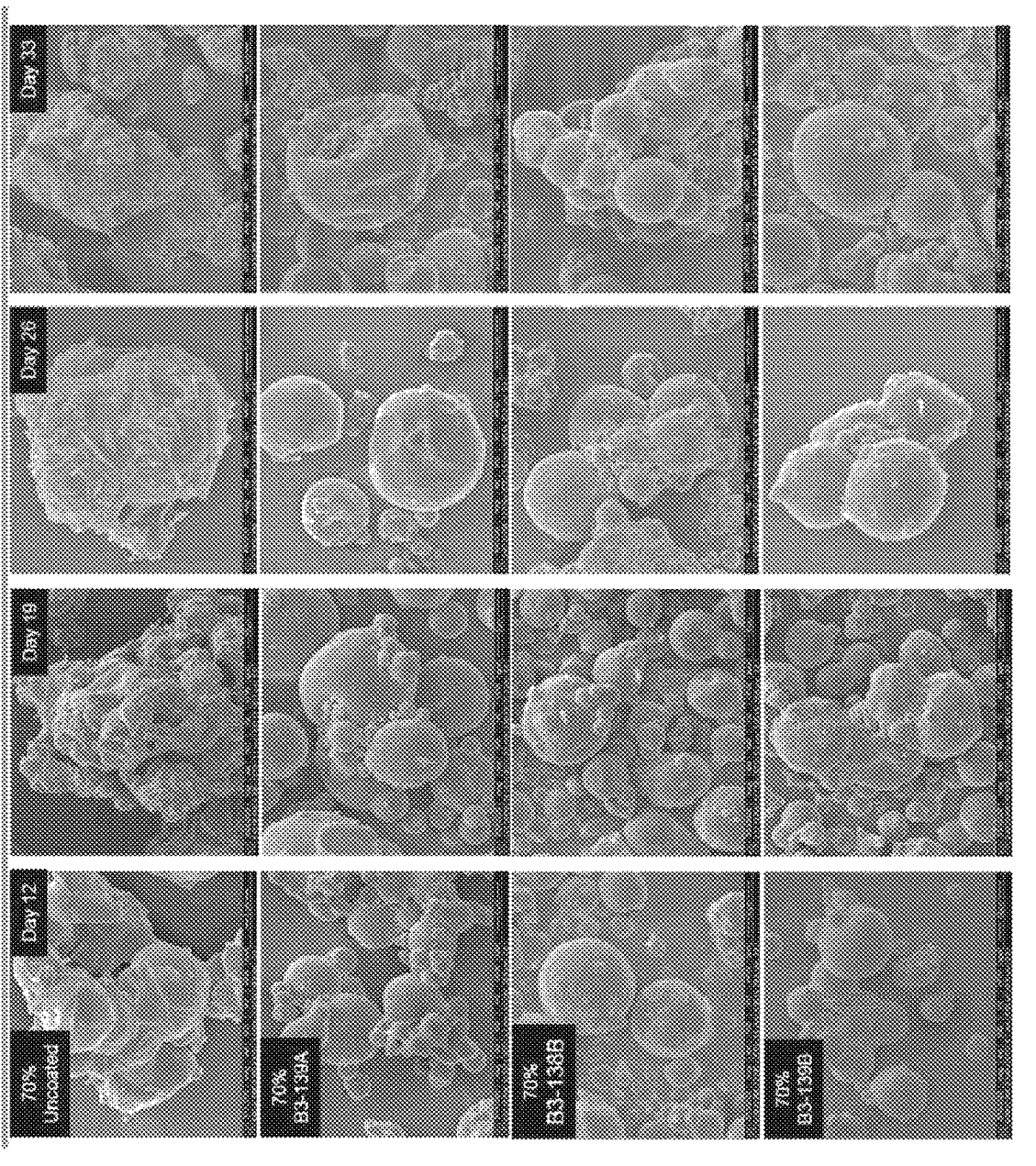
FIGS. 11A-11B depict scanning electron microscopy images of uncoated and metal oxide coated ASD particles under accelerated stability testing.
Figure 11B:
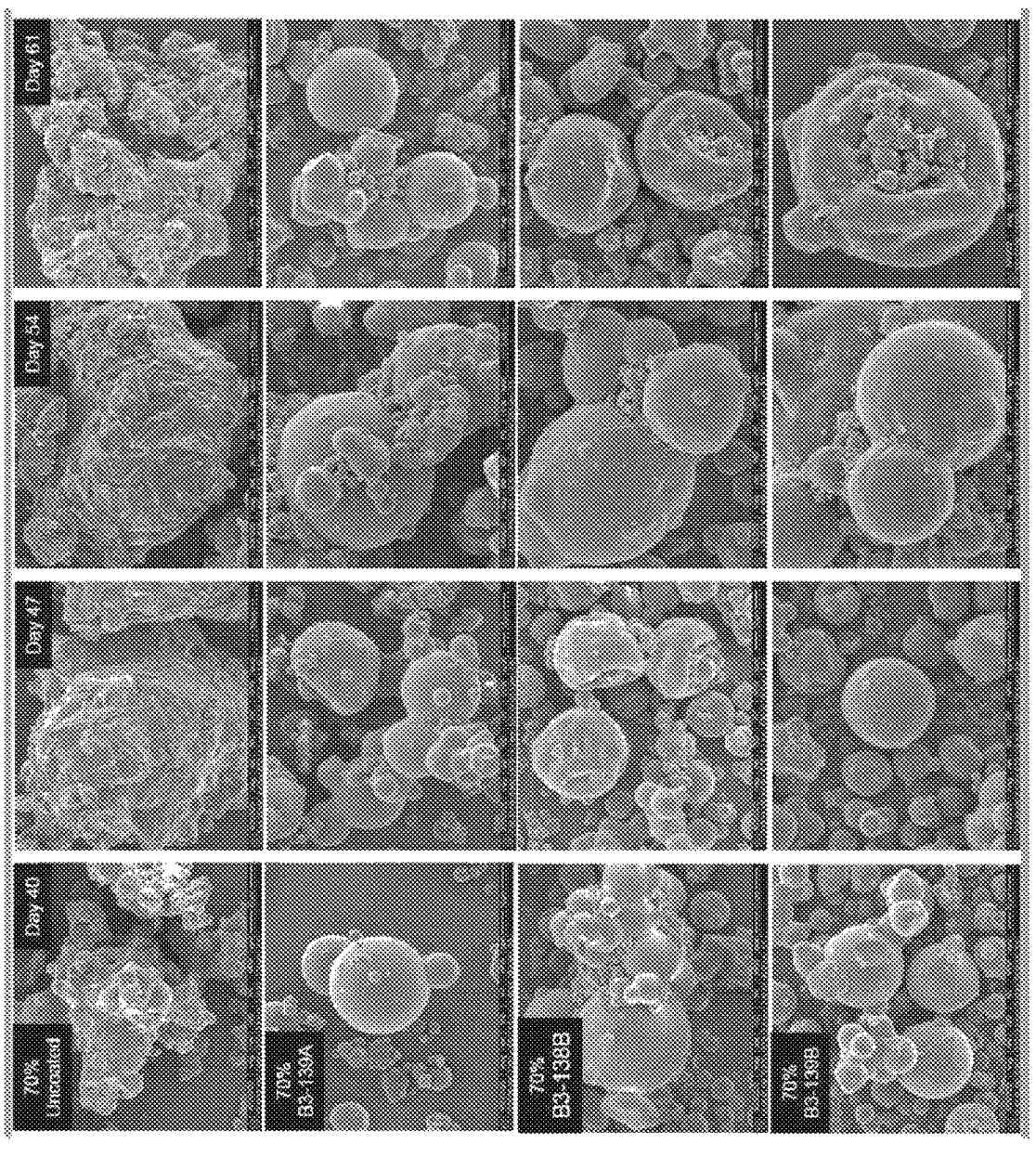

Thermal analysis was used to assess the thermal-induced crystallization of the coated and uncoated ASD particles subjected to the accelerated stability study. As can be seen in FIG. 9, the coated ASD samples appeared to have a higher glass transition temperature (Tg) than the uncoated ASD samples. As can also be seen in FIG. 9, even at 50% drug loading, the uncoated ASD particles exhibited thermal induced crystallization after only 1 month. The coated ASD particles exhibited little change in thermal induced crystallization even after 2 months.

Scanning electron microscopy was used to assess the morphology of the coated and uncoated ASD particles. As can be seen in FIGS. 10A-10B and FIG. 11A-11B, crystals are visible on the surface of the uncoated 50% drug loading ASD particles at day 17 and on the uncoated 70% drug loading ASD particles at day 12. In contrast, crystals were not visible on surface of the coated ASD particles even after 61 under accelerated stability conditions.

Figure 14:
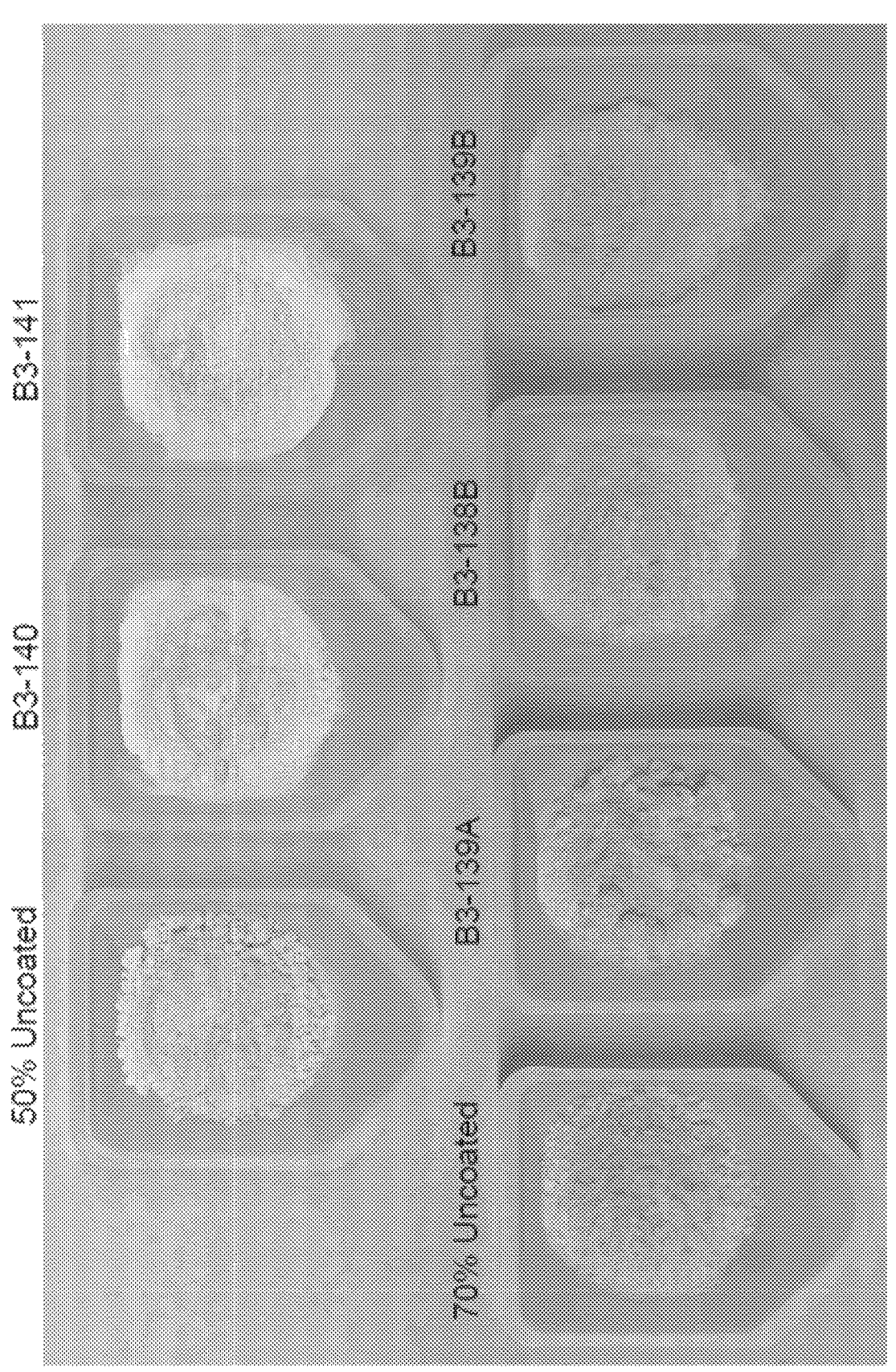
FIG. 14 depicts the appearance of the uncoated and metal oxide coated ASD particles (aluminum oxide/ezetimibe/HPMCAS) after 8 month storage at 40° C. and 75% relative humidity.

The coated and uncoated ASD particles of Example 1 (aluminum oxide/ezetimibe/HPMCAS) were subjected to an accelerated stability study under open condition (8 month storage at 40° C. and 75% relative humidity). As can be seen in FIG. 14, uncoated ASD particles (50% and 70% drug loading) show darker color (yellow) comparing to coated ASD particles. Also, uncoated ASD (50% and 70% drug loading) show more agglomeration comparing to thin coated ASD (B3-139A). There is no agglomeration for intermediate coated ASD (B3-139B) and thick coated ASD (B3-141 and B3-139B).

Figure 15:
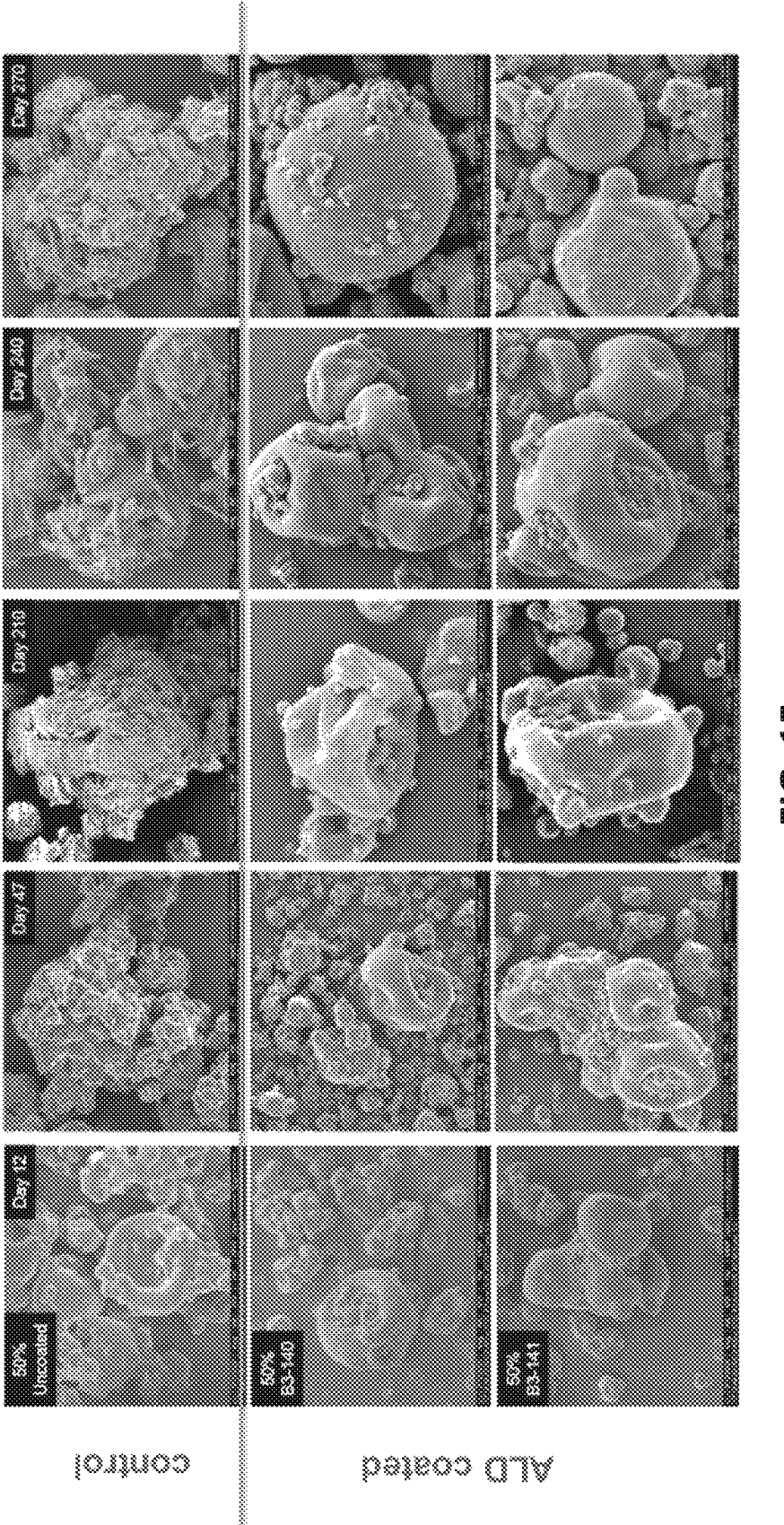
FIG. 15 depicts scanning electron microscopy images of uncoated and metal oxide coated 50% DL (drug loaded) ASD particles (aluminum oxide/ezetimibe/HPMCAS) after storage at 40° C. and 75% relative humidity for different periods (day 12, day 47, day 210, day 240 and day 270).

The samples were also assessed by scanning electron microscopy (SEM) to assess the particle morphology of uncoated and metal oxide coated 50% DL (drug loaded) ASD particles (aluminum oxide/ezetimibe/HPMCAS) after storage at 40° C. and 75% relative humidity for different periods (day 12, day 47, day 210, day 240 and day 270). As shown in FIG. 15, while crystallization started before day 47 for uncoated ASD, there was no crystallization for the ALD coated ASD (50% B3-140 and 50% B3-141) throughout the 9 month storage duration.

Figure 16:
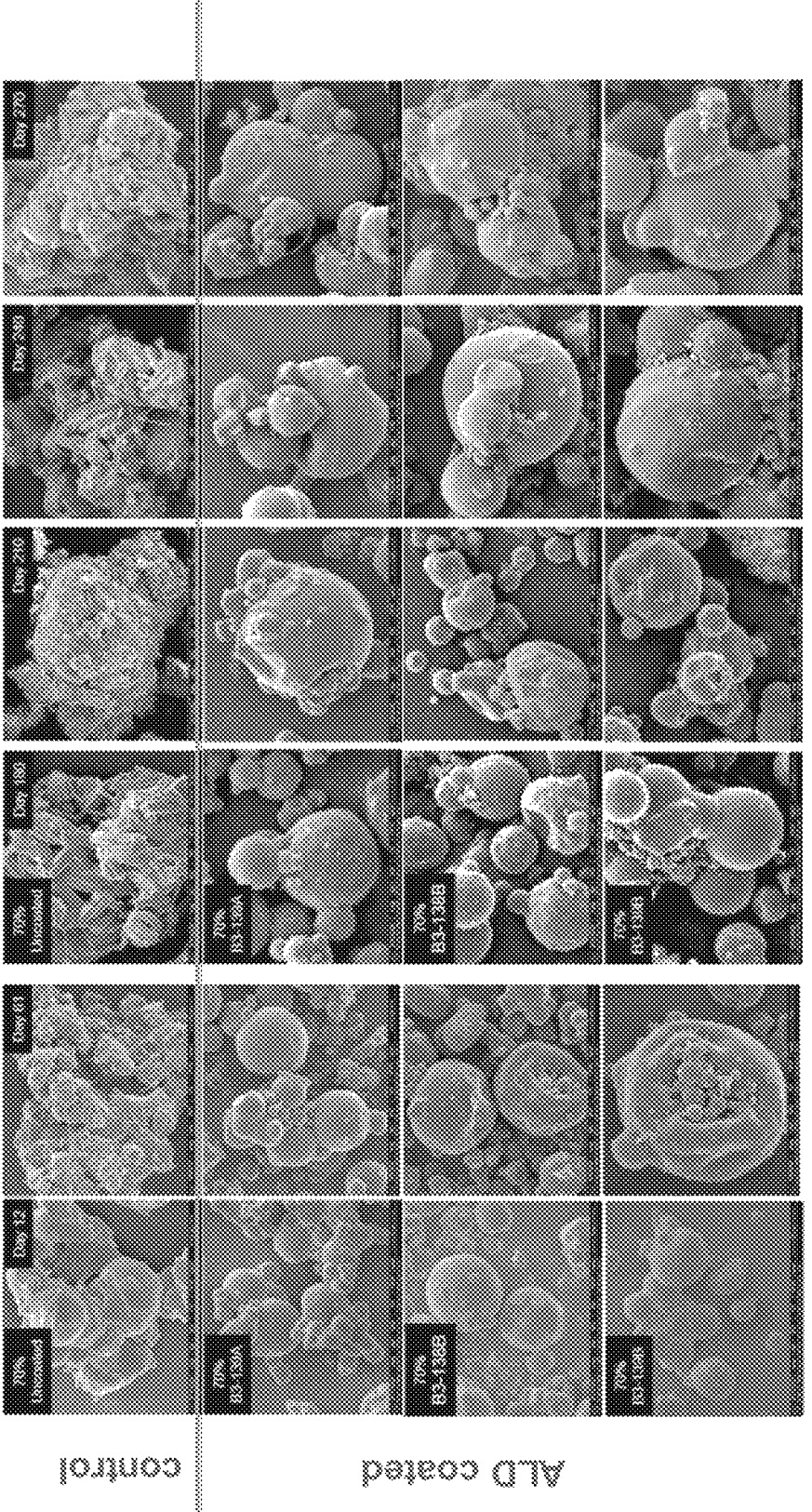
FIG. 16 depicts scanning electron microscopy images of uncoated and metal oxide coated 70% DL ASD particles (aluminum oxide/ezetimibe/HPMCAS) after storage at 40° C. and 75% relative humidity for different periods (day 12, day 61, day 180, day 210, day 240 and day 270).

The samples were also assessed by scanning electron microscopy (SEM) to assess the particle morphology of uncoated and metal oxide coated 70% DL ASD particles (aluminum oxide/ezetimibe/HPMCAS) after storage at 40° C. and 75% relative humidity for different periods (day 12, day 61, day 180, day 210, day 240 and day 270). As shown in FIG. 16, while crystallization started as early as day 12 for uncoated ASD, there was no crystallization for the thin coated ASD (70% B3-139A) until 7 month (day 210) and there was no crystallization for the thick coated ASD (70% B3-138B and 70% B3-139B) throughout the 9 month storage duration.

Figure 17A:
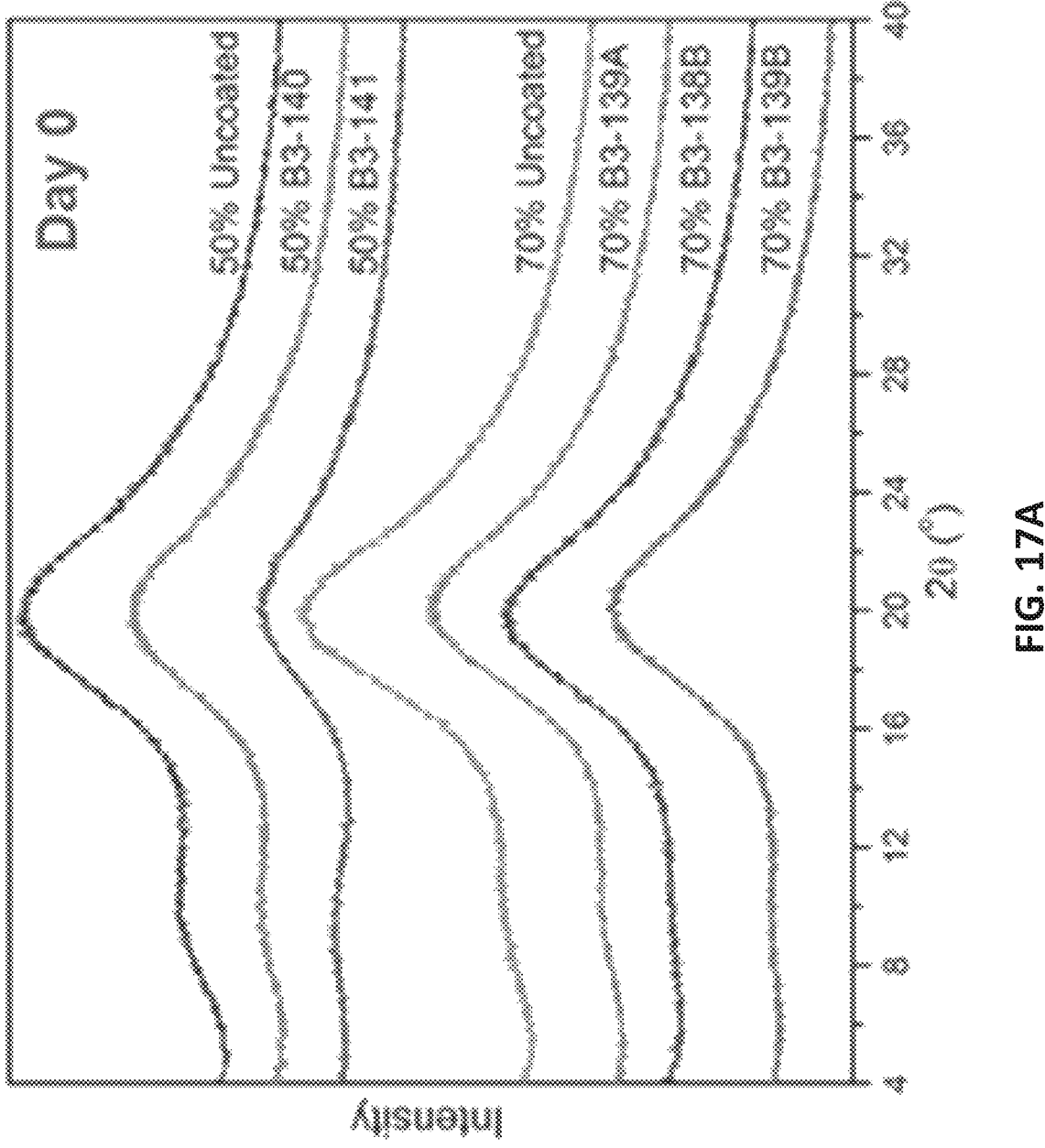
FIGS. 17A-17C depict the results of x-ray diffraction analysis of uncoated and metal oxide coated ASD particles (aluminum oxide/ezetimibe/HPMCAS) after 9 month storage at 40° C. and 75% relative humidity. As shown in FIG.
Figure 17B:
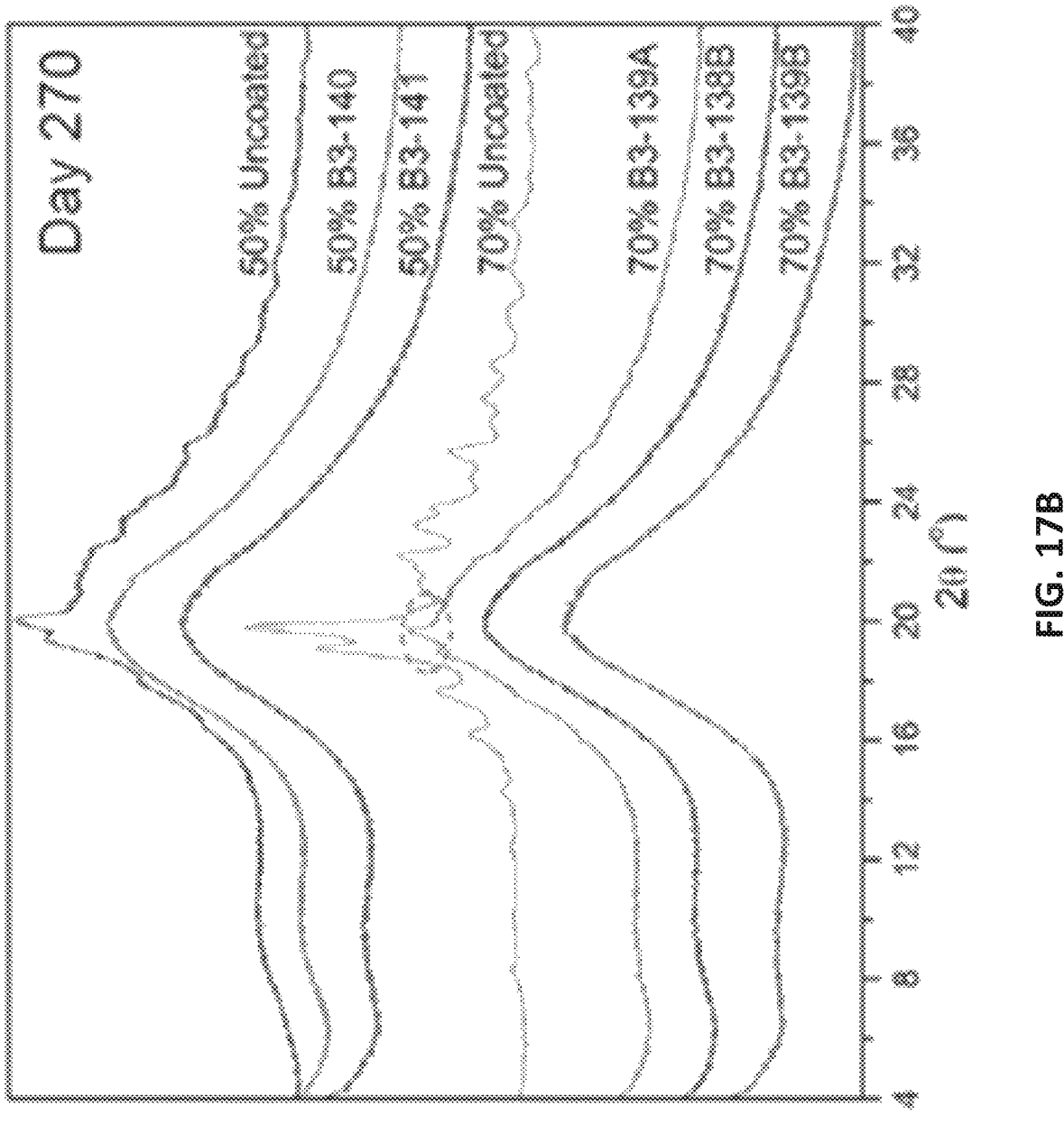
Figure 17C:
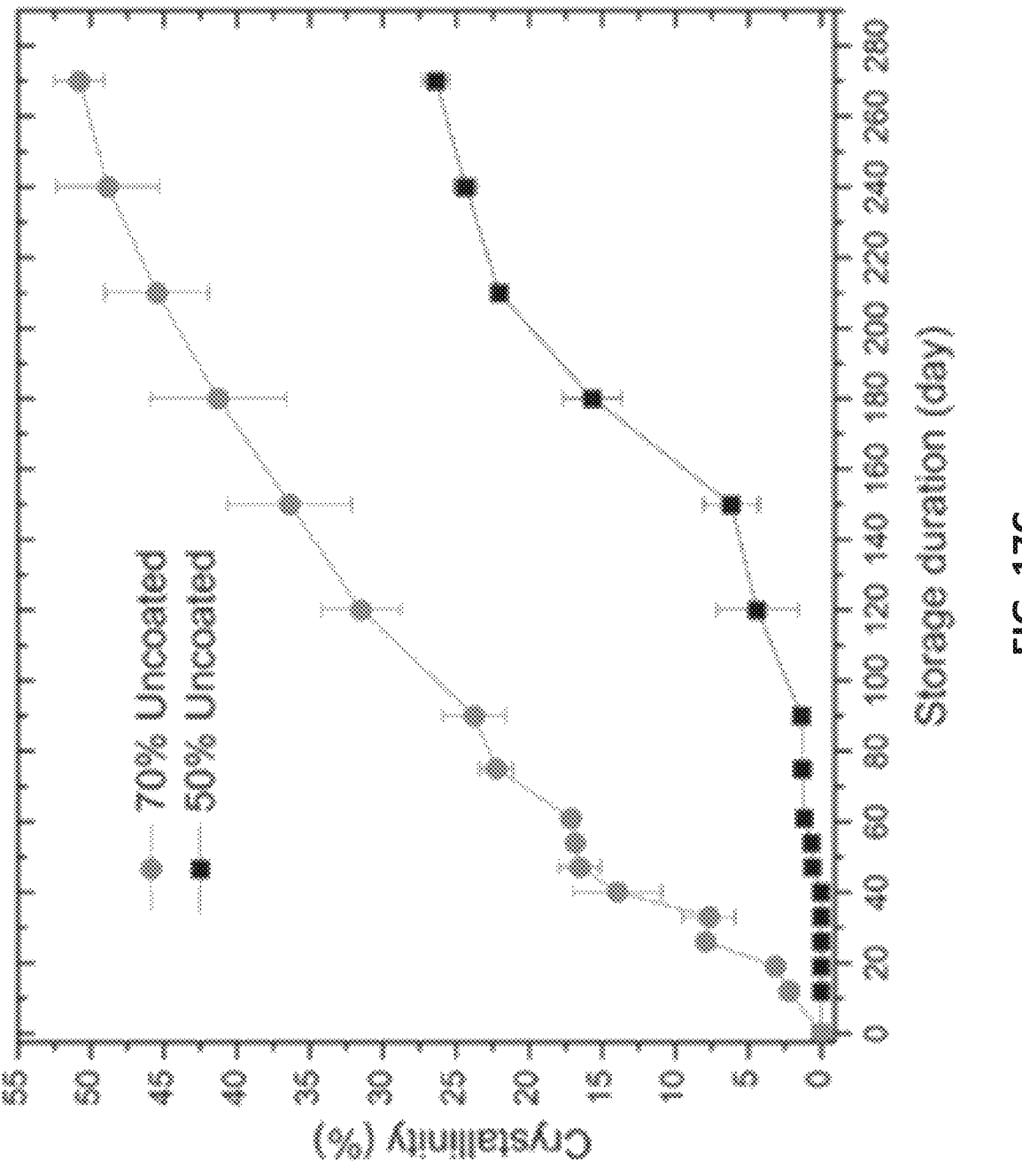

Samples of the coated and uncoated ASD particles (aluminum oxide/ezetimibe/HPMCAS) were analyzed by x-ray diffraction after 9 month storage at 40° C. and 75% relative humidity. As shown in FIG. 17, there was about 25% crystallinity for uncoated ASD with 50% API loading, about 50% crystallinity for uncoated ASD with 70% API loading, and no crystallization for most of the coated samples.

The samples were also assessed by scanning electron microscopy (SEM) to assess the particle morphology of uncoated and metal oxide coated ASD particles (aluminum oxide/ezetimibe/HPMCAS) after one year storage at 40° C. and 75% relative humidity. As shown in FIG. 19, both 50% and 70% uncoated ASD fully crystallized. There was no crystallization for 50% DL coated samples. There was a small amount of crystallization observed for 70% coated ASD.

Samples of the coated and uncoated ASD particles (aluminum oxide/ezetimibe/HPMCAS) were analyzed by x-ray diffraction after one year storage at 40° C. and 75% relative humidity. As shown in FIG. 20, there was significant crystallization for both 50% and 70% uncoated ASD, a small amount of crystallization for 70% thin coated ASD (B3-139A), and close to zero crystallization for most of the other coated samples.

Figure 12A:
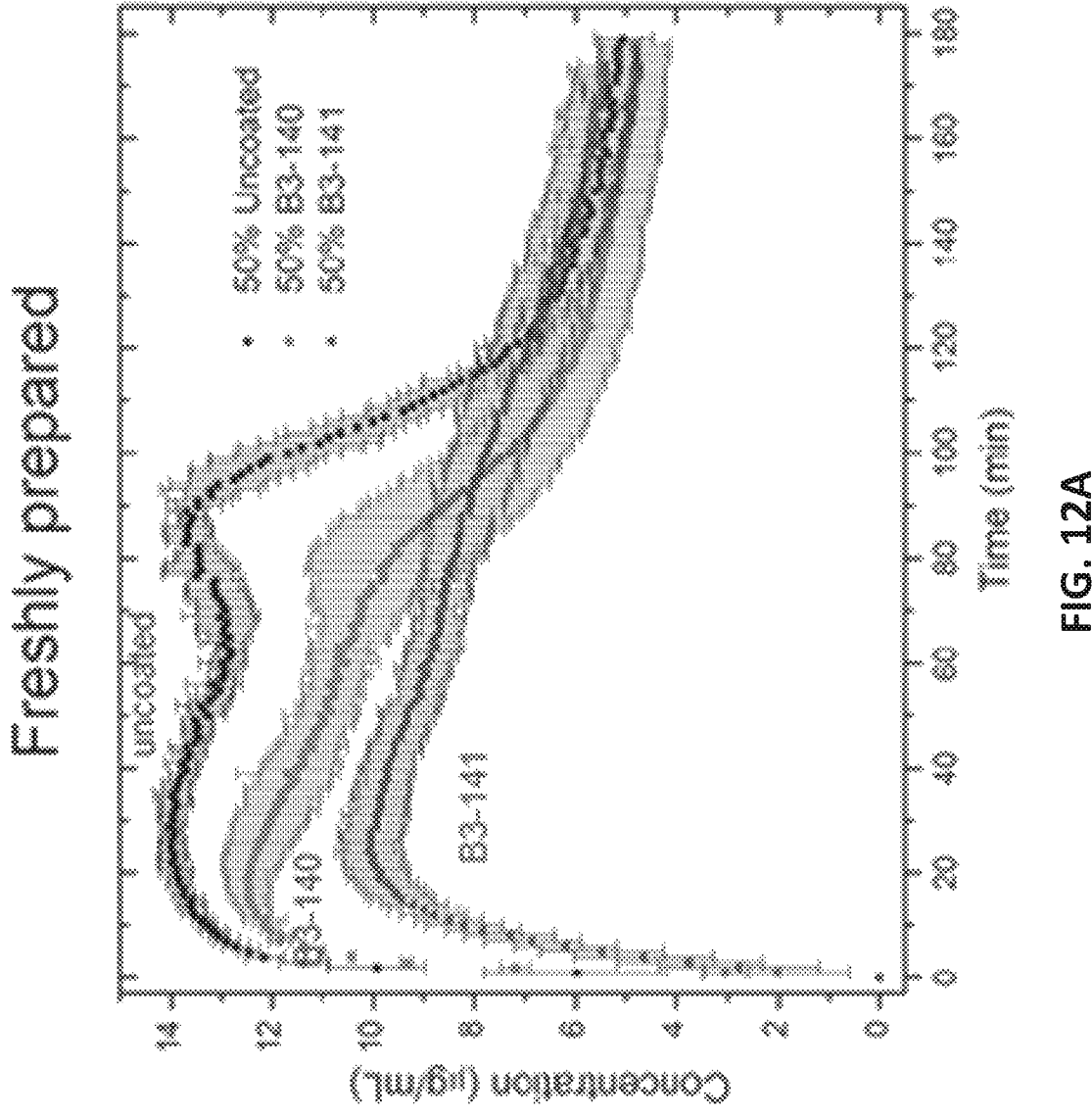
FIGS. 12A-12C depict the results of dissolution analysis of uncoated and metal oxide coated ASD particles under accelerated stability testing.
Figure 12B:
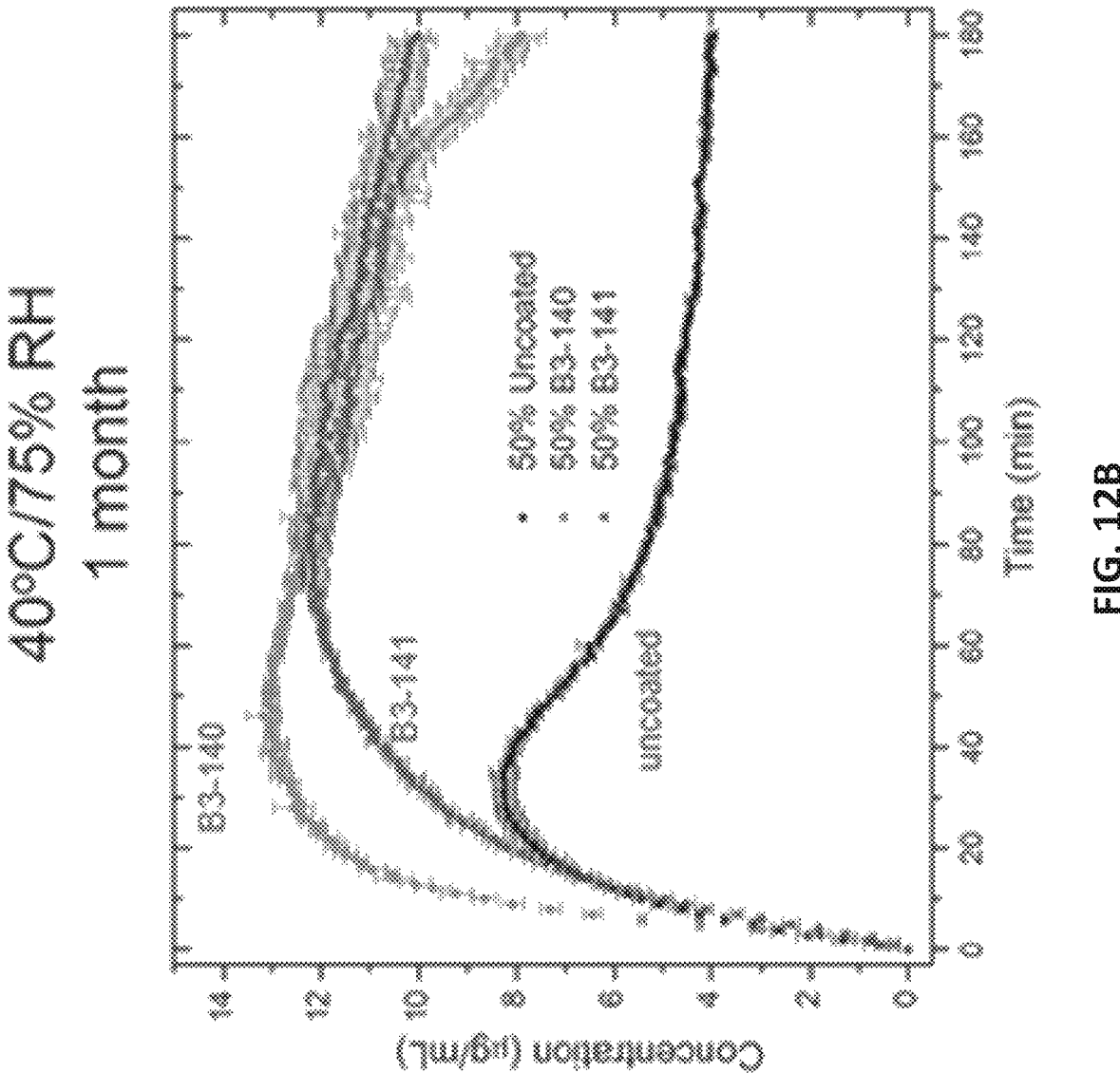
Figure 12C:
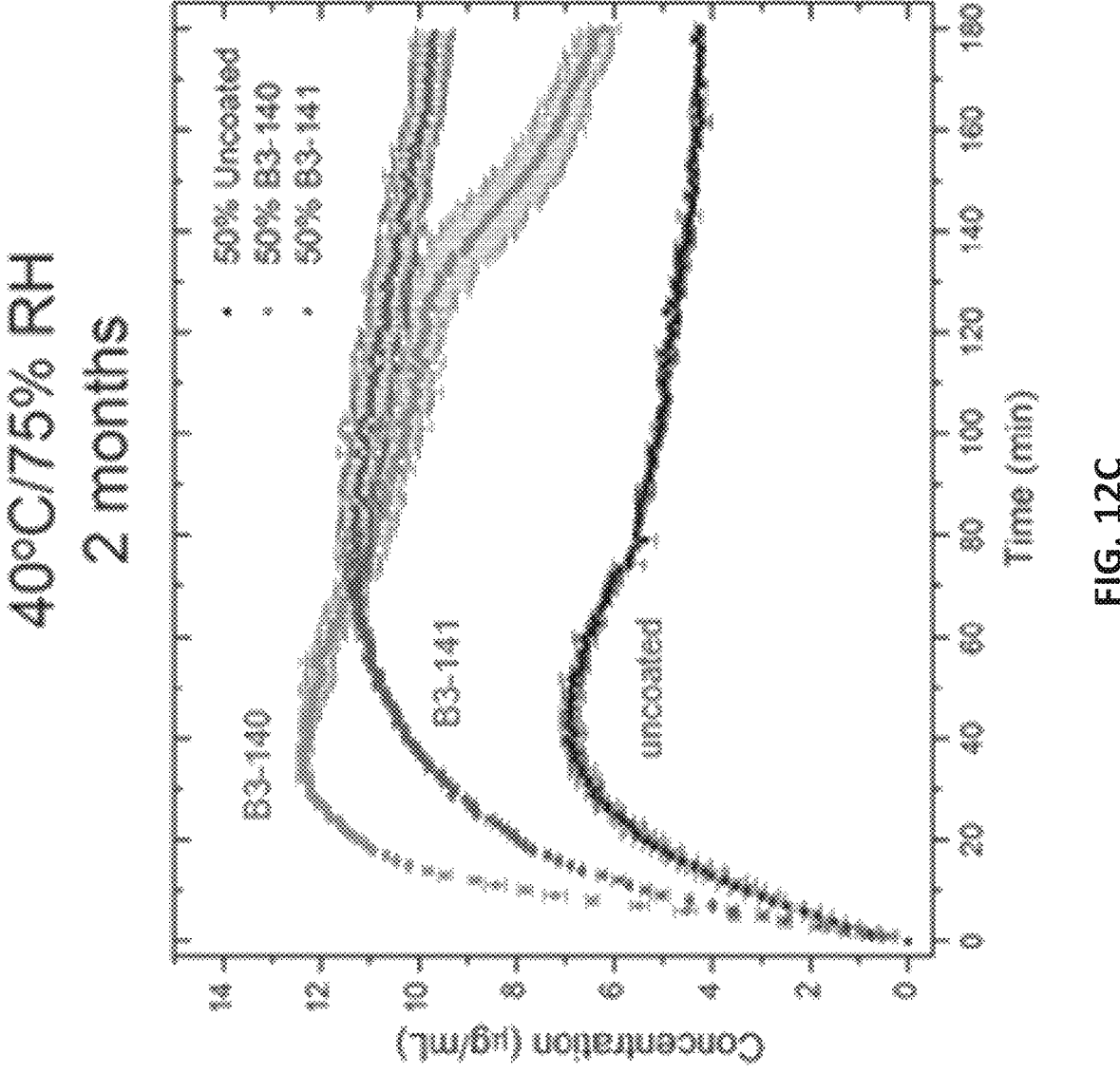
Figure 13A:
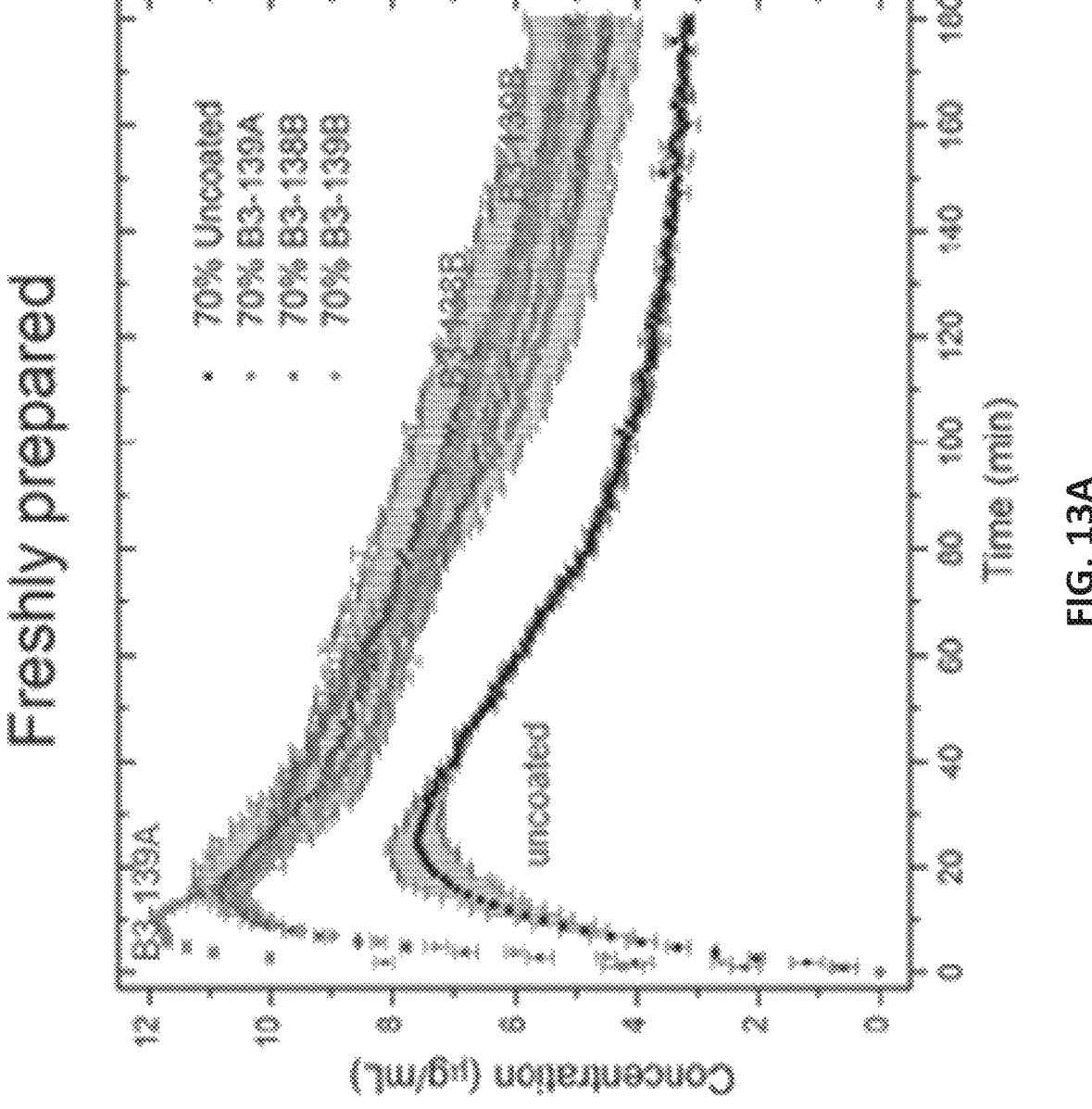
FIGS. 13A-13C depict the results of dissolution analysis of uncoated and metal oxide coated ASD particles under accelerated stability testing.
Figure 13B:
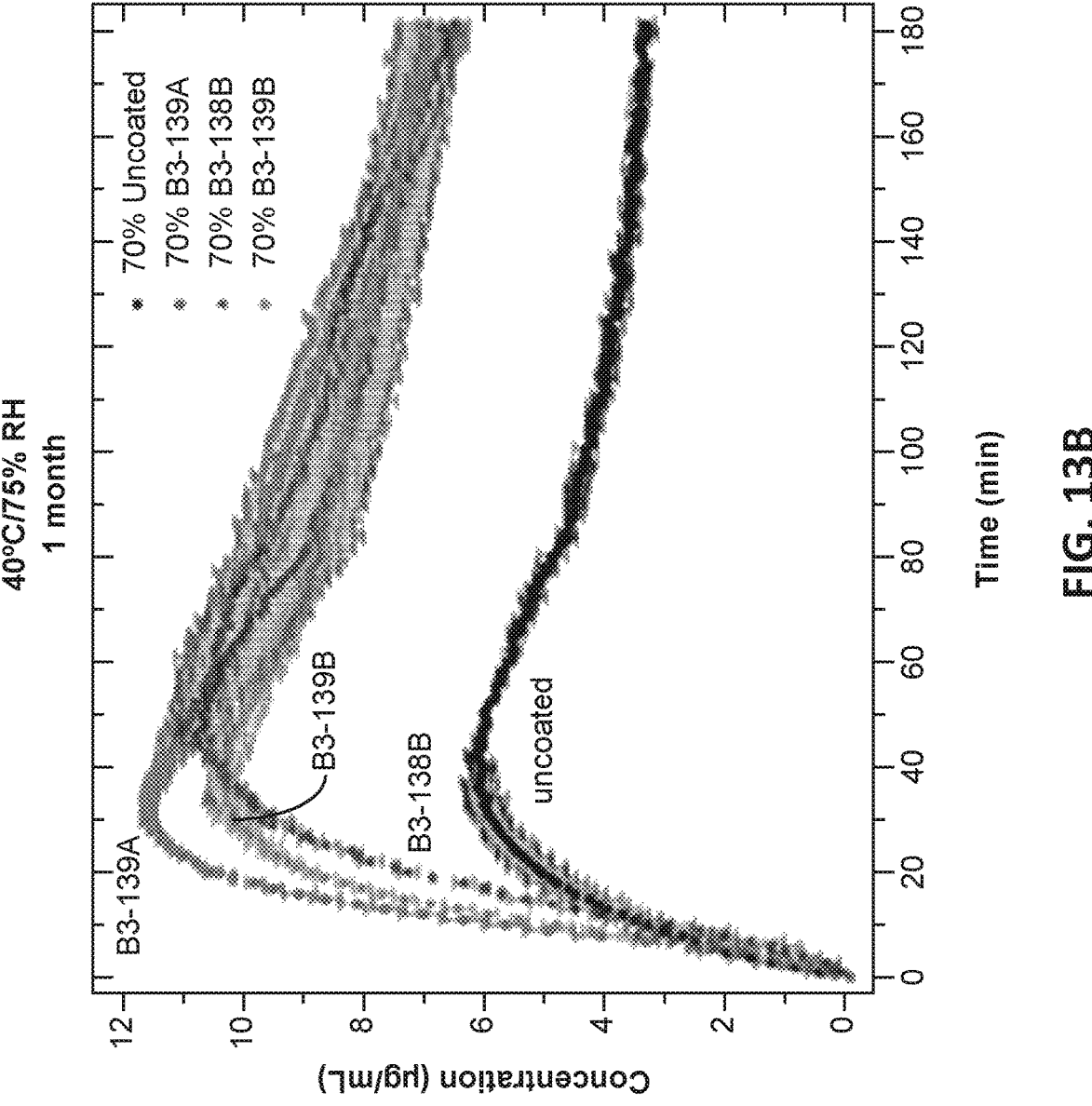
Figure 13C:
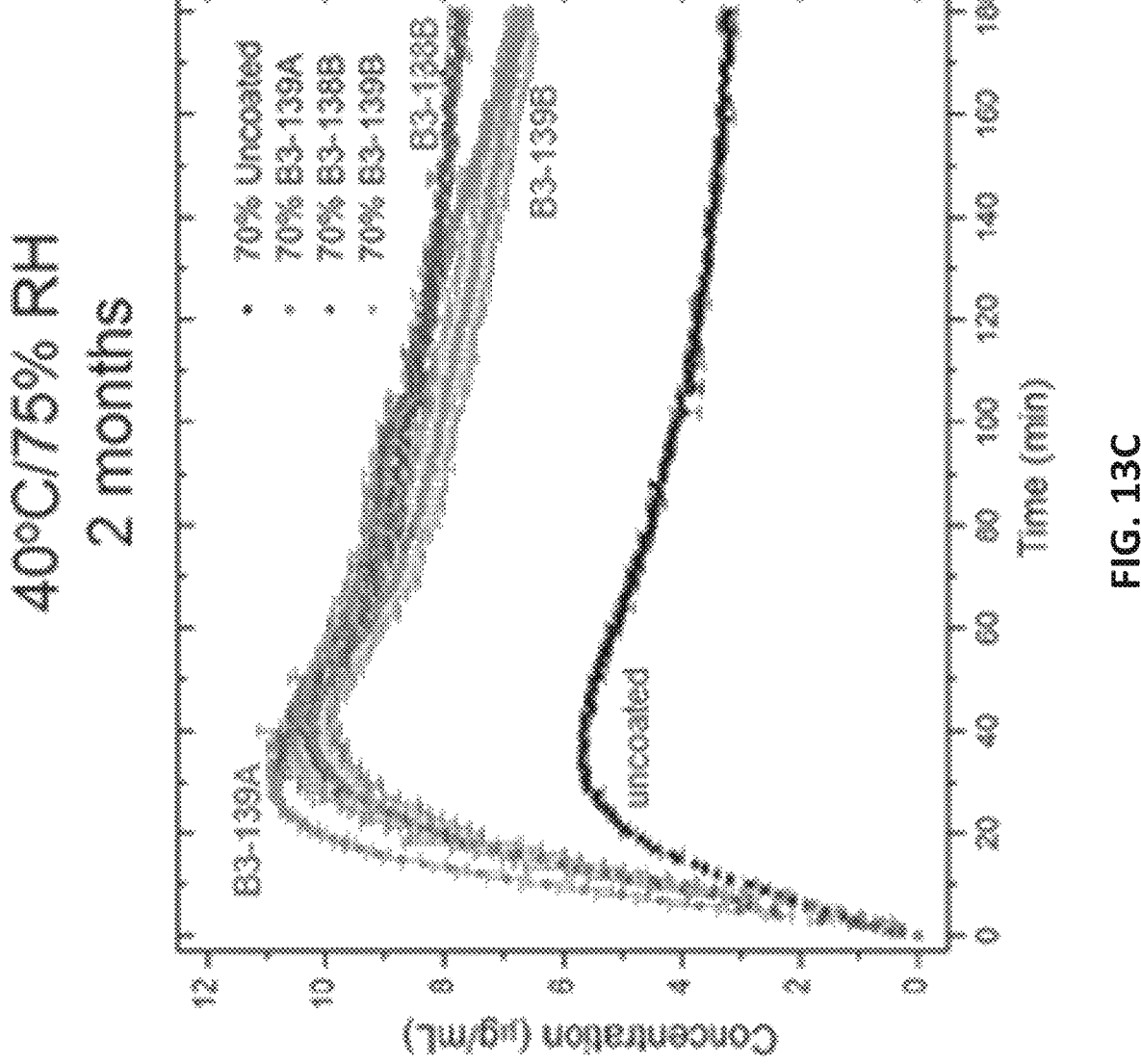

Example 3: Metal Oxide Coated ASD Particles are Resistant to Deterioration of API Release Crystallization decreases the solubility of ezetimibe. The release of ezetimibe from coated and uncoated ASD particles prepared as described in Example 1 was studied. In each case, the dissolution conditions were 37° C., 200 rpm stirring in 50 ml phosphate buffer of FaSSSIF (pH 6.5) solution and the amount of ASD particles used was equivalent to 10 mg of ezetimibe. Thus, in this release study, the maximum possible concentration of ezetimibe is 200 μg/ml. After adding the ASD particles equivalent to 10 mg ezetimibe, release profile data is collected by real time in situ UV dissolution measurements. As can be seen in FIG. 12, after 1 month at 40° C./75% relative humidity, the release rate of ezetimibe from the uncoated 50% drug loading ASD particles was greatly decreased. In contrast, the release rate from coated 50% drug loading ASD particles barely changed. As can be seen in FIG. 13, after 1 month at 40° C./75% relative humidity, the release rate of ezetimibe from the uncoated 70% drug loading ASD particles was greatly decreased. In contrast, the release rate from coated 70% drug loading ASD particles barely changed. The decrease release from uncoated particles is likely due to an increase in crystallinity and agglomeration over time. As shown in FIG. 18, the $C_{max}$ (maximum serum concentration) of uncoated samples was decreasing throughout the 9 month storage duration, whereas for coated samples, $C_{max}$ was fairly stable. Also, the $T_{max}$ (time at which $C_{max}$ is observed) of all samples significantly increased after one month storage, likely due to agglomeration or wetting. As shown in FIGS. 21A and 21B, ALD coating does not have any negative impact on the release profile of the ezetimibe. After 1 month or longer storage, the coated ASD particles show better release amount, likely because the coated ASD particles maintained the amorphous state of API. Here, the solubility of crystalline ezetimibe is 0.8+/−0.3 ug/mL and the solubility of amorphous ezetimibe is 20.2+/−0.4 ug/ml.

Example 4: Aluminum Oxide Coated Erlotinib HPMCAS ASD Particles (Aluminum Oxide/Erlotinib/HPMCAS) with 60% Drug Loading Particles of an ASD of erlotinib in hydroxypropyl methyl cellulose acetate succinate (HPMCAS) with 60% drug loading, were prepared by spray drying. The particles EH60-5 were coated with aluminum oxide by ALD at 35° C., essentially as described above. EH60-5 is the uncoated ASD particles (erlotinib/HPMCAS) with 60% drug loading. B3-281B is the coated ASD particles (aluminum oxide/erlotinib/HPMCAS) with 60% drug loading.

The freshly prepared uncoated and metal oxide coated ASD particles (aluminum oxide/erlotinib/HPMCAS) with 60% drug loading were tested for powder flowability. As shown in FIG. 23, the coated ASD particles show a higher conditioned bulk density (CBD) than the uncoated ASD particles based on powder flowability characterization of uncoated and metal oxide coated ASD particles (aluminum oxide/erlotinib/HPMCAS) with 60% drug loading. As shown in FIG. 23, the compressibility measured by percentage change in volume after compression under 15 kPa (CPS@15 kPa) is lower in coated ASD comparing to uncoated ASD. As shown in FIG. 23, the flow function coefficient after compression under 3 kPa (FFc@3 kPa) is higher in coated ASD comparing to uncoated ASD, improving the cohesive ASD powders to the easy flow region.

The freshly prepared uncoated and coated ASD particles (aluminum oxide/erlotinib/HPMCAS) with 60% drug loading were analyzed by x-ray diffraction. As shown in FIG. 24, there was no crystallization after coating based on x-ray diffraction analysis of uncoated and metal oxide coated ASD particles (aluminum oxide/erlotinib/HPMCAS) with 60% drug loading The freshly prepared uncoated and coated ASD particles (aluminum oxide/erlotinib/HPMCAS) with 60% drug loading were also analyzed by Fourier-transform infrared spectroscopy. As shown in FIGS. 25A and 25B, there was no change in FTIR spectra after coating based on FTIR analysis of uncoated and metal oxide coated ASD particles (aluminum oxide/erlotinib/HPMCAS) with 60% drug loading.

Example 5: Aluminum Oxide Coated Erlotinib PVPVA ASD Particles (Aluminum Oxide/Erlotinib/PVPVA) With 50% Drug Loading Particles of an ASD of erlotinib in polyvinylpyrrolidone-polyvinylacrylate copolymer (PVPVA) with 50% drug loading, were prepared by spray drying with the below parameters: 1) Inlet/Outlet Temp: 105° C./68° C.; 2) Spray Flow Rate (setting): 20%; 3) Aspirator: 100%; and 4) Gas Flow: 55. EP50-15 is the uncoated ASD particles (erlotinib/PVPVA) with 50% drug loading. B3-284A is the thin coated ASD particles (aluminum oxide/erlotinib/PVPVA) with 50% drug loading. B3-284B is the thick coated ASD particles (aluminum oxide/erlotinib/PVPVA) with 50% drug loading.

The fresh prepared thin coated ASD (B3-284A) and thick coated ASD (B3-284B) were analyzed to assess the coating thickness and oxide content. As shown in FIG. 26A, the thin coated ASD (B3-284A) has a coating thickness of about 4.4-5.5 nm and the thick coated ASD (B3-284B) has a coating thickness of about 8.8-9.4 nm. The thin coated ASD (B3-284A) has an oxide content of about 1.6% and the thick coated ASD (B3-284B) has an oxide content of about 3.31%. Isothermal moisture sorption was used to assess the moisture absorption tendency of the coated and uncoated ASD particles. As can be seen in FIG. 27, the uncoated and coated ASD particles (aluminum oxide/erlotinib/PVPVA) with 50% drug loading have comparable isotherms. Samples of the uncoated and coated ASD particles (aluminum oxide/erlotinib/PVPVA) with 50% drug loading that were stored in open bottles for 4 weeks at 40° C. and 43% relative humidity were analyzed by x-ray diffraction. As shown in FIG. 28, while crystallization starts in about 2-3 weeks for uncoated ASD particles (EP50-15), no crystallization was observed for coated ASD particles (B3-284A and B3-284B).

Samples of the uncoated and coated ASD particles (aluminum oxide/erlotinib/PVPVA) with 50% drug loading that were stored in open bottles for 4 weeks at 40° C. and 43% relative humidity were also analyzed by SEM. As shown in FIG. 29, while crystallization starts in about 1-2 weeks for uncoated ASD particles (EP50-15), no crystallization was observed for coated ASD particles (B3-284A and B3-284B).

Example 6 Metal Oxide Coated Nifedipine PVP ASD (Aluminum Oxide/Nifedipine/PVP or Titanium Oxide/Nifedipine/PVP) with 50% and 70% Drug Loading Particles of an ASD of nifedipine in polyvinylpyrrolidone (PVP) with 50% (SF20000521) or 70% (SF20000611) drug loading, were prepared by spray drying according to Table 2. The particles were coated with aluminum oxide by ALD at 35° C., essentially as described above.

TABLE 2

| Ingredients | Manufacturer | (50:50) % w/w Batch no: SF20000521 | (70:30 ) % w/w Batch no: SF20000611 |
|---|---|---|---|
| Nifedipine USP | Sharon bio medicals | 8 | 11.2 |
| PVPK-30 | BASF | 8 | 4.8 |
| IPA | Finar | 42 | 25.2 |
| Acetone | Emprove | 42 | 58.8 |

The size distribution, bulk density and tap density of the various uncoated and metal oxide coated ASD particles (aluminum oxide/nifedipine/PVP) with 50% (SF20000521) and 70% (SF20000611) drug loading are shown in Table 3.

TABLE 3

| Batch No. | D10 | D50 | D90 | Bulk density (g/ml) | Tap density (g/ml) |
|---|---|---|---|---|---|
| SF20000521A (uncoated) | 1.275 | 19.008 | 62.324 | 0.2941 | 0.6060 |
| SF20000521B (Coated) | 4.940 | 16.674 | 50.924 | 0.3921 | 0.6667 |
| SF20000611A (uncoated) | 10.834 | 34.011 | 92.747 | 0.2353 | 0.4878 |
| SF20000611B (Coated) | 7.026 | 21.371 | 57.231 | 0.400 | 0.625 |

The freshly prepared uncoated and metal oxide coated ASD particles (aluminum oxide/nifedipine/PVP) with 50% (SF20000521) and 70% (SF20000611) drug loading were analyzed for nifedipine content and water content. As shown in FIG. 30A, comparing to coated particles (SF20000521B and SF20000611B) the uncoated particles (SF20000521A and SF20000611A) have a higher nifedipine content and a higher water content.

As shown in FIG. 31, visual inspection of the freshly prepared uncoated and metal oxide coated ASD particles (aluminum oxide/nifedipine/PVP) with 50% (SF20000521) and 70% (SF20000611) drug loading do not show significant agglomeration.

PVP, nifedipine, freshly prepared uncoated and metal oxide coated ASD particles (aluminum oxide/nifedipine/PVP) with 50% (SF20000521) and 70% (SF20000611) drug loading were analyzed by x-ray diffraction. As shown in FIGS. 32A-32F, there was no crystallization.

The uncoated and metal oxide coated ASD particles (aluminum oxide/nifedipine/PVP) with 50% and 70% drug loading were subjected to moisture sorption analysis after storage in capped amber glass bottles, capped with induction sealed HDPE bottles, and open HDPE bottles with no cap for various durations. As shown in FIGS. 33A-33B, for 50% drug loading samples (SF20000521), the coated ASD particles show less impurities comparing to the uncoated ASD particles after storage under various conditions. As shown in FIGS. 33C-33D, for 70% drug loading samples (SF20000611), there is comparable impurities and moisture content for coated and uncoated ASD particles.

Samples of uncoated and metal oxide coated ASD particles (aluminum oxide/nifedipine/PVP) with 50% (SF20000521) and 70% (SF20000611) drug loading that were stored in open HDPE bottles with no cap for various durations at 40° C. and 75% relative humidity were subjected to visual inspection. As shown in FIG. 34, uncoated ASD with 50% drug loading (SF20000521A) and 70% drug loading (SF20000611A) show significant agglomeration (cake formation) and color change. No agglomeration was observed for the coated ASD with 50% drug loading (SF20000521B) and 70% drug loading (SF20000611B) after 3 months.

Samples of uncoated and metal oxide coated ASD particles (aluminum oxide/nifedipine/PVP) with 50% (SF20000521) and 70% (SF20000611) drug loading that were stored in capped with induction sealed HDPE bottles for various durations were subjected to visual inspection. As shown in FIG. 35, uncoated ASD with 50% drug loading (SF20000521A) and 70% drug loading (SF20000611A) show significant agglomeration (cake formation). No agglomeration was observed for the coated ASD with 50% drug loading (SF20000521B) and 70% drug loading (SF20000611B).

Samples of uncoated and metal oxide coated ASD particles (aluminum oxide/nifedipine/PVP) with 50% (SF20000521) and 70% (SF20000611) drug loading that were stored in capped amber bottles for various durations were subjected to visual inspection. As shown in FIG. 36, uncoated ASD with 50% drug loading (SF20000521A) and 70% drug loading (SF20000611A) show significant agglomeration (cake formation). No agglomeration was observed for the coated ASD with 50% drug loading (SF20000521B) and 70% drug loading (SF20000611B) after three months.

Samples of uncoated and metal oxide coated ASD particles (aluminum oxide/nifedipine/PVP) with 50% (SF20000521) and 70% (SF20000611) drug loading that were stored in capped amber bottles for 3 months at 25° C. and 60% relative humidity were subjected to X-ray diffraction analysis. As shown in FIG. 37, no crystallization was observed for either coated or uncoated samples.

Samples of uncoated and metal oxide coated ASD particles (aluminum oxide/nifedipine/PVP) with 50% (SF20000521) and 70% (SF20000611) drug loading that were stored in capped with induction sealed HDPE bottles for 3 months at 40° C. and 75% relative humidity were subjected to X-ray diffraction analysis. As shown in FIG. 38, for the 70% drug loading samples, there was significant crystallization in the uncoated sample (20000611A) and no crystallization in the coated sample (20000611B).

Samples of uncoated and metal oxide coated ASD particles (aluminum oxide/nifedipine/PVP) with 50% (SF20000521) and 70% (SF20000611) drug loading that were stored in open HDPE bottles with no cap for 3 months at 40° C. and 75% relative humidity were subjected to X-ray diffraction analysis. As shown in FIG. 39, for the 50% and 70% drug loading samples, there were significant crystallization in the uncoated sample (20000521A and 20000611A) and a relatively smaller amount of crystallization in the coated sample (20000521B and 20000611B).

The samples were also assessed by scanning electron microscopy (SEM) to assess the particle morphology of uncoated and metal oxide coated ASD particles (aluminum oxide/nifedipine/HPMCAS) with 50% (SF20000521) and 70% (SF20000611) drug loading after 3 month storage in open HDPE bottles with no cap at 40° C. and 75% relative humidity. As shown in FIG. 40A, the uncoated 50% and 70% drug loaded ASD particles show significant crystallization (completely gelled) after 3 month storage in open bottles. In fact, due to agglomeration, the SEM images had to be taken after the samples were ground/crushed to small pieces. By comparison, as shown in FIGS. 40B-40C, the coated 50% and 70% drug loaded ASD particles show no crystallization or morphology change after 3 month storage in open bottles.

What is claimed is:

1. Individual coated nanoparticles or microparticles, comprising:

(a) nanoparticles or microparticles comprising an amorphous solid dispersion (ASD) of an active pharmaceutical ingredient (API) and a polymer; and (b) a coating layer comprising an inorganic oxide selected from the group consisting of aluminum oxide, zinc oxide, silicon oxide and titanium oxide enclosing the individual nanoparticles or microparticles, wherein the nanoparticles or microparticles comprise 50%-70% wt/wt API, wherein the polymer is selected from the group consisting of HPMCAS, PVPVA and PVP, and the coating layer allows the ASD to remain amorphous for at least one month longer, as compared to an otherwise identical ASD without the coating layer, when stored at 40° C. and 75% humidity.

2. The individual coated nanoparticles or microparticles of claim 1, wherein the coating layer increases the glass transition temperature of the ASD.

3. The individual coated nanoparticles or microparticles of claim 1, wherein the nanoparticles or microparticles comprise at least 70% wt/wt API.

4. The individual coated nanoparticles or microparticles of claim 1, wherein the individual coated nanoparticles or microparticles have a D50 of 0.5 μm to 200 μm on a volume average basis.

5. The individual coated nanoparticles or microparticles of claim 1, wherein the individual coated nanoparticles or microparticles have a D90 of 200 μm to 2000 μm on a volume average basis.

6. The individual coated nanoparticles or microparticles of claim 1, wherein the coating layer has a thickness in range of 0.1 nm to 100 nm.

7. The individual coated nanoparticles or microparticles of claim 1, wherein the API is selected from the group consisting of ezetimibe, erlotinib and nifedipine.

8. The individual coated nanoparticles or microparticles of claim 1, wherein the inorganic oxide is selected from the group consisting of aluminum oxide and titanium oxide.

9. The individual coated nanoparticles or microparticles of claim 1, wherein the inorganic oxide is aluminum oxide.

10. The individual coated nanoparticles or microparticles of claim 1, wherein the individual coated nanoparticles or microparticles consist of the nanoparticles or microparticles and the coating layer enclosing the nanoparticles or microparticles.

11. The individual coated nanoparticles or microparticles of claim 1, wherein the coating layer reduces agglomeration during storage.

12. The individual coated nanoparticles or microparticles of claim 1, prepared by a method comprising:

(a) providing the nanoparticles or microparticles; and (b) performing vapor phase deposition to apply the coating layer to the nanoparticles or microparticles thereby preparing the individual coated nanoparticles or microparticles.

13. The individual coated nanoparticles or microparticles of claim 12, wherein step (b) takes place at a temperature between 25° C. and 50° C.

14. The individual coated nanoparticles or microparticles of claim 12, wherein the step (b) comprises:

(b1) loading the nanoparticles or microparticles into a reactor;

(b2) applying a vaporous or gaseous inorganic precursor to the nanoparticles or microparticles in the reactor;

(b3) purging using an inert gas or performing one or more pump-purge cycles using an inert gas;

(b4) applying a vaporous or gaseous oxidant to the nanoparticles or microparticles in the reactor; and (b5) purging using an inert gas or performing one or more pump-purge cycles using an inert gas.

15. The individual coated nanoparticles or microparticles of claim 12, wherein the coating layer increases the glass transition temperature of the ASD.

16. The individual coated nanoparticles or microparticles of claim 1, wherein the particles are stored in open bottles.

* * * * *